United States Patent
Bair et al.

(10) Patent No.: US 7,378,410 B2
(45) Date of Patent: May 27, 2008

(54) SUBSTITUTED LACTAMS AND THEIR USE AS ANTI-CANCER AGENTS

(75) Inventors: Kenneth Walter Bair, Oakland, CA (US); Frederick Ray Kinder, Jr., Morristown, NJ (US); Richard William Versace, Wanaque, NJ (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 10/565,700

(22) PCT Filed: Jul. 23, 2004

(86) PCT No.: PCT/EP2004/008284

§ 371 (c)(1),
(2), (4) Date: Jul. 28, 2006

(87) PCT Pub. No.: WO2005/014574

PCT Pub. Date: Feb. 17, 2005

(65) Prior Publication Data

US 2006/0281731 A1    Dec. 14, 2006

Related U.S. Application Data

(60) Provisional application No. 60/490,415, filed on Jul. 25, 2003.

(51) Int. Cl.
*C07D 223/12* (2006.01)
*A61K 31/55* (2006.01)

(52) U.S. Cl. .................. 514/212.03; 540/526; 540/527

(58) Field of Classification Search ............... 540/526, 540/527; 514/212.03
See application file for complete search history.

(56) References Cited

FOREIGN PATENT DOCUMENTS

| WO | WO00/29382 | 5/2000 |
|---|---|---|
| WO | WO01/85697 | 11/2001 |
| WO | WO02/39990 | 5/2002 |

OTHER PUBLICATIONS

Boeckman, Robert et al., "Synthesis of bengamides via polyol intermediate", Helvetica Chimica Acta, vol. 85, pp. 4532-4560, 2002.

Kinder, Frederick et al., "Synthesis and antitumour activity of ester modified analogues of bengamide B", J. Med. Chem, vol. 44, pp. 3692-3699, 2001.

*Primary Examiner*—Bruck Kifle

(57) ABSTRACT

This invention relates to certain substituted lactam compounds of the formula (I), particularly caprolactam compounds, which are useful for the treatment of cancer (I)

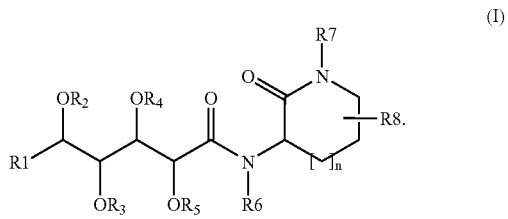

22 Claims, No Drawings

SUBSTITUTED LACTAMS AND THEIR USE AS ANTI-CANCER AGENTS

This application is the National Stage Application No. PCT/EP04/008284, filed on Jul. 23, 2004, which claims benefit under 35 U.S.C. §119(e) of U.S. Provisional Application No. 60/490,415, filed on Jul. 25, 2003. The contents of both are incorporated herein by reference in their entirety.

The present invention relates to the area of therapeutic agents for the treatment of cancer. More particularly, the present invention relates to certain substituted lactams, pharmaceutical compositions comprising said lactam compounds, a method of treating cancer with said lactam compounds, and a process for preparing said lactam compounds.

BACKGROUND

Cancer is a serious health problem throughout the world. As a result, an extensive number of research endeavors has been undertaken in an effort to develop therapies appropriate to the treatment and alleviation of cancer in humans. Research has been conducted to develop anti-cancer agents effective against various types of cancer. Oftentimes, anti-cancer agents which have been developed and found effective against cancer cells are, unfortunately, also toxic to normal cells. This toxicity manifests itself in weight loss, nausea, vomiting, hair loss, fatigue, itching, hallucinations, loss of appetite, and other undesirable effects.

Additionally, conventionally used cancer treatment agent often do not have the effectiveness desired or are not as broadly effective against different types of cancers as desired. As a result, a great need exists for therapeutic agents which are not only more effective against multiple types of cancer, but which have a higher degree of selectivity for killing cancer cells with no or minimal effect on normal healthy cells. In addition, highly effective and selective anti-cancer agents, In particular, against cancers of the colon, bladder, prostate, stomach, pancreas, breast, lung, liver, brain, testis, ovary, cervix, skin, vulva, small intestine, lymph glands, and blood cells are desired. Moreover, anti-cancer activity against colon, breast, lung, pancreas, and prostate cancers as well as melanomas are particularly desired because of the lack of any particular effective therapy at the present time.

SUMMARY

The present invention provides new anti-cancer agents which are effective against a variety of cancer cells in particular, against all liquid and solid cancers that may arise in a subject, including cancers of the colon, bladder, prostate, stomach, pancreas, breast, lung, liver, brain, testis, ovary, cervix, skin, vulva, small intestine, lymph glands, and blood cells. More particularly, the present invention relates to certain substituted lactams which exhibit a high degree of selectivity in killing cancer cells.

DETAILED DESCRIPTION

The invention relates to pharmaceutical compounds that are useful for the treatment of cancer of the formula I:

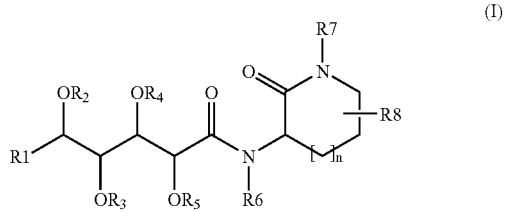

(I)

wherein
n is 0, 1 or 2;
R1 is H, $X_1$—$(C_{1-6})$alkyl-, $(C_{1-12})$alkylC(O)—, $X_2$—$(C_{2-4})$alkenylene-, $X_2$—$(C_{2-4})$alkynylene-, $X_1$—$(C_{3-9})$cycloalkyl-, $X_2$—$(C_{3-9})$cycloalkene-, $X_1$-aryl-, $X_1$—$(C_{3-7})$cycloalkane-$(C_{1-6})$alkylene-, $X_2$—$(C_{3-7})$cycloalkene-$(C_{1-6})$alkylene-, or $X_1$-aryl-$(C_{1-6})$alkylene-;
$X_1$ is H, $(C_{1-14})$alkyl, $(C_{3-7})$cycloalkyl, $(C_{1-14})$alkyl substituted by $(C_{3-7})$cycloalkyl, —$OR_a$, —$SR_a$, —$NO_2$, halo or $(C_{1-6})$alkylC(O)—; aryl, aryl-$(C_{1-12})$alkyl-, —$OR_a$, —$SR_a$, —$NO_2$, halo, $(C_{1-12})$alkyl-C(O)—, mono- or di-$(C_{1-4})$alkylamino, amino$(C_{1-16})$alkyl-, or mono- or di-$(C_{1-4})$alkylamino$(C_{1-16})$alkyl;
$X_2$ is H, $(C_{1-14})$alkyl, $(C_{3-7})$cycloalkyl, $(C_{1-14})$alkyl substituted by $(C_{3-7})$cycloalkyl, —$OR_a$—$SR_a$, —$NO_2$, halo or $(C_{1-6})$alkyl-C(O)—; aryl, aryl-$(C_{1-12})$alkyl-, amino$(C_{1-16})$alkyl- or mono- or di-$(C_{1-4})$alkylamino$(C_{1-16})$alkyl;
$R_a$ is H, $(C_{1-18})$alkyl, aryl, or $(C_{1-18})$alkyl substituted by $(C_{3-7})$cycloalkyl, aryl, —OH, —O—$(C_{1-6})$alkyl or halo;
$R_2$, $R_3$, $R_4$ and $R_5$ are independently hydrogen or $(C_{1-18})$alkyl, $R_5$ is also phenyl or $(C_{1-6})$alkyl which is substituted by phenyl, wherein there is no more than a total of 18 carbon atoms in the combined $R_2$, $R_3$, $R_4$ and $R_5$ alkyl substituents, or $R_2$ and $R_4$ together or $R_3$ and $R_5$ together form an acetal group;
R6 is hydrogen or $(C_{1-6})$alkyl;
R7 is H, $(C_{1-18})$alkyl, phenyl, pyridyl, $(C_{1-18})$alkyl substituted by $(C_{3-7})$cycloalkyl, —$OR_x$, $N_3$, halo, —$N(R_x)_2$, $R_x$, —O—$(C_{1-6})$alkyl, —OC(O)—$(C_{1-16})$alkyl or pyridyl; —Y—$R_b$ or a substituent of formula IIa or IIIa

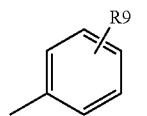

IIa

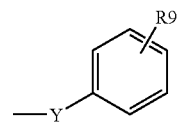

IIIa wherein
R9 is from 0 to 3 substituents selected from $(C_{1-6})$alkyl, —$OR_a$, —$SR_a$, —$NO_2$, halo, —$N_3$, $(C_{1-12})$alkylC(O)—, mono- or di-$(C_{1-4})$alkylamino, amino$(C_{1-16})$alkyl-, mono- or di-$(C_{1-4})$alkylamino$(C_{1-16})$alkyl, $(CH_2)_{0-2}$-$C_{5-7}$cycloalkyl, $(CH_2)_{0-2}$-heterocyclic, $(CH_2)_{0-2}$-$C_{5-7}$aryl, or $(CH_2)_{0-2}$-heteroaryl;
Y is a linking group selected from —$(C_{1-10})$alkyl-, —$(C_{0-10})$alkylene-CO—$N(R_x)$—$(C_{0-10})$alkylene-, —$(C_{0-10})$alkylene-$N(R_x)$—CO—$(C_{0-10})$alkylene-, —$(C_{0-10})$alkylene- CO—O—(C$_{0-10}$)alkylene-, —(C$_{1-10}$)alkylene-O—C(O)—(C$_{1-10}$)alkylene-, —(C$_{0-10}$)alkylene-CO—(C$_{0-10}$)alkylene-, —(C$_{0-10}$)alkylene-(R$_x$)N—CO—O—(C$_{0-10}$)alkylene-, —(C$_{0-10}$)alkylene-O—CO—(R$_x$)N—(C$_{0-10}$)alkylene- or —(C$_{0-18}$)alkylene-arylene-(C$_{0-18}$)alkylene-;

R$_x$ is H, (C$_{1-4}$)alkyl or phenyl;

R$_b$ is (C$_{1-16}$)alkyl or (C$_{1-16}$)alkyl which is substituted by (C$_{3-7}$)cycloalkyl, —OR$_x$, N$_3$, halo, —N(R$_x$)$_2$, —O—(C$_{1-6}$)alkyl, —OC(O)—(C$_{1-16}$)alkyl or pyridyl;

R8 is H, halo, —N$_3$, (C$_{1-16}$)alkyl, -Z-(C$_{1-16}$)alkyl, (C$_{1-16}$)alkyl substituted by (C$_{3-7}$)cycloalkyl, —N$_3$, —N(R$_x$)$_2$, -Z-het, —OR$_a$ or —SR$_a$, -Z-(C$_{1-16}$)alkyl substituted by (C$_{3-7}$)cycloalkyl, —N$_3$, —N(R$_x$)$_2$, -Z-het, —OR$_a$ or —SR$_a$, —O(C$_{1-16}$)alkylene-N$_3$, —O(C$_{1-16}$)alkylene-N(R$_x$)$_2$, —(C$_{0-6}$)alkylene-OC(O)—(C$_{1-16}$)alkyl, —(C$_{0-6}$)alkylene-(O)C—O—(C$_{1-16}$)alkyl, —(C$_{0-6}$)alkylene-OC(O)—(C$_{3-7}$)cycloalkyl, —(C$_{0-6}$)alkylene-(O)C—O—(C$_{3-7}$)cycloalkyl, pyridyl, —OC(O)O(C$_{1-12}$)alkyl, —O—CO—X—R$_z$, or —O—CO—(CH$_2$)$_m$—O—(CH$_2$)$_m$—X—R$_z$ wherein X is a direct bond, (C$_{1-12}$)alkylene, (C$_{1-12}$)alkenylene or (C$_{1-12}$)alkynylene and R$_z$ is H, (C$_{3-9}$)cycloalkyl, phenyl, phenyl substituted by one or more of chloro, methoxy, (C$_{1-18}$)alkyl or (C$_{1-18}$)alkoxy, pyrrolyl, furanyl, thiofuranyl, indolyl, benzofuranyl, benzothiofuranyl or pyridyl and each m is independently a number from 0 to 13, -Z-het, —OR$_a$, —SR$_a$, mono- or di-(C$_{1-4}$)alkylamino, amino(C$_{1-16}$)alkyl-, mono- or di-(C$_{1-4}$)alkylamino(C$_{1-16}$)alkyl, -Z-Si((C$_{1-6}$)alkyl)$_3$ or a substituent selected from the following two formulae:

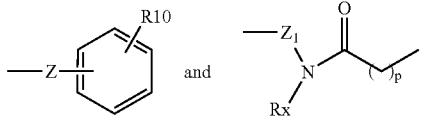

Z is a direct bond, —(C$_{1-12}$)alkylene-, —(C$_{1-12}$)alkylene-O—, —O—(C$_{1-12}$)alkylene-, —(C$_{1-12}$)alkylene-N(R$_x$)—, —N(R$_x$)—, —N(R$_x$)—(C$_{1-12}$)alkylene-, —N(R$_x$)—C(O)—, —N(R$_x$)—C(O)—(C$_{1-12}$)alkylene-, —(C$_{1-12}$)alkylene-N(R$_x$)—C(O)—, —(C$_{1-8}$)alkylene-N(R$_x$)—C(O)—(C$_{1-8}$)alkylene-, —(C$_{1-12}$)alkylene-CO—N(R$_x$)—, —CO—N(R$_x$)—(C$_{1-12}$)alkylene-, —(C$_{1-8}$)alkylene-CO—N(R$_x$)—(C$_{1-8}$)alkylene-, —CO—N(R$_x$)—, —(C$_{1-12}$)alkylene-CO—O—, —(C$_{1-12}$)alkylene-O—C(O)—, —OC(O)—(C$_{1-12}$)alkylene-, —C(O)—O—(C$_{1-12}$)alkylene-, —(C$_{1-12}$)alkylene-CO—, —(C$_{1-8}$)alkylene-CO—(C$_{1-8}$)alkylene-, —CO—(C$_{1-12}$)alkylene-, —C(O)—, —N(R$_x$)—C(O)—O—, —N(R$_x$)—C(O)—O—(C$_{1-12}$)alkylene-, —(C$_{1-12}$)alkylene-N(R$_x$)—C(O)—O—, —(C$_{1-8}$)alkylene-N(R$_x$)—C(O)—O—(C$_{1-8}$)alkylene-, —(C$_{1-12}$)alkylene-O—CO—N(R$_x$)—, —O—CO—N(R$_x$)—(C$_{1-12}$)alkylene-, —(C$_{1-8}$)alkylene-O—CO—N(R$_x$)—(C$_{1-8}$)alkylene-, —O—CO—N(R$_x$)—, —O—CO—O—, —(C$_{1-12}$)alkylene-O—CO—O—, —O—CO—O—(C$_{1-12}$)alkylene- or —(C$_{1-8}$)alkylene-O—C(O)—O—(C$_{1-8}$)alkylene-;

Z$_1$ is a direct bond, —(C$_{1-12}$)alkylene-, —O—(C$_{1-12}$)alkylene-, —N(R$_x$)—(C$_{1-12}$)alkylene-, —N(R$_x$)—C(O)—(C$_{1-12}$)alkylene-, —(C$_{1-8}$)alkylene-N(R$_x$)—C(O)—(C$_{1-8}$)alkylene-, —CO—N(R$_x$)—(C$_{1-12}$)alkylene-, —(C$_{1-8}$)alkylene-CO—N(R$_x$)—(C$_{1-8}$)alkylene-, —OC(O)—(C$_{1-12}$)alkylene-, —C(O)—O—(C$_{1-12}$)alkylene-, —(C$_{1-8}$)alkylene-CO—(C$_{1-8}$)alkylene-, —CO—(C$_{1-12}$)alkylene-, —C(O)—, —N(R$_x$)—C(O)—O—(C$_{1-12}$)alkylene-, —(C$_{1-8}$)alkylene-N(R$_x$)—C(O)—O—(C$_{1-8}$)alkylene-, —O—CO—N(R$_x$)—(C$_{1-12}$)alkylene-, —(C$_{1-8}$)alkylene-O—CO—N(R$_x$)—(C$_{1-8}$)alkylene-, —O—CO—O—(C$_{1-12}$)alkylene- or —(C$_{1-8}$)alkylene-O—C(O)—O—(C$_{1-8}$)alkylene-;

R10 is from 0 to 3 substituents selected from hydroxy, halo, —(C$_{1-17}$)alkyl, —O—(C$_{1-17}$)alkyl, —(CH$_2$)$_{1-6}$-C$_{3-7}$-cycloalkyl, —(CH$_2$)$_{0-10}$-aryl or —(CH$_2$)$_{0-10}$-het;

het is a heterocyclic or heteroaromatic ring;

p is 1-18;

or a pharmaceutically acceptable salt thereof;

with the proviso that when n is 2 and R$_1$ is (C$_{1-6}$)alkyl-CH=CH— or (C$_{3-6}$)cycloalkyl-CH=CH— then R$_7$ is not H or (C$_{1-8}$)alkyl or R$_8$ is not —O—CO—X—R$_z$ or —O—CO—(CH$_2$)$_m$—O—(CH$_2$)$_m$—X—R$_z$ where X is a direct bond, (C$_{1-12}$)alkylene, (C$_{1-12}$)alkenylene or (C$_{1-12}$)alkynylene and R$_z$ is H, (C$_{3-9}$)cycloalkyl, phenyl, phenyl substituted by one or more of chloro, methoxy, (C$_{1-18}$)alkyl or (C$_{1-18}$)alkoxy, pyrrolyl, furanyl, thiofuranyl, indolyl, benzofuranyl, benzothiofuranyl or pyridyl and each m is independently a number from 0 to 13, and with the further proviso that R$_8$ is not —OH when n is 2, R$_7$ is H or methyl and R$_1$ is 3-methylbut-1-enylene.

The present invention further also relates to compounds that are useful for the treatment of cancer of the formula I, wherein n is 0, 1 or 2;

R1 is X$_1$—(C$_{1-6}$)alkyl-, X$_2$—(C$_{2-4}$)alkenylene-, X$_2$—(C$_{2-4}$)alkynylene-, X$_1$—(C$_{3-9}$)cycloalkyl-, X$_2$—(C$_{3-9}$)cycloalkene-, X$_1$-aryl-, X$_1$—(C$_{3-7}$)cycloalkane-(C$_{1-6}$)alkylene-, X$_2$—(C$_{3-7}$)cycloalkene-(C$_{1-6}$)alkylene-, or X$_1$-aryl-(C$_{1-6}$)alkylene-;

X$_1$ is H, (C$_{1-14}$)alkyl, (C$_{3-7}$)cycloalkyl, (C$_{1-14}$)alkyl substituted by (C$_{3-7}$)cycloalkyl, —OR$_a$, —SR$_a$, —NO$_2$, halo or (C$_{1-6}$)alkylC(O)—; aryl, aryl-(C$_{1-12}$)alkyl-, —OR$_a$, —SR$_a$, —NO$_2$, halo, (C$_{1-12}$)alkyl-C(O)—, mono- or di-(C$_{1-4}$)alkylamino, amino(C$_{1-16}$)alkyl-, or mono- or di-(C$_{1-4}$)alkylamino(C$_{1-16}$)alkyl;

X$_2$ is H, (C$_{1-14}$)alkyl, (C$_{3-7}$)cycloalkyl, (C$_{1-14}$)alkyl substituted by (C$_{3-7}$)cycloalkyl, —OR$_a$—SR$_a$, —NO$_2$, halo or (C$_{1-6}$)alkyl-C(O)—; aryl, aryl-(C$_{1-12}$)alkyl-, amino(C$_{1-16}$)alkyl- or mono- or di-(C$_{1-4}$)alkylamino(C$_{1-16}$)alkyl;

R$_a$ is H, (C$_{1-18}$)alkyl, aryl, or (C$_{1-18}$)alkyl substituted by (C$_{3-7}$)cycloalkyl, aryl, —OH, —O—(C$_{1-6}$)alkyl or halo;

R$_2$, R$_3$, R$_4$ and R$_5$ are independently hydrogen or (C$_{1-18}$)alkyl, R$_5$ is also phenyl or (C$_{1-16}$)alkyl which is substituted by phenyl, wherein there is no more than a total of 18 carbon atoms in the combined R$_2$, R$_3$, R$_4$ and R$_5$ alkyl substituents, or R$_2$ and R$_4$ together or R$_3$ and R$_5$ together form an acetal group;

R6 is hydrogen or (C$_{1-6}$)alkyl;

R7 is H, (C$_{1-18}$)alkyl, phenyl, pyridyl, (C$_{1-18}$)alkyl substituted by (C$_{3-7}$)cycloalkyl, —OR$_x$, N$_3$, halo, —N(R$_x$)$_2$, —O—(C$_{1-6}$)alkyl, —OC(O)—(C$_{1-16}$)alkyl or pyridyl; —Y—R$_b$ or a substituent of formula IIa or IIIa

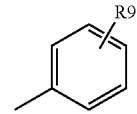

IIa

-continued

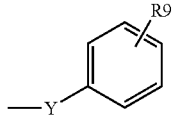
IIIa wherein

R9 is from 0 to 3 substituents selected from $(C_{1-6})$alkyl, —$OR_a$, —$SR_a$, —$NO_2$, halo, —$N_3$, $(C_{1-12})$alkylC(O)—, mono- or di-$(C_{1-4})$alkylamino, amino$(C_{1-16})$alkyl-, or mono- or di-$(C_{1-4})$alkylamino$(C_{1-16})$alkyl;

Y is a linking group selected from —$(C_{1-10})$alkyl-, —$(C_{0-10})$ alkylene-CO—N$(R_x)$—$(C_{0-10})$alkylene-, —$(C_{0-10})$alkylene-N$(R_x)$—CO—$(C_{0-10})$alkylene-, —$(C_{0-10})$alkylene-CO—O—$(C_{0-10})$alkylene-, —$(C_{1-10})$alkylene-O—C(O)—$(C_{1-10})$alkylene-, —$(C_{0-10})$alkylene-CO—$(C_{0-10})$ alkylene-, —$(C_{0-10})$alkylene-$(R_x)$N—CO—O—$(C_{0-10})$ alkylene-, —$(C_{0-10})$alkylene-O—CO—$(R_x)$N—$(C_{0-10})$ alkylene- or —$(C_{0-18})$alkylene-arylene-$(C_{0-18})$alkylene-;

$R_x$ is H, $(C_{1-4})$alkyl or phenyl;

$R_b$ is $(C_{1-16})$alkyl or $(C_{1-16})$alkyl which is substituted by $(C_{3-7})$cycloalkyl, —$OR_X$, $N_3$, halo, —$N(R_x)_2$, —O—$(C_{1-6})$alkyl, —OC(O)—$(C_{1-16})$alkyl or pyridyl;

R8 is H, halo, —$N_3$, $(C_{1-16})$alkyl, -Z-$(C_{1-16})$alkyl, $(C_{1-16})$ alkyl substituted by $(C_{3-7})$cycloalkyl, —$N_3$, —N$(R_x)_2$, -Z-het, —$OR_a$ or —$SR_a$, -Z-$(C_{1-16})$alkyl substituted by $(C_{3-7})$cycloalkyl, —$N_3$, —$N(R_x)_2$, -Z-het, —$OR_a$ or —$SR_a$, —O$(C_{1-16})$alkylene-$N_3$, —O$(C_{1-16})$alkylene-N$(R_x)_2$, —$(C_{0-6})$alkylene-OC(O)—$(C_{1-16})$alkyl, —$(C_{0-6})$ alkylene-(O)C—O—$(C_{1-16})$alkyl, —$(C_{0-6})$alkylene-OC(O)—$(C_{3-7})$cycloalkyl, —$(C_{0-6})$alkylene-(O)C—O—$(C_{3-7})$cycloalkyl, pyridyl, —OC(O)O$(C_{1-12})$alkyl, -Z-het, —$OR_a$, —$SR_a$, mono- or di-$(C_{1-4})$alkylamino, amino$(C_{1-16})$alkyl-, mono- or di-$(C_{1-4})$alkylamino$(C_{1-16})$ alkyl, -Z-Si$((C_{1-6})$alkyl$)_3$ or a substituent selected from the following two formulae:

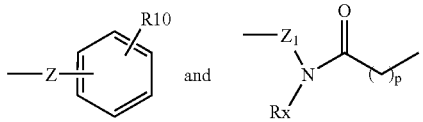

Z is a direct bond, —$(C_{1-12})$alkylene-, —$(C_{1-12})$alkylene-O—, —O—$(C_{1-12})$alkylene-, —$(C_{1-12})$alkylene-N$(R_x)$—, —N$(R_x)$—, —N$(R_x)$—$(C_{1-12})$alkylene-, —N$(R_x)$—C(O)—, —N$(R_x)$—C(O)—$(C_{1-12})$alkylene-, —$(C_{1-12})$ alkylene-N$(R_x)$—C(O)—, —$(C_{1-8})$alkylene-N$(R_x)$—C(O)—$(C_{1-8})$alkylene-, —$(C_{1-12})$alkylene-CO—N$(R_x)$—, —CO—N$(R_x)$—$(C_{1-12})$alkylene-, —$(C_{1-8})$alkylene-CO—N$(R_x)$—$(C_{1-8})$alkylene-, —CO—N$(R_x)$—, —$(C_{1-12})$alkylene-CO—O—, —$(C_{1-12})$alkylene-O—C(O)—, —OC(O)—$(C_{1-12})$alkylene-, —C(O)—O—$(C_{1-12})$alkylene-, —$(C_{1-12})$alkylene-CO—, —$(C_{1-8})$alkylene-CO—$(C_{1-8})$alkylene-, —CO—$(C_{1-12})$alkylene-, —C(O)—, —N$(R_x)$—C(O)—O—, —N$(R_x)$—C(O)—O—$(C_{1-12})$alkylene-, —$(C_{1-12})$alkylene-N$(R_x)$—C(O)—O—, —$(C_{1-8})$alkylene-N$(R_x)$—C(O)—O—$(C_{1-8})$alkylene-, —$(C_{1-12})$alkylene-O—CO—N$(R_x)$—, —O—CO—N$(R_x)$—$(C_{1-12})$alkylene-, —$(C_{1-8})$alkylene-O—CO—N$(R_x)$—$(C_{1-8})$alkylene-, —O—CO—N$(R_x)$—, —O—CO—O—, —$(C_{1-12})$alkylene-O—CO—O—, —O—CO—O—$(C_{1-12})$alkylene- or —$(C_{1-8})$alkylene-O—C(O)—O—$(C_{1-8})$alkylene-;

$Z_1$ is a direct bond, —$(C_{1-12})$alkylene-, —O—$(C_{1-12})$alkylene-, —N$(R_x)$—$(C_{1-12})$alkylene-, —N$(R_x)$—C(O)—$(C_{1-12})$alkylene-, —$(C_{1-8})$alkylene-N$(R_x)$—C(O)—$(C_{1-8})$ alkylene-, —CO—N$(R_x)$—$(C_{1-12})$alkylene-, —$(C_{1-8})$ alkylene-CO—N$(R_x)$—$(C_{1-8})$alkylene-, —OC(O)—$(C_{1-12})$alkylene-, —C(O)—O—$(C_{1-12})$alkylene-, —$(C_{1-8})$ alkylene-CO—$(C_{1-8})$alkylene-, —CO—$(C_{1-12})$alkylene-, —C(O)—, —N$(R_x)$—C(O)—O—$(C_{1-12})$alkylene-, —$(C_{1-8})$alkylene-N$(R_x)$—C(O)—O—$(C_{1-8})$alkylene-, —O—CO—N$(R_x)$—$(C_{1-12})$alkylene-, —$(C_{1-8})$alkylene-O—CO—N$(R_x)$—$(C_{1-8})$alkylene-, —O—CO—O—$(C_{1-12})$alkylene- or —$(C_{1-8})$alkylene-O—C(O)—O—$(C_{1-8})$alkylene-;

R10 is from 0 to 3 substituents selected from hydroxy, halo, —$(C_{1-17})$alkyl, —O—$(C_{1-17})$alkyl, —$(CH_2)_{1-6}$—$C_{3-7}$-cycloalkyl, —$(CH_2)_{0-10}$-aryl or —$(CH_2)_{0-10}$-het;

het is a heterocyclic or heteroaromatic ring;

p is 1-18;

or a pharmaceutically acceptable salt thereof;

with the proviso that when n is 2 and $R_1$ is $(C_{1-6})$alkyl-CH═CH— or $(C_{3-6})$cycloalkyl-CH═CH— then $R_7$ is not H or $(C_{1-8})$alkyl or $R_8$ is not —CO—X—$R_z$ or —CO—$(CH_2)_m$—O—$(CH_2)_m$—X—$R_z$ where X is a direct bond, $(C_{1-12})$alkylene, $(C_{1-12})$alkenylene or $(C_{1-12})$alkynylene and $R_z$ is H, $(C_{3-9})$cycloalkyl, phenyl, phenyl substituted by one or more of chloro, methoxy, $(C_{1-18})$alkyl or $(C_{1-18})$alkoxy, pyrrolyl, furanyl, thiofuranyl, indolyl, benzofuranyl, benzothiofuranyl or pyridyl and each m is independently a number from 0 to 13, and with the further proviso that $R_8$ is not —OH when n is 2, $R_7$ is H or methyl and $R_1$ is 3-methylbut-1-enylene.

Interesting compounds of formula I are those wherein:

n is 2; and/or

R1 is $X_1$—$(C_{1-6})$alkyl-, $X_2$—$(C_{2-4})$alkenylene-, $X_1$—$(C_{3-7})$ cycloalkyl-, or $X_1$—$(C_{3-7})$cycloalkane-$(C_{1-3})$alkylene-; and/or $X_1$ is H, $(C_{1-12})$alkyl, especially branched $(C_{1-6})$alkyl; $(C_{3-7})$ cycloalkyl, —$(C_{1-12})$alkyl substituted by $(C_{3-7})$cycloalkyl, —$OR_a$; —$SR_a$, —$NO_2$, halo or $(C_{1-12})$alkylC(O)—; aryl, aryl-$(C_{1-12})$alkyl- or —$OR_a$; and/or $X_2$ is H, $(C_{1-12})$alkyl, $(C_{3-7})$cycloalkyl, —$(C_{1-12})$alkyl substituted by $(C_{3-7})$cycloalkyl, —$OR_a$, —$SR_a$, —$NO_2$, halo or $(C_{1-12})$alkylC(O)—, aryl, aryl-$(C_{1-12})$alkyl-; and/or $R_a$ is H, $(C_{1-18})$alkyl, aryl-, or $(C_{1-18})$alkyl substituted by $(C_{3-7})$cycloalkyl or aryl;

$R_2$, $R_3$, $R_4$ and $R_5$ are independently hydrogen or $(C_{1-4})$alkyl, wherein there is no more than a total of 8 carbon atoms, especially no more than 4 carbon atoms, in the combined $R_2$, $R_3$, $R_4$ and $R_5$ alkyl substituents; and/or R6 is hydrogen or $(C_{1-6})$alkyl; and/or R7 is H, $(C_{1-8})$alkyl, $R_x$, $(C_{1-18})$alkyl substituted by $(C_{3-7})$ cycloalkyl, —$OR_x$, $N_3$, halo, —$N(R_x)_2$, —O—$(C_{1-6})$ alkyl, —OC(O)—$(C_{1-16})$alkyl or pyridyl; especially 3-pyridyl, or a substituent of formula IIa or IIIa

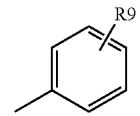
IIa

-continued

IIIa

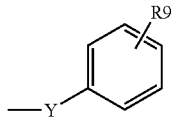

and/or
R9 is from 0 to 3 substituents selected from $(C_{1-6})$alkyl, —$OR_a$, —$SR_a$, —$NO_2$, halo, or —$N_3$; and/or
Y is a linking group selected from —C(O)N($R_x$)—, —CO—O—, —$(C_{1-12})$alkylene-CO—O—, —CO—O—$(C_{1-12})$alkylene-, —$(C_{1-10})$alkylene-CO—O—$(C_{1-10})$alkylene-, —$(C_{1-10})$alkylene-O—C(O)—$(C_{1-10})$alkylene-, —CO—, —$(C_{1-12})$alkylene-CO—, —CO—$(C_{1-12})$alkylene-, —$(C_{1-10})$alkylene-CO—$(C_{1-10})$alkylene-, —$(C_{1-12})$alkylene-($R_x$)N—CO—, —$(C_{1-10})$alkylene-($R_x$)N—CO—O—$(C_{1-10})$alkylene-, or —$(C_{0-12})$alkylene-arylene-$(C_{0-12})$alkylene-; and/or
$R_x$ is H, $(C_{1-4})$alkyl or phenyl;
R8 is —$N_3$, $(C_{1-16})$alkyl -Z-$(C_{1-16})$alkyl, $(C_{1-16})$alkyl substituted by $(C_{3-7})$cycloalkyl, —$N_3$, or —$N(R_x)_2$; -Z-$(C_{1-16})$alkyl substituted in the alkyl portion by $(C_{3-7})$cycloalkyl, —$N_3$, or —$N(R_x)_2$, —$(C_{0-6})$alkylene-(O)C—O—$(C_{1-16})$alkyl or a substituent selected from the following two formulae:

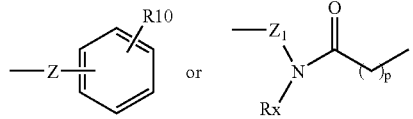

and/or
Z is a direct bond, —$(C_{1-12})$alkylene-, —N($R_x$)—C(O)—, —N($R_x$)—C(O)—$(C_{1-12})$alkylene-, —$(C_{1-12})$alkylene-N($R_x$)—C(O)—, —$(C_{1-8})$alkylene-N($R_x$)—C(O)—$(C_{1-8})$alkylene-, —$(C_{1-12})$alkylene-CO—N($R_x$)—, —CO—N($R_x$)—$(C_{1-12})$alkylene-, —$(C_{1-8})$alkylene-CO—N($R_x$)—$(C_{1-8})$alkylene-, —CO—N($R_x$)—, —C(O)—O—$(C_{1-12})$alkylene-, —CO—$(C_{1-12})$alkylene-, —C(O)—, —N($R_x$)—C(O)—O—, —N($R_x$)—C(O)—O—$(C_{1-12})$alkylene-, —$(C_{1-12})$alkylene-N($R_x$)—C(O)—O—, —$(C_{1-8})$alkylene-N($R_x$)—C(O)—O—$(C_{1-8})$alkylene-, —$(C_{1-12})$alkylene-O—CO—N($R_x$)—, —O—CO—N($R_x$)—$(C_{1-12})$alkylene-, —$(C_{1-8})$alkylene-O—CO—N($R_x$)—$(C_{1-8})$alkylene- or —O—CO—N($R_x$)—; and/or
$Z_1$ is a direct bond, —$(C_{1-12})$alkylene- or —C(O)—; and/or
R10 is from zero to 3 substituents selected from hydroxy, halo, —$(C_{1-17})$alkyl, —O—$(C_{1-17})$alkyl, —$(CH_2)_{1-6}$—$C_{3-7}$-cycloalkyl, —$(CH_2)_{0-10}$-aryl or —$(CH_2)_{0-10}$-het; and/or het is pyridyl.

Further interesting compounds of formula (I) include those wherein
R1 is $(C_{1-6}$ alkyl)-ethenylene-; especially those wherein the alkyl group is branched and the double bond is trans; and/or
$R_2$, $R_3$ and $R_4$, independently are hydrogen or $(C_{1-4})$alkyl, wherein there is no more than a total of 4 carbon atoms in the combined $R_2$, $R_3$, $R_4$ and $R_5$ alkyl substituents; and/or
$R_5$ is $(C_{1-4})$alkyl, especially methyl, and/or
R6 is hydrogen or methyl; and/or
R7 is H or $(C_{1-6})$alkyl; and/or R8 is H, —$N_3$, $(C_{1-16})$alkyl, -Z-$(C_{1-16})$alkyl, $(C_{1-16})$alkyl substituted by $(C_{3-7})$cycloalkyl, —$N_3$, or —$N(R_x)_2$ or -Z-$(C_{1-16})$alkyl substituted in the alkyl portion by $(C_{3-7})$cycloalkyl, —$N_3$, or —$N(R_x)_2$,
R9 is $(CH_2)_{0-2}$—$C_{5-7}$ cycloalkyl, $(CH_2)_{0-2}$—$C_{5-7}$ heterocyclic, $(CH_2)_{0-2}$—$C_{5-7}$ aryl, or $(CH_2)_{0-2}$—$C_{5-7}$ heteroaryl;
X is $(C_{1-12})$alkylene or $(C_{2-12})$alkenylene; and/or
R10 is from 0 to 3 substituents selected from hydroxy, halo, —$(C_{1-8})$alkyl, —O—$(C_{1-8})$alkyl, —$(CH_2)_{1-6}$—$C_{3-7}$-cycloalkyl, —$(CH_2)_{0-10}$-aryl or —$(CH_2)_{0-10}$-het; and/or
het is pyridyl;

especially those wherein n is 2.
Additional interesting compounds are those of formula I where
R1 is —CH=CH-i-propyl or —CH=CH-t-butyl, especially in the trans geometry;
$X_2$ is H;
$R_2$, $R_3$, $R_4$, and $R_5$ independently are hydrogen or methyl;
R6 is hydrogen;
R7 is H or $(C_{1-3})$ alkyl;

especially wherein n is 2.
Additional interesting compounds are those of formula I wherein:
R1 is $X_1$—$(C_{3-7})$-cycloalkane-$(C_{1-6})$alkylene- or $X_2$—$(C_{3-9})$ cycloalkene-;
$X_1$ is hydrogen;
$X_2$ is hydrogen;
$R_2$, $R_3$, $R_4$ and $R_5$ independently are hydrogen or methyl;
$R_6$ is hydrogen;
$R_7$ is H or $(C_{1-3})$alkyl;
$R_8$ is H; and
n is 2.

In another embodiment, the invention provides pharmaceutical compositions, especially for the treatment of cancer in subjects, especially human, comprising a pharmaceutically acceptable carrier or diluent and an antitumorally effective dose of a compound of formula I above, or a pharmaceutically acceptable salt thereof, where possible.

In still another embodiment, the current invention provides a method for treating cancer comprising administering to a subject, especially human, in need of such treatment a therapeutically effective amount of a compound of formula I above, or a pharmaceutically acceptable salt thereof, where possible. The effective dosage of the compounds of the invention for such treatment may encompass a range of from about 0.01 milligrams per kilogram body weight per day to about 0.02 grams per kilogram of body weight per day.

In another embodiment, the current invention relates to the use of a compound of formula I or of a pharmaceutically acceptable salt of such a compound for the preparation of a pharmaceutical composition for use in the chemotherapy of cancer.

Furthermore, the current invention relates to the use of a compound of formula I or of a pharmaceutically acceptable salt of such a compound for the chemotherapy of cancer.

In the above definitions:

The alkyl groups, including any alkyl portion of a substituent, such as alkoxy, are either straight or branched chain, of which examples of the latter include isopropyl, isobutyl, t-butyl, isopentyl, neopentyl, isohexyl, 3-methylpentyl, 2,2-dimethylbutyl, 2,3-dimethylbutyl and 1,1,2,2-tetramethylethyl unless otherwise noted.

The term "alkylene" as used herein refers to a straight or branched chain consisting solely of carbon and hydrogen.

Examples of "alkylene" groups include methylene, ethylene, propylene, butylene, pentylene, and 3-methypentylene.

The term "alkenylene" as used herein refers to a straight or branched chain consisting solely of carbon and hydrogen, containing at least one carbon-carbon double bond. Examples of "alkenylene" groups include ethenylene, propenylene, butenylene, 3,3,-dimethylbut-1-enylene, 3-methylbut-1-enylene, pentenylene, 3-methylpentenylene, and butadiene.

The term "alkynylene" as used herein refers to a straight or branched chain divalent group consisting solely of carbon and hydrogen containing at least one carbon-carbon triple bond. Examples of "alkynylene" groups include acetylene, propynylene, butynylene, pentynylene, 3-methylpentynylene.

If $R_2$ and $R_4$ together or $R_3$ and $R_5$ together form an acetal group, $R_2$ and $R_4$ together or $R_3$ and $R_5$ together preferably form a group of the formula —C(R')(R")—, wherein R' and R" are selected independently of each other from $X_1$—($C_{1-6}$)alkyl-, $X_2$—($C_{2-4}$)alkenyl-, $X_1$—($C_{3-7}$)cycloalkyl-, or $X_1$—($C_{3-7}$)cycloalkane-($C_{1-3}$)alkyl- wherein $X_1$ is as defined herein.

The term "direct bond" as herein described refers to a single, double, or triple, covalent atomic bond which links together two moieties.

Halo is chloro, bromo, iodo or fluoro, especially chloro, bromo or iodo.

The substituent het is preferably a 3 to 9 membered aliphatic ring, such as a 4 to 7 membered aliphatic ring, containing from one to three heteroatoms selected from nitrogen, sulfur and oxygen, or het is a 5 to 7 member aromatic ring containing one or more heteroatoms, for example from 1 to 4 heteroatoms, selected from N, O and S, or het is a bicyclic and tricyclic fused ring system where each ring can independently be 5 or 6 membered and contain one or more heteroatoms, for example, 1, 2, 3, or 4 heteroatoms, chosen from O, N or S such that the fused ring system is aromatic. Examples of suitable het substituents include pyrrolidyl, tetrahydrofuryl, tetrahydrothiofuranyl, piperidyl, piperazyl, tetrahydropyranyl, morphilino, 1,3-diazapane, 1,4-diazapane, 1,4-oxazepane, 1,4-oxathiapane, furyl, thienyl, pyrrole, pyrazole, triazole, thiazole, oxazole, pyridine, pyrimidine, isoxazolyl, pyrazine, quinoline, isoquinoline, pyridopyrazine, pyrrolopyridine, furopyridine, indole, benzofuran, benzothiofuran, benzindole, benzoxazole, and pyrroloquinoline. Het is preferably pyridyl. in the instance where het is a nitrogen containing ring, N-substituted compounds are included. Suitable N-substituents include ($C_{1-14}$)alkyl, such as N-methyl or N-ethyl, —C(O)$C_{1-12}$alkyl, such as methylamido or ethylamido, —C(O)—O—($C_{1-14}$)alkyl, such as carbomethoxy or carboethoxy, or phenyl.

het also includes the above rings with substitution on one or more carbons. Suitable C-substituents include ($C_{1-14}$)alkyl, such as methyl or ethyl, —O$R_a$, such as methoxy and ethoxy, —S$R_a$, halo, —N($R_x$)$_2$ and the like.

Aryl includes phenyl and naphthyl substituents.

A "heteroaryl" group is mono-, bi- or tri-cyclic, and comprises 3-24, preferably 4-16 ring atoms, and is most preferably mono-cyclic comprising 5-7 ring atoms, wherein at least one or more, preferably one to four ring carbons are replaced by a heteroatom selected from O, N or S such as azirinyl, imidazolyl, thienyl, furyl, indolyl, pyranyl, thiopyranyl, thianthrenyl, isobenzofuranyl, benzofuranyl, 2H-pyrrolyl, pyrrolyl, benzimidazolyl, pyrazolyl, pyrazinyl, thiazolyl, isothiazolyl, dithiazolyl, oxazolyl, isoxazolyl, pyridyl, pyrazinyl, pyrimidinyl, pyridazinyl, indolizinyl, isoindolyl, 3H-indolyl, benzimidazolyl, benzothiazolyl and benzo[1,2, 5] thiadiazolyl, thiacumaryl, indazolyl, triazolyl, tetrazolyl, purinyl, 4H-quinolizinyl, isoquinolyl, quinolyl, benzofuranyl, dibenzofuranyl, benzothiophenyl, dibenzothiophenyl, phthalazinyl, naphthyridinyl, quinoxalyl, quinazolinyl, cinnolinyl, pteridinyl, carbazolyl, carbolinyl, phenanthridinyl, acridinyl, perimidinyl, phenanthrolinyl, furazanyl, phenazinyl, phenothiazinyl, phenoxazinyl, chromenyl, isochromanyl and chromanyl, each of these radicals being unsubstituted or substituted by one to two substituents.

"Heterocyclic" refers to a heterocyclic radical containing 1-4 heteroatoms selected from nitrogen, oxygen and sulfur (e.g. piperazinyl, lower alkyl-piperazinyl, azetidinyl, pyrrolidinyl, piperidino, morpholinyl, imidazolinyl). The heterocyclic radical is preferably unsaturated, saturated or partially saturated in the bonding ring; has 3-24, more preferably 4-16 ring atoms, wherein at least in the bonding ring one or more, preferably 1-4, especially one or two carbon ring atoms are replaced by a heteroatom selected from the group consisting of nitrogen, oxygen and sulfur, the bonding ring preferably having 4-12, especially 4-7 ring atoms; the heterocyclic radical is unsubstituted or substituted by one or more, especially 1-4 substituents and is especially selected from the group consisting of indoly, tetrahyrofuranyl, benzofuranyl, thienyl, pyridyl, imidazolinyl, morpholinyl, thiomorpholinyl, piperazinyl, piperidino, piperidyl, pyrrolidinyl, oxiranyl, 1,2-oxathiolanyl, pyrrolinyl, imidazolidinyl, pyrazolidinyl and azetidinyl, with piperazinyl being especially preferred.

In view of the close relationship between the novel compounds in free form and in the form of their salts, including those salts that can be used as intermediates, for example in the purification or identification of the novel compounds, hereinbefore and hereinafter any reference to the free compounds is to be understood as referring also to the corresponding salts, as appropriate and expedient.

Salts are especially the pharmaceutically acceptable salts of compounds of formula I.

Salts of the compounds of formula I may be pharmaceutically acceptable acid or base addition salts with organic or inorganic acids or bases. Although the preferred acid addition salts are those of hydrochloric and methanesulfonic acid, for example, salts of sulfuric, phosphoric, citric, fumaric, maleic, benzoic, benzenesulfonic, succinic, tartaric, lactic and acetic acid may also be utilized.

Preferably, $R_2$, $R_3$, $R_4$ and $R_5$ are in the relative stereochemical conformation to each other depicted in stereochemical formulae Ia and Ib:

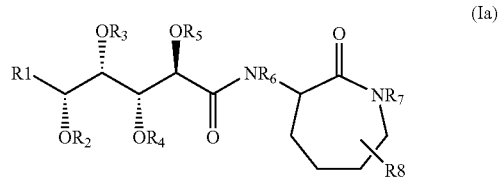

(Ia)

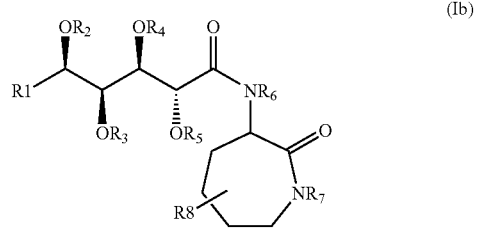

(Ib)

The lactams of formula I may be prepared as depicted below:

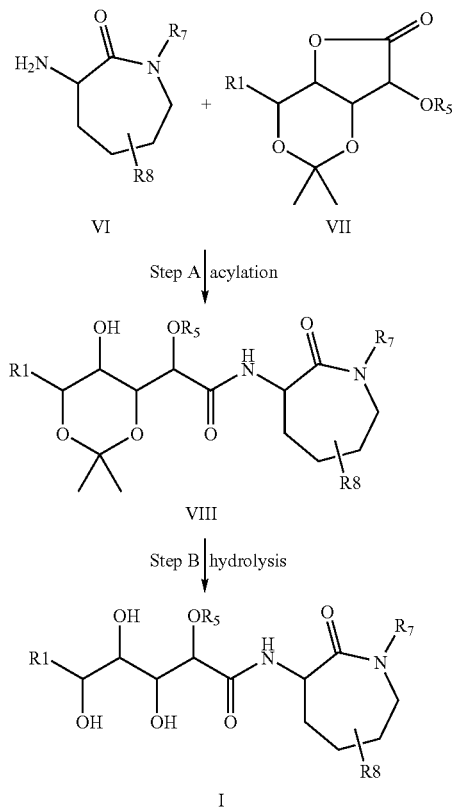

where each of $R_1$, $R_5$, $R_7$ and $R_8$ is as defined above.

As to the individual steps, Step A involves the acylation of an aminolactam of formula VI with a lactone compound of formula VII to obtain a diamide compound of formula VIII. The acylation is conducted in a polar, organic solvent, preferably a protic polar solvent such as isopropanol, at a temperature slightly below or at the reflux temperature of the solvent employed for a period of between 4 and 48 hours.

Alternatively, the acylation of an aminolactam of formula VI, or an acid addition salt thereof, with the lactone compound of formula VII in Step A may be carried out with in the presence of: 1) a weak base, preferably a carboxylate salt such as sodium 2-ethylhexanoate, and 2) a polar, organic solvent, preferably an ether such as tetrahydrofuran, at a temperature of between 0° C. and 50° C. preferably at 25° C., for a period of between 1 hour and 7 days, preferably for 20 hours.

Step B concerns the hydrolysis of the 1,3-dioxane group common to a diamide compound of formula VIII, to obtain a substituted lactam compound of formula I. The hydrolysis is typically carried out by dissolving the diamide in a mixture of solvents consisting of 1) a protic acid, preferably an organic acid such as trifluoroacetic acid, 2) a protic solvent, preferably water, and 3) an inert organic solvent, preferably a cyclic ether such as tetrahydrofuran, at a temperature of between 0° C. and 25° C. for a period of between 5 minutes and 2 hours.

Alternatively, the diamide compounds of formula VIIIa may be prepared according to the following 3-step reaction scheme:

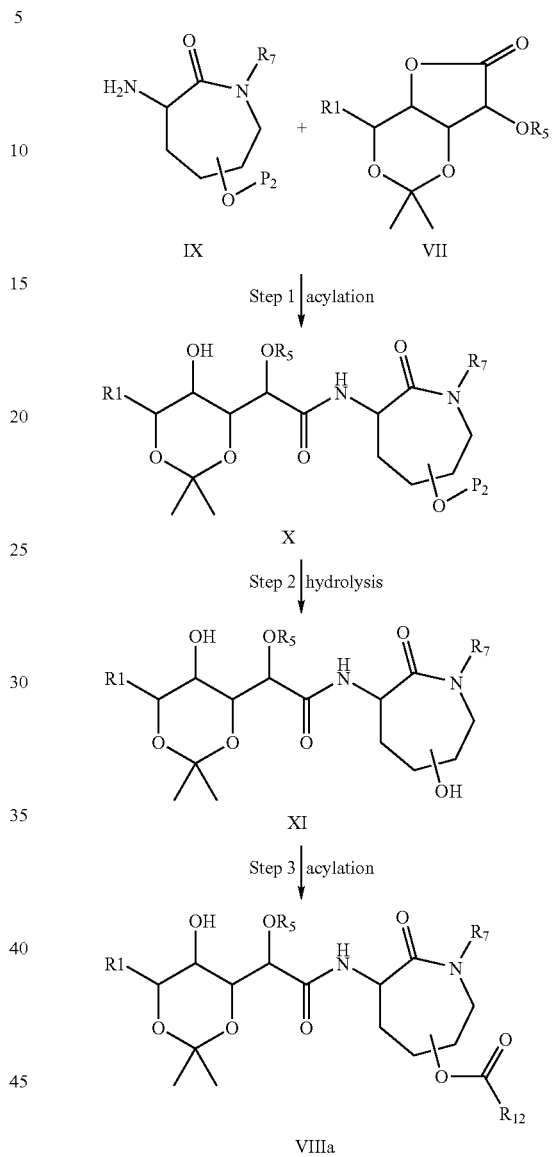

where $R_1$, $R_5$, and $R_7$ are as defined above, $R_{12}$ is an appropriate substituent based on the definition of R8 above, and $P_2$ is an alcohol protective group. Preferably, $P_2$ is a silyl group such as tert-butyldimethylsilyl.

As to the individual steps, Step 1 involves the acylation of an aminolactam of formula IX with a lactone compound of formula VII to obtain a diamide compound of formula X. The acylation is conducted in the presence of a base, preferably an alkylamine base such as diisopropylethylamine, and a polar, organic solvent, preferably a protic polar solvent such as isopropanol, at a temperature slightly below or at the reflux temperature of the solvent employed for a period of between 4 and 48 hours.

Step 2 concerns the hydrolysis of the group $P_2$ common to a diamide compound of formula X to obtain a hydroxylactam compound of formula XI. The hydrolysis is typically carried out in the presence of fluoride, preferably a fluoride salt such as tetrabutyl-ammonium fluoride, and an inert organic solvent, preferably a cyclic ether such as tetrahydrofuran, at a temperature of between 0° C. and 25° C. for a period of between 5 minutes and 2 hours.

Step 3 concerns the acylation of a hydroxylactam compound of formula XI by reacting it with an acid chloride of formula $R_{12}COCl$ where $R_{12}$, is defined above, to obtain a diamide compound of formula VIIIa. The acylation is conducted in the presence of a base, preferably an alkylamine base such as triethylamine, and an inert organic solvent, preferably a chlorinated alkane such as dichloromethane, at a temperature of between −78° C. and 25° C. for a period of between 1 and 24 hours.

Alternatively, the acylation of a hydroxylactam compound of formula XI in Step 3 may be carried out with a carboxylic acid of formula $R_{12}COCl$ where $R_{12}$, is defined above, in the presence of a carboxylic acid coupling reagent, preferably a diimide such as 1-(3-dimethylaminopropyl)-3-ethylcarbodiimide hydrochloride, and a suitable activating agent common to diimide coupling reactions, preferably a substituted pyridine such a 4-dimethylaminopyridine, and an inert organic solvent, preferably a chlorinated alkane such as dichloromethane, at a temperature of between −78° C. and 25° C. for a period of between 1 and 24 hours.

The aminolactam compounds of formula Ia may be prepared as depicted below:

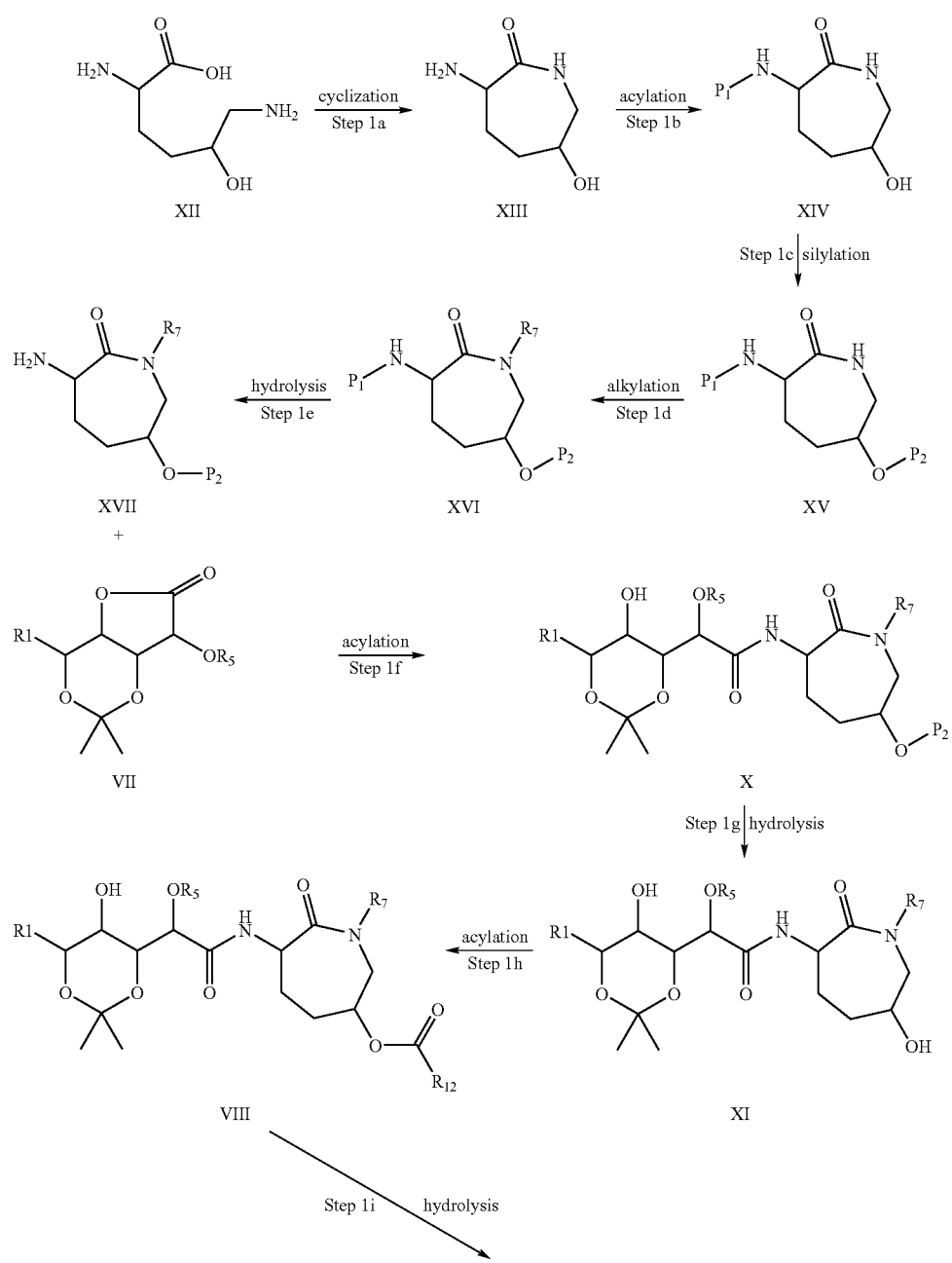

-continued

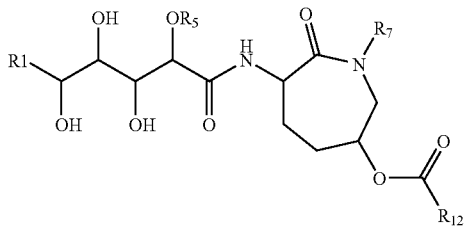

IIa where each $R_1$, $R_5$, $R_7$ and $R_{12}$ is as defined above, and $P_1$ is a carbonyl-containing group. Preferably, $P_1$ is alkoxycarbonyl such as t-butyloxycarbonyl. $P_2$ is an alcohol protective group. Preferably, $P_2$ is a silyl group such as tert-butyldimethylsilyl.

As to the individual steps, Step 1a involves the cyclization of hydroxylysine (or any salt or hydrate preparation thereof) XII to obtain hydroxycyclolysine XIII. The cyclization is typically carried out in the presence of a coupling reagent, preferably a diimide such as 1-(3-dimethylaminopropyl)-3-ethylcarbodiimide hydrochloride, and a suitable activating agent common to diimide coupling reactions, preferably an N-hydroxy compound such as 1-hydroxybenztriazole hydrate, and a base, preferably an alkylamine base such as triethylamine, and a polar organic solvent, preferably an amide such as N,N-dimethylformamide, at a temperature of between 0° C. and 40° C. for a period of between 12 and 72 hours.

Step 1b involves the N-acylation of hydroxycyclolysine XIII to obtain an N-acylhydroxycyclolysine compound of formula XIV. The acylating agent is typically an acid chloride or an anhydride. When $P_1$ is t-butyloxycarbonyl, the acylating agent is di-tert-butyldicarbonate. The reaction is carried out in the presence of a base, preferably an alkylamine base such as triethylamine, and a polar organic solvent, preferably an amide such as N,N-dimethylformamide, at a temperature of between 0° C. and 40° C. for a period of between 1 and 24 hours.

Step 1c involves the O-silylation of an N-acylhydroxycyclolysine compound of formula XIV to obtain a silyl ether compound of formula XV. The silylating agent is typically a silyl chloride or trifluoromethanesulfonate. When $P_2$ is tert-butyldimethylsilyl, the silylating agent is tert-butyldimethylsilylchloride. The reaction is carried out in the presence of a base, preferably a mild base such as imidazole, and a polar organic solvent, preferably an amide such as N,N-dimethylformamide, at a temperature of between 0° C. and 40° C. for a period of between 1 and 24 hours.

Step 1d involves the N-alkylation of a silyl ether compound of formula XV with an alkyl (defined as $R_7$ above) halide or sulfonate to obtain an N-alkyl lactam compound of formula XVI. The alkylation is conducted in the presence of a strong base, preferably an alkali metal amide such as sodium bis(trimethylsilyl)amide, and an inert organic solvent, preferably a cyclic ether such as tetrahydrofuran, at a temperature of between –100° C. and 25° C. for a period of between 5 minutes and 2 hours.

Step 1e concerns the hydrolysis of the group $P_1$ on an N-alkyl lactam compound of formula XVI. The hydrolysis is typically carried out in the presence of a protic acid, preferably an organic acid such as trifluoroacetic acid, hydrogen or a silyl halide, preferably a silyl iodide such as trimethylsilyl iodide, and an inert organic solvent, preferably a chlorinated alkane such as dichloromethane, at a temperature of between –100° C. and 25° C. for a period of between 1 minute and 2 hours.

Step 1f involves the acylation of an aminolactam of formula XVII with a lactone compound of formula VII to obtain a diamide compound of formula X. The acylation is conducted in the presence of a base, preferably an alkylamine base such as diisopropylethylamine, and a polar, organic solvent, preferably a protic polar solvent such as isopropanol, at a temperature slightly below or at the reflux temperature of the solvent employed for a period of between 4 and 48 hours.

Step 1g concerns the hydrolysis of the group $P_2$ common to an N-alkyl lactam compound of formula X, to obtain a hydroxylactam compound of formula XI. The hydrolysis is typically carried out in the presence of fluoride, preferably a fluoride salt such as tetrabutylammonium fluoride, and an inert organic solvent, preferably a cyclic ether such as tetrahydrofuran, at a temperature of between 0° C. and 25° C. for a period of between 5 minutes and 6 hours.

Step 1h concerns the acylation of a hydroxylactam compound of formula XI by reacting it with an acid chloride of formula $R_{12}COCl$ where $R_{12}$, is defined above, to obtain a diamide compound of formula VIII. The acylation is conducted in the presence of a base, preferably an alkylamine base such as triethylamine, and an inert organic solvent, preferably a chlorinated alkane such as dichloromethane, at a temperature of between –78° C. and 25° C. for a period of between 1 and 24 hours.

Step 1i concerns the hydrolysis of the 1,3-dioxane group of compound formula VIII, to obtain a substituted lactam compound of formula I. The hydrolysis is typically carried out by dissolving the diamide in a mixture of solvents consisting of 1) a protic acid, preferably an organic acid such as trifluoroacetic acid, 2) a protic solvent, preferably water, and 3) an inert organic solvent, preferably a cyclic ether such as tetrahydrofuran, at a temperature of between 0° C. and 25° C. for a period of between 5 minutes and 2 hours.

Alternatively, the acylation of a hydroxylactam compound of formula XI in Step 1h may be carried out with a carboxylic acid of formula $R_{12}COOH$ where $R_{12}$, is defined, in the presence of a carboxylic acid coupling reagent, preferably a diimide such as 1-(3-dimethylaminopropyl)-3-ethylcarbodiimide hydrochloride, and a suitable activating agent common to diimide coupling reactions, preferably a substituted pyridine such a 4-dimethylaminopyridine, and an inert organic solvent, preferably a chlorinated alkane such as dichloromethane, at a temperature of between –78° C. and 25° C. for a period of between 1 and 24 hours.

The aminolactam compounds of formula IIb may be prepared as depicted below:

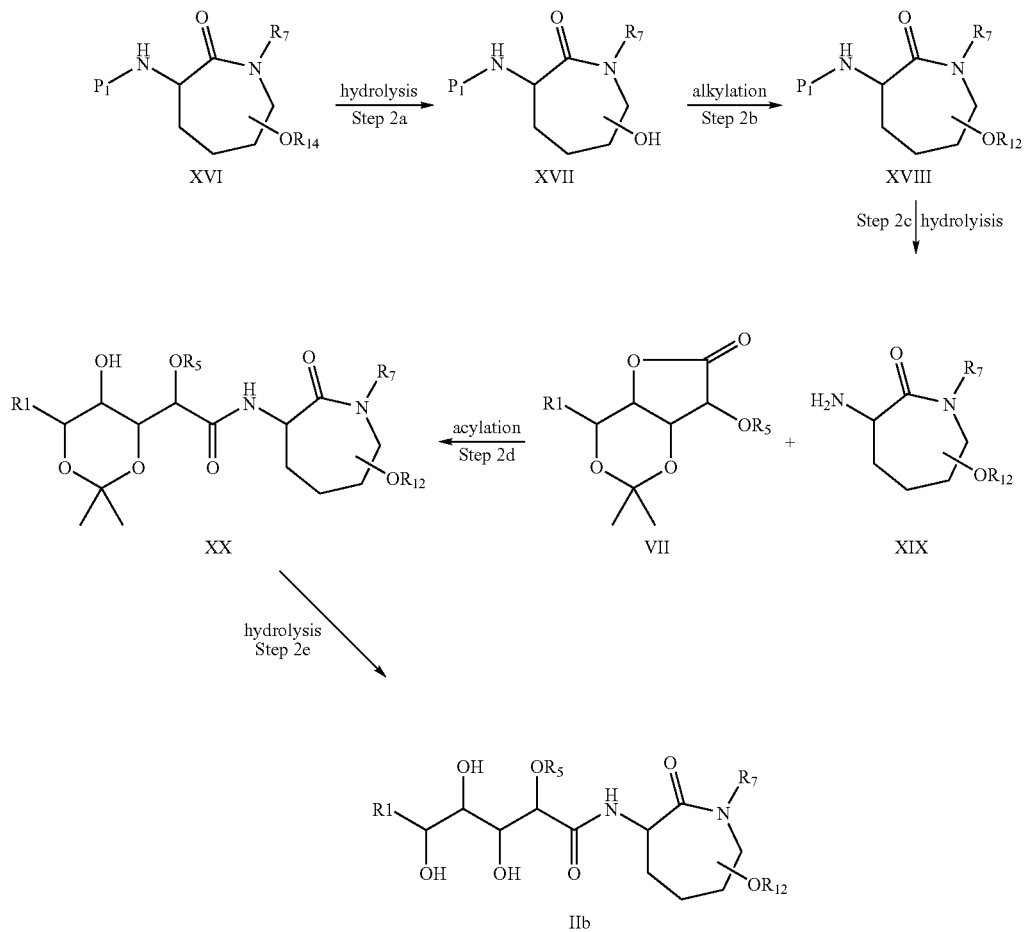

$R_{14}$ is a leaving group.

where each R1, $R_5$, $R_7$ and $R_{12}$ is as defined above, and $P_1$ is a carbonyl-containing group. Preferably, $P_1$ is alkoxycarbonyl such as t-butyloxycarbonyl. $P_2$ is an alcohol protective group. Preferably, $P_2$ is a silyl group such as tert-butyldimethylsilyl.

Step 2a concerns the hydrolysis of the group $P_2$ common to an N-alkyl lactam compound of formula XVI, to obtain a hydroxylactam compound of formula XVII. The hydrolysis is typically carried out in the presence of fluoride, preferably a fluoride salt such as tetrabutylammonium fluoride, and an inert organic solvent, preferably a cyclic ether such as tetrahydrofuran, at a temperature of between 0° C. and 25° C. for a period of between 5 minutes and 6 hours.

Step 2b involves the O-alkylation of a compound of formula XVII with an alkyl (defined as $R_{12}$ above) halide or sulfonate to obtain an O-alkyl lactam compound of formula XVI. The alkylation is conducted in the presence of a strong base, preferably an alkali metal amide such as sodium bis(trimethylsilyl)amide, and an inert organic solvent, preferably a cyclic ether such as tetrahydrofuran, at a temperature of between –100° C. and 25° C. for a period of between 5 minutes and 6 hours.

Step 2c concerns the hydrolysis of the group $P_1$ on an N-alkyl lactam compound of formula XVIII. The hydrolysis is typically carried out in the presence of a protic acid, preferably an organic acid such as trifluoroacetic acid, hydrogen or a silyl halide, preferably a silyl iodide such as trimethylsilyl iodide, and an inert organic solvent, preferably a chlorinated alkane such as dichloromethane, at a temperature of between –100° C. and 25° C. for a period of between 1 minute and 2 hours.

Step 2d involves the acylation of an aminolactam of formula XIX with a lactone compound of formula VII to obtain a diamide compound of formula XX. The acylation is conducted in the presence of a base, preferably an alkylamine base such as diisopropylethylamine, and a polar, organic solvent, preferably a protic polar solvent such as isopropanol, at a temperature slightly below or at the reflux temperature of the solvent employed for a period of between 4 and 48 hours.

Step 2e concerns the hydrolysis of the 1,3-dioxane group of compound formula XX, to obtain a substituted lactam compound of formula I. The hydrolysis is typically carried out by dissolving the diamide in a mixture of solvents consisting of 1) a protic acid, preferably an organic acid such as trifluoroacetic acid, 2) a protic solvent, preferably water, and 3) an inert organic solvent, preferably a cyclic ether such as tetrahydrofuran, at a temperature of between 0° C. and 25° C. for a period of between 5 minutes and 2 hours.

The aminolactam compounds of formula IIc may be prepared as depicted below:

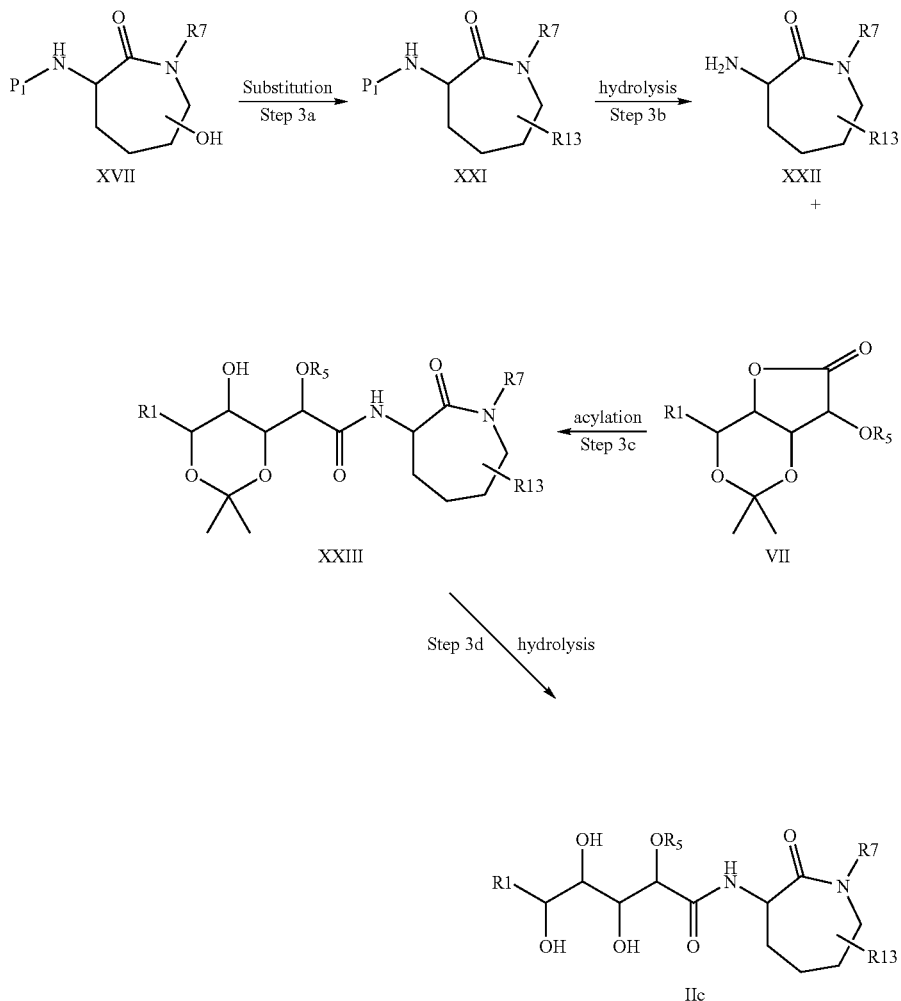

where each R1, R$_5$, R7 is as defined above, R13 is an appropriate substituent based on the definition of R$_8$ above and P$_1$ is a carbonyl-containing group.

Preferably, P$_1$ is alkoxycarbonyl such as t-butyloxycarbonyl.

Step 3a involves the substitution of the hydroxy group of the compound of formula XVII for a heteroatom (defined as Y above) preferably with inversion of configuration and most preferably by a Mitsunobu type reaction (reference) involving a trialkyl or triaryl substituted phosphine, an azodicarboxylate diester and a nucleophile source such as diphenylphosphoryl azide. Alternatively the hydroxy group can be converted to a sulfonate or halide suitable for displacement.

Step 3b concerns the hydrolysis of the group P$_1$ on an N-alkyl lactam compound of formula XXI. The hydrolysis is typically carried out in the presence of a protic acid, preferably an organic add such as trifluoroacetic acid, hydrogen or a silyl halide, preferably a silyl iodide such as trimethylsilyl iodide, and an inert organic solvent, preferably a chlorinated alkane such as dichloromethane, at a temperature of between −100° C. and 25° C. for a period of between 1 minute and 2 hours.

Step 3c involves the acylation of an aminolactam of formula XXII with a lactone compound of formula VII to obtain a diamide compound of formula XXIII. The acylation is conducted in the presence of a base, preferably an alkylamine base such as diisopropylethylamine, and a polar, organic solvent, preferably a protic polar solvent such as isopropanol, at a temperature slightly below or at the reflux temperature of the solvent employed for a period of between 4 and 48 hours.

Step 3d concerns the hydrolysis of the 1,3-dioxane group of compound formula XXIII, to obtain a substituted lactam compound of formula I. The hydrolysis is typically carried out by dissolving the diamide in a mixture of solvents consisting of 1) a protic acid, preferably an organic acid such as trifluoroacetic acid, 2) a protic solvent, preferably water, and 3) an inert organic solvent, preferably a cyclic ether such as tetrahydrofuran, at a temperature of between 0° C. and 25° C. for a period of between 5 minutes and 2 hours.

The aminolactam compounds of formula lid may be prepared as depicted below:

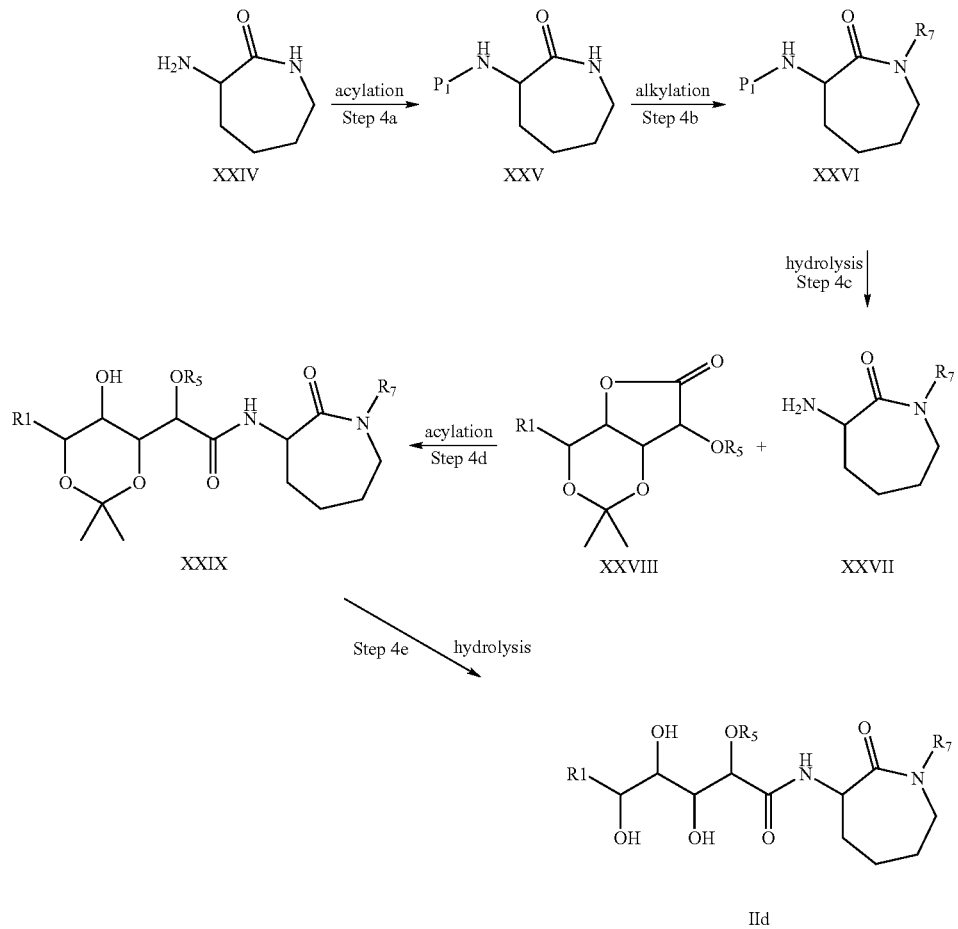

where each R1, $R_5$, and $R_7$ is as defined above, and $P_1$ is a carbonyl-containing group. Preferably, $P_1$ is alkoxycarbonyl such as t-butyloxycarbonyl.

Step 4a involves the N-acylation of cyclolysine XXIV to obtain an N-acylcyclolysine compound of formula XXV. The acylating agent is typically an acid chloride or an anhydride. When $P_1$ is t-butyloxycarbonyl, the acylating agent is di-tert-butyldicarbonate. The reaction is carried out in the presence of a base, preferably an alkylamine base such as triethylamine, and a polar organic solvent, preferably an amide such as N,N-dimethylformamide, at a temperature of between 0° C. and 40° C. for a period of between 1 and 24 hours.

Step 4b involves the N-alkylation of an N-acylcyclolysine compound of formula XXV with an alkyl (defined as $R_7$ above) halide or sulfonate to obtain an N-alkyl lactam compound of formula XXVI. The alkylation is conducted in the presence of a strong base, preferably an alkali metal amide such as sodium bis(trimethylsilyl)amide, and an inert organic solvent, preferably a cyclic ether such as tetrahydrofuran, at a temperature of between –100° C. and 25° C. for a period of between 5 minutes and 2 hours.

Step 4c concerns the hydrolysis of the group $P_1$ on an N-alkyl lactam compound of formula XXVI, The hydrolysis is typically carried out in the presence of a protic acid, preferably an organic acid such as trifluoroacetic acid, hydrogen or a silyl halide, preferably a silyl iodide such as trimethylsilyl iodide, and an inert organic solvent, preferably a chlorinated alkane such as dichloromethane, at a temperature of between –100° C. and 25° C. for a period of between 1 minute and 2 hours.

Step 4d involves the acylation of an aminolactam of formula XVII with a lactone compound of formula XXVII to obtain a diamide compound of formula XXIX. The acylation is conducted in the presence of a base, preferably an alkylamine base such as diisopropylethylamine, and a polar, organic solvent, preferably a protic polar solvent such as isopropanol, at a temperature slightly below or at the reflux temperature of the solvent employed for a period of between 4 and 48 hours.

Step 4e concerns the hydrolysis of the 1,3-dioxane group of compound formula XXIX, to obtain a substituted lactam compound of formula Id. The hydrolysis is typically carried out by dissolving the diamide in a mixture of solvents consisting of 1) a protic acid, preferably an organic acid such as trifluoroacetic acid, 2) a protic solvent, preferably water, and 3) an inert organic solvent, preferably a cyclic ether such as tetrahydrofuran, at a temperature of between 0° C. and 25° C. for a period of between 5 minutes and 2 hours.

The lactone compounds of formula VII may be prepared as depicted below:

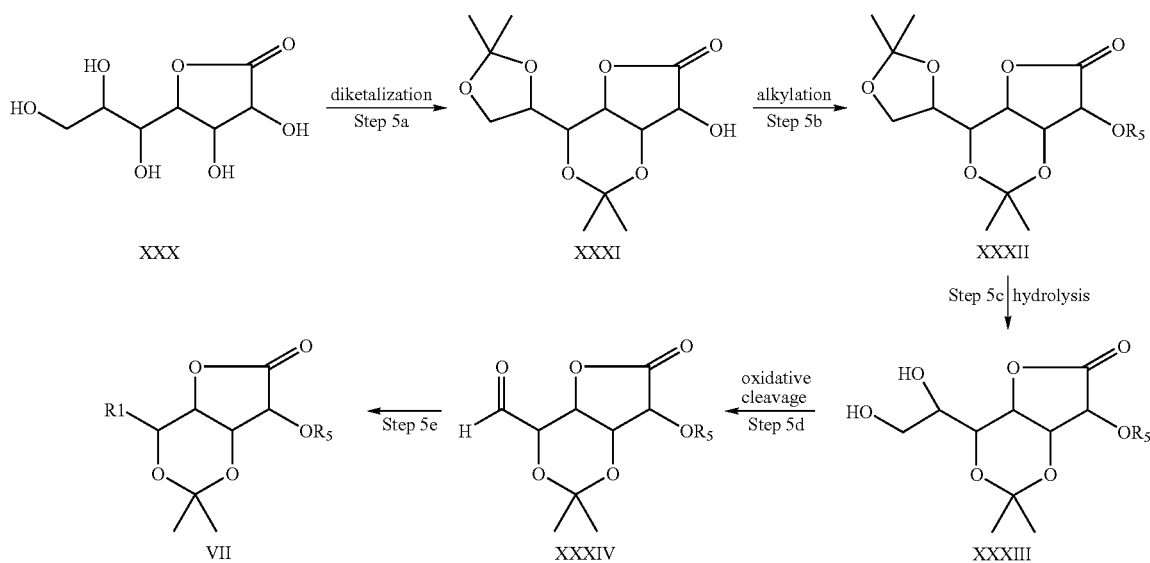

where R1 and R5 are as defined above.

As to the individual steps, Step 5a involves the diketalization of polyhydroxylated lactone of formula XXX with acetone to obtain bis(acetonide) XXXI. The diketalization is conducted in acetone as solvent using a catalyst such as iodine at a temperature of between 0° C. and the reflux temperature for a period of between 2 and 48 hours.

Step 5b involves the alkylation of bis(acetonide) XXXI with an alkylating agent such as an alkyl (defined as $R_5$ above) halide, sulfonate or sulfate ester to obtain the ether XXXII. The alkylation is conducted in the presence of water and a base, preferably a metal oxide such as silver oxide, and an inert organic solvent, preferably a chlorinated alkane such as dichloromethane, at a temperature of between 0° C. and the reflux temperature for a period of between 12 hours and 7 days.

Step 5c involves the hydrolysis of alkyl ether XXXII to obtain the dihydroxy compound of formula XXXIII. The hydrolysis is conducted in the presence of water and a protic acid, preferably a carboxylic acid such as acetic acid, at a temperature of between 5° C. and 35 C. for a period of between 1 and 24 hours.

Step 5d involves the oxidative cleavage of dihydroxy compound XXXIII to obtain the aldehyde XXXIV. The reaction is conducted in the presence of an oxidant, preferably a periodate salt such as sodium periodate, in a protic solvent, preferably an alkanol such as methanol, at a temperature of between 0° C. and 25° C. for a period of between 10 minutes and 4 hours.

Step 5e involves the olefination of aldehyde XXXIV to obtain a lactone compound of formula VII. The olefination is conducted in the presence of an organometallic compound, preferably an organochromium compound such as the transient species generated from chromium(II)chloride and a diiodoalkane (defined as $R_1CHI_2$ where $R_1$ is as defined above), in the presence of a solvent mixture consisting of 1) a polar organic solvent, preferably an amide such as N,N-dimethylformamide, and 2) an inert organic solvent, preferably a cyclic ether such as tetrahydrofuran, at a temperature of between −80° C. and 25° C. for a period of between 5 minutes and 4 hours.

Alternatively the lactone compounds of formula VIIa may be prepared as depicted below:

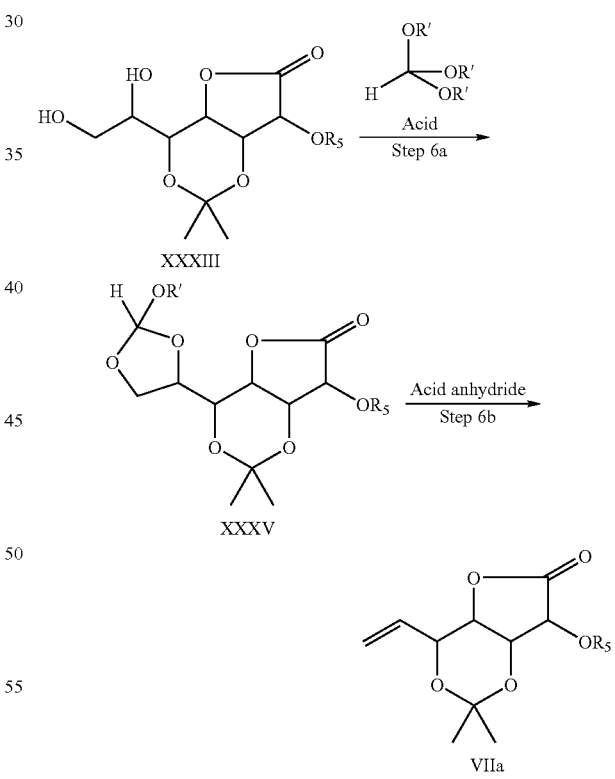

where $R_5$ is defined above and R' is $C_{(1-6)}$ alkyl

Step 6a involves the conversion of XXXIII to an ortho ester XXXV by acid catalyzed transesterification with an alkyl orthoester, preferably triethylorthoformate and p-toluenesulfonic acid. The reaction can be run with excess alkyl orthoester as the solvent or an inert organic solvent may be used at a temperature of between 20° C. and 80° C. for a period between 1 and 24 hours.

Step 6b involves the elimination of the orthoester XXXV to give alkene VIIa. The reaction is conducted in an organic acid anhydride, preferably acetic anhydride at a temperature of 20° C. and 100 ° C. for a period between 1 and 24 hours.

Alternatively the lactams of formula I may be prepared as depicted below:

When P$_2$ is tert-butyldimethylsilyl, the silylating agent is tert-butyldimethylsilylchloride. The reaction is carried out in the presence of a base, preferably a mild base such as imidazole, and a polar organic solvent, preferably an amide such as N,N-dimethylformamide, at a temperature of between 0° C. and 40° C. for a period of between 1 and 24 hours.

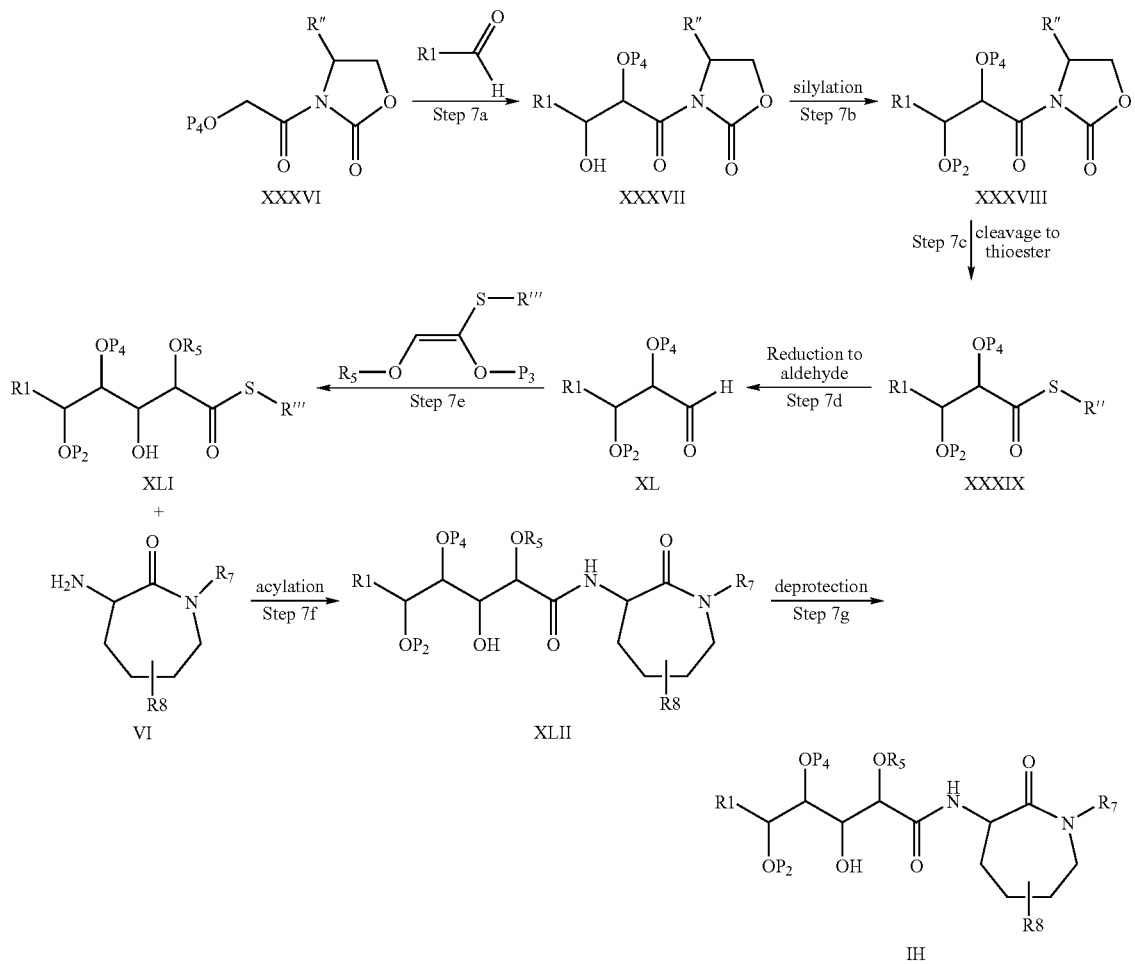

where each R1, R$_7$, R$_9$, and X are defined above, R″ is a C$_{(3-9)}$ branched alkyl or phenyl substituted C$_{(1-3)}$ alkyl, preferably benzyl and R‴ is a C$_{(1-6)}$ alkyl, preferably ethyl. P$_2$ and P$_3$ are alcohol protective groups, preferably silyl groups such as tert-butyldimethylsilyl and trimethylsilyl respectively. P$_4$ is an alcohol protective group, preferably benzyl or 2-naphthlmethyl ethers.

Step 7a involves an Evans type aldol condensation of oxyimide XXXVI with an aldehyde to give XXXVII. The reaction is conducted in the presence of a Lewis acid, preferably diethylborontriflate and an organic base, preferably diisopropylethylamine in an inert organic solvent such as CH$_2$Cl$_2$ at a temperature of between −100° C. and 0° C. for a period of 1-24 hours.

Step 7b involves the O-silylation of compound XXXVII to obtain a silyl ether compound of formula XXXVIII. The silylating agent is typically a silyl chloride or trifluoromethanesulfonate.

Step 7c involves the formation of thioester XXXIX from XXXVIII by reaction with an alkali metal salt of a thioester, preferably LiSEt, in an inert solvent, preferably THF, at a temperature of between −100° C. and 0° C. for a period of 1-24 hours.

Step 7d involves conversion of thioester XXXIX to the aldehyde XL by reduction with a metal hydride, preferably diisobutylaluminum hydride, in an inert solvent, preferably CH$_2$Cl$_2$, at a temperature of between −100° C. and 0° C. for a period of 10 minutes to 1 hour.

Step 7e involves a Gennari type coupling of aldehyde XL with a thiovinylether to give the thioester XLI. The reaction is conducted in the presence of a Lewis acid, preferably SnCl$_4$, in an inert solvent, preferably a mixture of CH$_2$Cl$_2$ and heptane, at a temperature of between −100° C. and 0° C. for a period of 1-24 hours.

Step 7f involves the acylation of thioester XLI with amine VI to give diamide XLII. The reaction is conducted in an inert solvent, preferably dioxane, at a temperature of between room temperature and 100° C. for a period of 1-48 hours.

Step 7g involves the deprotection of diamide XLII to give compound I. The method employed is dependant on the $P_2$ and $P_5$ groups utilized, preferably when $P_2$ is tert-butyldimethylsilyl and $P_4$ is 2-naphthlmethyl ether a two step procedure is employed using DDQ in a mixture of wet $CH_3OH$ and $CH_2Cl_2$ followed by treatment with tetrabutylammonium fluoride in THF to give compound I.

The following specific examples are intended to further illustrate, but not limit, the invention.

EXAMPLES

Example 1

Tetradecanoic acid (3R,6S)-7-oxo-1-pyridin-3-ylmethyl-6-((2R,3R,4S,5R)-(E)-3,4,5-trihydroxy-2-methoxy-8,8-dimethyl-non-6-enoylamino)azepan-3-yl ester

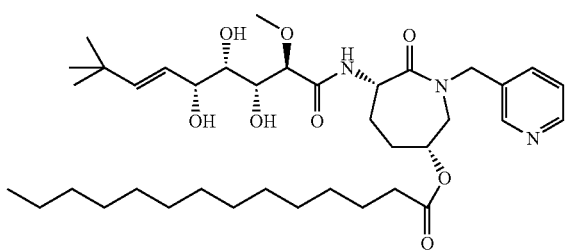

a) Preparation of 3,5:6,7-bis-O-(1-methylethylidene)-α-D-glucoheptonic γ-lactone α-D-Glucoheptonic γ-lactone (500 g, 2.4 mol) is added into 9 L of acetone in a 5 gal plastic drum. The mixture is agitated mechanically until most of the solid dissolved (15-20 min). Iodine (60 g, 0.236 mol) is added portion wise into the lactone solution over 5-10 min. The resulting mixture is stirred overnight. A saturated solution of $Na_2S_2O_3$ (1.3 L) is added to the iodine solution to quench the reaction. The resulting solution is concentrated to about half of its original volume in vacuum, and brine solution (5 L) is added. The resulting mixture is extracted with 3×1.2 L EtOAc. All organic layers are combined and evaporated to dryness. The solid is slurried with a mixture of ether and hexane (3:7), and filtered. The filter cake is washed with $Et_2O$ (50 mL) and air dried, giving 599 g of the desired compound as a white powder (86.5%): $^1$H NMR (CDCl$_3$) δ 4.62 (m, 1H), 4.50 (m, 1H), 4.35 (m, 2H), 4.07 (m, 1H), 3.93 (m, 1H), 3.82 (dd, 1H), 3.08 (d, 1H), 1.51 (s, 3H), 1.44 (s, 3H), 1.39 (s, 3H), 1.35 (s, 3H); $^{13}$C NMR (CDCl$_3$) δ 174.4, 109.4, 98.6, 72.8, 71.4, 69.3, 68.4, 67.8, 66.7, 28.6, 26.7, 24.6, 19.3.

Preparation of 2-O-methyl-3,5:6,7-bis-O-(1-methylethylidene)-α-D-glucoheptonic γ-lacton 3,5:6,7-bis-O-(1-methylethylidene)-α-D-glucoheptonic γ-lactone (719 g, 2.49 mol) is added into 4.5 L of $CH_2Cl_2$ in a 5 gal plastic drum. The mixture is stirred under $N_2$. Iodomethane (2500 g, 17.6 mol) is added immediately followed by addition of silver(I) oxide (1750 g, 7.58 mol). Water (30 mL) is added to the reaction mixture. Ice bath is used to maintain the reaction temperature at 15-30° C. The reaction is stirred in the absence of light for 18 h. After diluting the reaction mixture with 1.5 L of $CH_2Cl_2$, the solid is filtered and washed with an additional 2.2 L of $CH_2Cl_2$. The undesired solid is discarded and the filtrate is evaporated to dryness. The residue is slurried in $Et_2O$ (1.5 L), filtered, and dried to give 618 g product (82%): $^1$H NMR (CDCl$_3$) δ 4.75 (m, 1H), 4.33 (m, 1H), 4.29 (m, 1H), 4.15 (m, 1H), 4.07 (m, 1H), 3.96 (dd, 1H), 3.83 (dd, 1H), 3.65 (s, 3H), 1.57 (s, 3H), 1.42 (s, 6H), 1.35 (s, 3H); $^{13}$C NMR (CDCl$_3$) δ 172.5, 109.6, 98.5, 79.0, 73.1, 69.5, 68.6, 67.5, 66.9, 59.1, 28.9, 26.9, 24.9, 19.4.

Preparation of 2-O-Methyl-3,5-O-(1-methylethylidene)-α-D-glucoheptonic γ-lactone 2-O-methyl-3,5:6,7-bis-O-(1-methylethylidene)-α-D-glucoheptonic γ-lactone (618 g, 2.05 mol) is dissolved in 8 L of a mixture of acetic acid and water (1:1) over 30 min. The solution is stirred at ambient temperature overnight. The solution is evaporated to dryness in vacuum. The solid is slurried in 3-5 L of hot acetone and filtered. After oven drying at 20-30° C., 363 g of the desired compound is obtained (67.6%). $^1$H NMR(CDCl$_3$): δ 4.92 (d, 1H), 4.80 (m, 1H), 4.47 (d, 1H), 4.42 (t, 1H), 4.39 (m, 1H), 3.95 (dd, 1H), 3.75 (m, 2H), 3.4 (s, 3H), 2.5 (m, 1H), 1.42 (s, 3H), 1.22 (s, 3H).

d) Preparation of 2,4-O-(1-methylethylidene-5-O-methyl-L-glucuronic γ-lactone

2-O-Methyl-3,5-O-(1-methylethylidene)-α-D-glucoheptonic γ-lactone (200 g, 0.76 mol) is dissolved into a 1:1 mixture of methanol and water (3.6 L). The stirred mixture is cooled in an ice water bath to about 8° C. Solid $NaIO_4$ (213 g, 0.98 mol) is added portion wise. Reaction is complete within 40 min as indicated by thin layer chromatography (TLC) (silica gel, 5% methanol, 15% EtOAc in $CH_2Cl_2$). Solid NaCl is added into the reaction mixture to saturate the methanolic solution. The solid is filtered and washed with 2 L $CH_2Cl_2$. The filtrate is extracted with 7×500 mL $CH_2Cl_2$. Combined organic layers are dried over $Na_2SO_4$, filtered and concentrated to a syrup, which formed a precipitate upon addition of hexane. The solid is filtered and rinsed with $Et_2O$. A portion of the crude product (50 g) is dissolved in 3 L $CHCl_3$ and heated to reflux. After rotary evaporation of 2.1 L of $CHCl_3$ at atmospheric pressure (methanol is driven out of the system by co-evaporation with $CHCl_3$) the residue is evaporated to dryness. 44 g of the desired product is obtained as a solid after drying in vacuum overnight. $^1$H NMR (CDCl$_3$): δ 9.60 (s, 1H), 4.78 (m, 1H), 4.42 (s, 2H), 4.15 (dd, 1H), 3.65 (s, 3H), 1.58 (s, 3H), 1.55 (s, 3H); $^{13}$C NMR (CDCl$_3$) δ 198.8, 171.9, 99.0, 78.4, 74.4, 72.9, 68.4, 67.4, 59.2, 28.7, 19.0.

e) Preparation of (6E)-6,7,8,9-tetradeoxy-8,8-dimethyl-2-O-methyl-3,5-O-(1-methylethylidene)-gulonon-6-enonic acid lactone Into a 2 L round bottom flask, is added $CrCl_2$ (50 g, 41 mmol), anhydrous THF (750 mL), and DMF (32 mL). The mixture is stirred under $N_2$ for 1 h. A solution of 2,4-O-(1-methylethylidene)-5-O-methyl-L-glucuronic γ-lactone (12 g, 50 mmol), 1,1-diiodo-2,2-dimethylpropane (15 mL), and 500 mL of anhydrous THF is added slowly into the reaction mixture. After the addition, the reaction mixture is stirred at ambient temperature for 1.5 h. The reaction is quenched with saturated aqueous NH₄Cl. The residue is partitioned with EtOAc/water and chromatographed (5% EtOAc-CH₂Cl₂) to give 9 g (63%) of the desired compound as a white crystalline solid: $^1$HNMR (CDCl₃) δ 5.82 (d, 1H), 5.58 (q, 1H), 4.71 (m, 1H), 4.46 (m, 1H), 4.10 (dd, 1H), 4.0 (m, 1H), 3.66 (s, 3H), 1.58 (s, 3H), 1.53 (s, 3H), 1.07 (s, 9H); $^{13}$C NMR (CDCl₃) δ 172.5, 147.0, 120.2, 98.7, 79.1, 71.9, 70.3, 67.6, 59.2, 33.2, 29.3, 19.3.

Preparation of (3S, 6R)-3-(tert-butoxycarbonyl) aminohexahydro-6-hydroxy-2H-azepin-2-one In a 1 L flask (5R)-5-hydroxy-L-lysine (10 g, 0.040 mol), 1-hydroxybenzotriazole hydrate (8.2 g, 0.060 mol) and 1-[3-(dimethylamino)propyl]-3-ethylcarbodiimide-HCl (11.6 g, 0.060 mol) are added to 500 mL DMF with stirring. After 0.5 h triethylamine (16.8 mL, 0.120 mol) is added. The reaction is stirred at room temperature for 48 h. Di-tert-butyl dicarbonate (17.6 g, 0.080 mol) and triethylamine (16.8 mL, 0.120 mol) are added. Stirring is continued for 16 h. The reaction mixture is filtered to remove triethylamine-HCl and the solvent is removed by rotary evaporation under high vacuum to give a thick oil. The oil is dissolved in 150 mL CH₂Cl₂ and applied to a silica gel column (150 g, 40×250 mm). The column is eluted with 3% methanol in CH₂Cl₂ to give the crude product as a solid. The crude solid is dissolved in 120 mL hot CH₂Cl₂ and cooled to −20° C. for 1 h. The resulting solid is filtered and washed with 50 mL CH₂Cl₂. The combined filtrates are evaporated to dryness. CH₂Cl₂ (40 mL) is added to this residue and the resulting slurry is stirred for 0.5 h at room temperature. The slurry is filtered and the solid washed with 25 mL CH₂Cl₂. The solids are combined to give 5.57 g of (3S, 6R)-3-(tert-butoxycarbonyl)aminohexahydro-6-hydroxy-2H-azepin-2-one. 300 MHz $^1$H NMR (DMSO) δ 7.42 (1 H, t, J=5.1 Hz), 6.38 (1 H, d, J=6.6 Hz), 4.60 (1 H, d, J=4.2 Hz), 4.07 (1 H, m), 3.74 (1 H, m), 3.32 (1 H, m), 3.03 (1 H, m), 1.8-1.5 (4 H, m), 1.39 (9 H, s).

g) Preparation of (3S, 6R)-3-(tert-butoxycarbonyl) aminohexahydro-6-t-butyl-dimethylsilyloxy-2H-azepin-2-one To a stirred solution of (3S, 6R)-3-(tert-butoxycarbonyl) aminohexahydro-6-hydroxy-2H-azepin-2-one (25 g, 102 mmol) in DMF (60 mL) is added tert-butyldimethylsilyl chloride (23.16 g, 153 mmol), and imidazole (10.45 g, 153 mmol). The reaction is stirred at room temperature for 18 h, diluted with 1 L of water and extracted with a 1:1 (2×200 mL) mixture of ethyl acetate and hexane. All organic layers are combined, washed with brine, dried with NaSO₄, and concentrated under vacuum. The residue is purified by recrystallization with ethyl acetate/hexane to give 28.5 g (78%) of (3S, 6R)-3-(tert-butoxycarbonyl) aminohexahydro-6-tert-butyldimethylsilyloxy-2H-azepin-2-one as a white solid, melting point: 65-66° C.; $^1$H NMR (CDCl₃) δ 5.86 (d, J=6 Hz, 1H), 5.58 (t, J=6 Hz, 1H), 4.18 (m, 1H), 3.91 (s, 1H), 3.35(dd, J=6 Hz and 16 Hz, 1H), 3.07 (m, 1H), 1.80 (m, 4H), 1.40 (s, 9H), 0.83 (s, 9H), 0.004 (s, 6H).

h) Preparation of [(3S,6R)-6-(tert-butyl-dimethyl-silanyloxy)-2-oxo-1-pyridin-3-ylmethyl-azepan-3-yl]-carbamic acid tert-butyl ester To a stirred solution of [(3S,6R)-6-(tert-butyl-dimethyl-silanyloxy)-2-oxo-azepan-3-yl]-carbamic acid tert-butyl ester (4.0 g, 11.1 mmol) in THF (30 mL) at −78° C. is added KN(Si(CH₃)₃)₂ (45.0 mL 1M THF, 45.0 mmol) slowly. The mixture is stirred at room temperature for 20 min, cooled to −78° C., and 3-chloromethyl-pyridine hydrochloride (2.75 g, 16.7 mmol) is added in portions. The reaction is warmed to room temperature and stirred for 16 h, H₂O (20 mL) is added and the mixture is partitioned with H₂O/ether, the organic layer is separated, dried with Na₂SO₄ and evaporated to give a white solid, 5.0 g (quantitative) of [(3S,6R)-6-(tert-butyl-dimethyl-silanyloxy)-2-oxo-1-pyridin-3-ylmethyl-azepan-3-yl]-carbamic acid tert-butyl ester. MS (ESI) 899.3 (2M+H)⁺ i) Preparation of (3S,6R)-3-amino-6-(tert-butyl-dimethyl-silanyloxy)-1-pyridin-3-ylmethyl-azepan-2-one To a stirred solution of [(3S,6R)-6-(tert-butyl-dimethyl-silanyloxy)-2-oxo-1-pyridin-3-ylmethyl-azepan-3-yl]-carbamic acid tert-butyl ester (5.0 g, 11.1 mmol) in CH₂Cl₂ (50 mL) at −78° C. is added trimethylsilyl iodide (2.8 g, 14.0 mmol) neat. After 30 min the reaction solution is warmed to 0° C. and stirred for 15 min. The reaction is quenched with a solution of CH₃OH (25 mL) and NH₄HCO₃ (10 mL, saturated in H₂O), and partitioned with H₂O/CH₂Cl₂. The CH₂Cl₂ fraction is dried over Na₂SO₄ and evaporated to a gum and chromatographed on silica (95% CH₂Cl₂/5% CH₃OH) to give 3.6 g (92.6%) of (3S,6R)-3-amino-6-(tert-butyl-dimethyl-silanyloxy)-1-pyridin-3-ylmethyl-azepan-2-one as a white solid. MS (ESI) 350.2 (M+H)⁺ j) Preparation of (R)-N-[(3S,6R)-6-(tert-butyl-dimethyl-silanyloxy)-2-oxo-1-pyridin-3-ylmethyl-azepan-3-yl]-2-[(4R,5R,6R)-6-((E)-3,3-dimethyl-but-1-enyl)-5-hydroxy-2,2-dimethyl-[1,3]dioxan-4yl]-2-methoxy-acetamide A solution of (3S,6R)-3-amino-6-(tert-butyl-dimethyl-silanyloxy)-1-pyridin-3-ylmethyl-azepan-2-one (1.84 g, 5.3 mmol), (4R,4aR)-4-((E)-3,3-Dimethyl-but-1-enyl)-7-methoxy-2,2-dimethyl-tetrahydro-furo[3,2-d][1,3]dioxin-6-one (1.0 g, 3.5 mmol) and diisopropylethylamine (1.37 g, 11.0 mmol) in isopropanol (10 mL) is refluxed for 16 h. The solution is evaporated and chromatographed on silica (95% CH₂Cl₂/5% CH₃OH) to give 1.27 g (57.0%) of (R)-N-[(3S,6R)-6-(tert-butyl-dimethyl-silanyloxy)2-oxo-1-pyridin-3-ylmethyl-azepan-3-yl]-2-[(4R,5R,6R)-6-((E)-3,3-dimethyl-but-1-enyl)-5-hydroxy-2,2-dimethyl-[1,3]dioxan-4-yl]-2-methoxy-acetamide as a white solid. MS (ESI) 634.3 (M+H)⁺

Preparation of (R)-2-[(4R,5R,6R)-6-((E)-3,3-dimethyl-but-1-enyl)-5-hydroxy-2,2-dimethyl-[1,3]dioxan-4-yl]-N-((3S,6R)-6-hydroxy-2-oxo-1-pyridin-3-ylmethyl-azepan-3-yl)2-methoxy-acetamide To a stirred solution of (R)-N-[(3S,6R)-6-(tert-butyl-dimethyl-silanyloxy)-2-oxo-1-pyridin-3-ylmethyl-azepan-3-yl]-2-[(4R,5R,6R)-6-((E)-3,3-dimethyl-but-1-enyl)-5-hydroxy-2,2-dimethyl-[1,3]dioxan-4-yl]-2-methoxy-acetamide (1.2 g, 1.9 mmol) at room temperature is added tetrabutylammonium fluoride (5.68 mL, 1 M THF, 5.68 mmol). After 2 h, the solution is evaporated and chromatographed on silica (95% CH₂Cl₂/5% CH₃OH) to give 0.74 g (75.2%) of (R)-2-[(4R,5R,6R)-6-((E)-3,3-dimethyl-but-1-enyl)-5-hydroxy-2,2-dimethyl-[1,3]dioxan-4-yl]-N-((3S,6R)-6-hydroxy-2-oxo-1-pyridin-3-ylmethyl-azepan-3-yl)-2-methoxy-acetamide as a white solid. $^1$H NMR 300 MHz δ 8.52(m, 2H), 7.69 (m, 1H), 7.29 (m, 1H), 5.77 (d, 1H), 5.54(dd, 1H), 4.69 (m, 2H), 4.29 (m, 2H), 4.10 (m, 2H), 3.92 (d, 1H), 3.54 (m, 2H), 3.50 (s, 3H), 3.33 (m,2H), 2.15 (m, 1H), 2.00 (m, 1H), 1.90 (m, 1H), 1.67 (m, 3H), 1.46 (m, 4H), 1.04 (s, 9H), 1.00 (t, 2H); MS (ESI) 520.2 (M+H)$^+$.

l) Preparation of tetradecanoic acid (3R,6S)-6-{(R)-2-[(4R,5R,6R)-6-((E)-3,3-dimethyl-but-1-enyl)-5-hydroxy-2,2-dimethyl-[1,3]dioxan-4-yl]-2-methoxy-acetylamino}-7-oxo-1-pyridin-3-ylmethyl-azepan-3-yl ester To a stirred solution of tetradecanoic acid (0.39 g 1.7 mmol) and 4-dimethylaminopyridine (0.21 g, 1.7 mmol) in CH$_2$Cl$_2$(15 mL) is added 1-ethyl-3-[3-(dimethylamino)propyl]-carbodiimidehydrochloride (0.34 g, 1.7 mmol) at room temperature. After 30 min (R)-2-[(4R,5R,6R)-6-((E)3,3-dimethyl-but-1-enyl)-5-hydroxy-2,2-dimethyl-[1,3]dioxan-4-yl]-N-((3S,6R)-6-hydroxy-2-oxo-1-pyridin-3-ylmethyl-azepan-3-yl)-2-methoxy-acetamide (0.74 g, 1.4 mmol) is added and stirred for 16 h. The reaction is concentrated and chromatographed on silica (98% CH$_2$Cl$_2$/2% CH$_3$OH) to give 0.3 g (28.8%) of tetradecanoic acid (3R,6S)-6-{(R)-2-[(4R,5R,6R)-6-((E)-3,3-dimethyl-but-1-enyl)-5-hydroxy-2,2-dimethyl-[1,3]dioxan-4-yl]-2-methoxy-acetylamino}-7-oxo-1-pyridin-3-ylmethyl-azepan-3-yl ester as a white solid. $^1$H NMR 300 MHz δ 8.54(s, 2H), 7.88 (d, 1H), 7.63 (d, 1H), 7.29 (m, 1H), 5.77 (d, 1H), 5.54(dd, 1H), 5.06 (d, 1H), 4.75 (m, 1H), 4.50 (m, 1H), 4.29 (m, 2H), 4.08 (d, 1H), 3.90 (d, 1H), 3.52 (s, 3H), 3.50 (m, 1H), 3.25 (d, 1H), 2.27 (t, 2H), 2.15 (m, 2H), 2.00 (m, 1H), 1.60 (m, 3H), 1.46 (d, 2H), 1.25 (m, 24H), 1.04 (s, 9H), 0.88 (t, 3H); MS (ESI) 730.3 (M+H)$^+$.

m) Preparation of title compound tetradecanoic acid (3R,6S)-7-oxo-1-pyridin-3-ylmethyl-6-((2R,3R,4S,5R)-(E)-3,4,5-trihydroxy-2-methoxy-8,8-dimethyl-non-6-enoylamino)-azepan-3-yl ester To a solution of TFA/THF/H$_2$O (3/3/2) (30 mL) at 0° C. is added tetradecanoic acid (3R,6S)-6-{(R)-2-[(4R,5R,6R)-6-((E)-3,3-dimethyl-but-1-enyl)-5-hydroxy-2,2-dimethyl-[1,3]dioxan-4-yl]-2-methoxy-acetylamino}-7-oxo-1-pyridin-3-ylmethyl-azepan-3-yl ester (0.3 g, 0.42 mmol). After 30 min the reaction is evaporated under high vacuum, toluene is added (20 mL) and evaporated under high vacuum to remove remaining TFA. The residue is dissolved in CH$_2$Cl$_2$ at 0° C. and neutralized by adding NH$_4$OH dropwise. The solution is concentrated and chromatographed on silica (98% CH$_2$Cl$_2$/2% CH$_3$OH) to give 0.2 g (70.7%) of tetradecanoic acid (3R,6S)-7-oxo-1-pyridin-3-ylmethyl-6-((2R,3R,4S,5R)-(E)-3,4,5-trihydroxy-2-methoxy-8,8-dimethyl-non-6-enoylamino)-azepan-3-yl ester as a with solid. $^1$H NMR 300 MHz δ 8.62 (s, 2H), 8.17 (d, 1H), 7.67 (d, 1H), 7.33 (m, 1H), 5.83 (d, 1H), 5.42(dd, 1H), 4.69 (m, 1H), 4.54 (m, 1H), 4.33 (d, 1H), 4.32 (t, 2H), 3.83 (dd, 2H), 3.67 (d, 1H), 3.25 (s, 3H), 3.17 (m, 1H), 2.94 (d, 1H), 2.29 (t, 2H), 2.13 (m, 2H), 2.00 (m, 1H), 1.60 (m, 3H), 1.29 (m, 24H), 1.04 (s, 9H), 0.89 (t, 3H); MS (ESI) 690.3 (M+H)$^+$.

Example 2

(E)-(2R,3R,4S,5R)-3,4,5-Trihydroxy-2-methoxy-8,8-dimethyl-non-6-enoic acid [(3S,6R)-6-(6-aminohexyloxy)-1-methyl-2oxo-azepan-3-yl]-amide

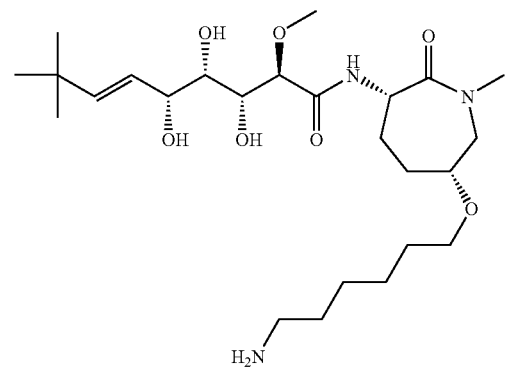

a) Preparation of [(3S,6R)-6-(tert-butyl-dimethyl-silanyloxy)-1-methyl-2-oxo-azepan-3-yl]-carbamic acid tert-butyl ester Following the procedure of Example 1(f)-1(h), except CH$_3$-I is substituted for 2-chloromethyl-pyridine and one equivalent of KN(Si(CH$_3$)$_3$)$_2$ is used in step 1(h) to give the product as an oil. $^1$H NMR (CDCl$_3$) δ 0.05 (s, 3H), 0.07 (s, 3H), 0.87 (s, 9H), 1.44 (s, 9H), 1.8 (m, 4H), 3.06 (s, 3H), 3.2 (dd, 1H), 3.7 (d, $_1$H), 4.0 (m, 1H). 4.28 (dd, 1H), 6.0 (d, 1H).

b) Preparation of ((3S,6R)-6-hydroxy-1-methyl-2-oxo-azepan-3-yl)-carbamic acid tert-butyl ester To a solution of [(3S,6R)-6-(tert-butyl-dimethyl-silanyloxy)-1-methyl-2-oxo-azepan-3-yl]-carbamic acid tert-butyl ester (0.85 g, 2.27 mmol) in THF (40 mL) is added tetrabutylammonium fluoride (3 mL 1M THF, 3 mmol) at room temperature. The reaction solution is stirred for 4 h, then H$_2$O (40 mL) is added and the solution concentrated under vacuum to ½ its volume and extracted 3× with CH$_2$Cl$_2$ (40 mL). The combined CH$_2$Cl$_2$ extracts are adsorbed on silica and chromatographed (5% CH$_3$OH/CH$_2$Cl$_2$) to give 0.568 g (72%) of ((3S,6R)-6-hydroxy-1-methyl-2-oxo-azepan-3-yl)-carbamic acid tert-butyl ester as a white solid. $^1$H NMR (CDCl$_3$) δ 1.44 (s, 9H), 1.7-2.05 (m, 4H), 3.1 (s, 3H), 3.37 (dd, 1H), 3.73 (d, 1H), 4.07 (m, 1H), 4.31 (m, 1H), 6.0 (d, 1H).

Preparation of [(3S,6R)-6-(6-azido-hexyloxy)-1-methyl-2-oxo-azepan-3-yl]-carbamic acid tert-butyl ester To a stirred solution of ((3S,6R)-6-hydroxy-1-methyl-2-oxo-azepan-3-yl)-carbamic acid tert-butyl ester (0.70 g, 2.6 mmol) in THF (5 mL) cooled to −78° C. is added NaN(Si (CH$_3$)$_3$)$_2$ (2.8 mL 1M THF, 2.8 mmol). After 10 min trifluoro-methanesulfonic acid 6-azido-hexyl ester (0.76 g, 3.1 mmol) is added neat and stirred for 10 min at −78° C. then warmed and stirred at room temperature for 1 h. NaHCO$_3$ (5 mL 1M H$_2$O) is added and the solution is partitioned with H$_2$O/EtOAc, the EtOAc extract is dried with Na$_2$SO$_4$ and evaporated to an oil. The oil is adsorbed on silica and chromatographed (20% EtOAc/CH$_2$Cl$_2$) to give 0.32 g (32%) of [(3S,6R)-6-(6-azido-hexyloxy)-1-methyl-2-oxo-azepan-3-yl]-carbamic acid tert-butyl ester as an oil. $^1$H NMR (CDCl$_3$) δ 1.34 (s, 9H), 1.24-2.1 (m, 12H), 2.95 (s, 3H), 3.1-3.35 (m, 6H), 3.44 (m, 1H), 3.55 (d, 1H), 4.2 (m, 1H).

Preparation of (3S,6R)-3-amino-6-(6-azido-hexyloxy-1-methyl-azepan-2-one

To a stirred solution of [(3S,6R)-6-(6-azido-hexyloxy)-1-methyl-2-oxo-azepan-3-yl]-carbamic acid tert-butyl ester (0.32 g, 0.83 mmol) in CH$_2$Cl$_2$ (4 mL) is added TFA (1 mL) at room temperature. After 1 h, the reaction is evaporated under vacuum, toluene (20 mL) is added and evaporated under vacuum to remove remaining TFA. The residue is dissolved in CH$_2$Cl$_2$ (20 mL) saturated with NH$_3$ adsorbed on silica and chromatographed (50% EtOAc/CH$_2$Cl$_2$/NH$_3$ then 10% CH$_3$OH/CH$_2$Cl$_2$/NH$_3$) to give 0.207 g (88%) of (3S,6R)-3-amino-6-(6-azido-hexyloxy)-1-methyl-azepan-2-one as an oil. MS (ESI) 284.2 (M+H)$^+$ Preparation of (R)-N-[(3S,6R)-6-(6-azido-hexyloxy)-1-methyl-2-oxo-azepan-3-yl]-2-[(4R,5R,6R)-6-((E)-3,3-dimethyl-but-1-enyl)-5-hydroxy-2,2-dimethyl-[1,3]dioxan-4-yl]-2-methoxy-acetamide To a solution of (3S,6R)-3-amino-6-(6-azido-hexyloxy)-1-methyl-azepan-2-one (0.207 g, 0.73 mmol) in isopropanol (1 mL) is added (4R,4aR)-((E)-3,3-dimethyl-but-1-enyl)-7-methoxy-2,2-dimethyl-tetrahydro-furo[3,2-d][1,3]dioxin-6-one (0.3 g, 1 mmol) and heated to reflux for 18 h. The solution is evaporated under vacuum adsorbed on silica and chromatographed (CH$_2$Cl$_2$ to EtOAc gradient) to give 0.245 g (59%) of (R)-N-[(3S,6R)-6-(6-azido-hexyloxy)-1-methyl-2-oxo-azepan-3-yl]-2-[(4R,5R,6R)-6-((E)-3,3-dimethyl-but-1-enyl)-5-hydroxy-2,2-dimethyl-[1,3]dioxan-4-yl]-2-methoxy-acetamide as a solid. (ESI) 568.1 (M+H)$^+$ f) Preparation of (E)-(2R,3R,4S,5R)-3,4,5-trihydroxy-2-methoxy-8,8-dimethyl-non-6-enoic acid [(3S,6R)-6-(6-azido-hexyloxy)-1-methyl-2-oxo-azepan-3-yl]-amide Following the procedure of Example 1 m) except (R)-N-[(3S,6R)-6-(6-azido-hexyloxy)-1-methyl-2-oxo-azepan-3-yl]-2-[(4R,5R,6R)-6-((E)3,3-dimethyl-but-1-enyl)-5-hydroxy-2,2-dimethyl-[1,3]dioxan-4-yl]-2-methoxy-acetamide is substituted for tetradecanoic acid (3R,6S-6-{(R)-2-[(4R,5R,6R)-6-((E)-3,3-dimethyl-but-1-enyl)-5-hydroxy-2,2-dimethyl-[1,3]dioxan-4-yl]-2-methoxy-acetylamino}-7-oxo-1-pyridin-3-ylmethyl-azepan-3-yl ester. MS (ESI) 528.0 (M+H)$^+$ g) Preparation of title compound (E)-(2R,3R,4S,5R)-3,4,5-trihydroxy-2-methoxy-8,8-dimethyl-non-6-enoic acid [(3S,6R)-6-(6-amino-hexyloxy)-1-methyl-2-oxo-azepan-3-yl]-amide To a stirred solution of (E)-(2R,3R,4S,5R)-3,4,5-trihydroxy-2-methoxy-8,8-dimethyl-non-6-enoic acid [(3S,6R)-6-(6-azido-hexyloxy)-1-methyl-2-oxo-azepan-3-yl]-amide (0.13 g, 0.25 mmol) in THF (2 mL) is added H$_2$O and triphenylphosphine (0.120 g, 0.5 mmol). After 8 h the reaction solution is evaporated under vacuum to give a semisolid residue that is dissolved in CH$_2$Cl$_2$ (10 mL), adsorbed on silica and chromatographed (CH$_2$Cl$_2$/NH$_3$ to 25% CH$_3$OH/CH$_2$Cl$_2$/NH$_3$ gradient) to give 0.106 g (85%) of (E)-(2R,3R,4S,5R)-3,4,5-trihydroxy-2-methoxy-8,8-dimethyl-non-6-enoic acid [(3S,6R)-6-(6-amino-hexyloxy)-1-methyl-2-oxo-azepan-3-yl]-amide as a white solid. MS (ESI) 502.1 (M+H)$^+$ Example 3

(E)-(2R,3R,4S,5R)-3,4,5-Trihydroxy-2-methoxy-8,8-dimethyl-non-6-enoic acid ((3S,6S)-6-azido-2-oxo-azepan-3-yl)-amide

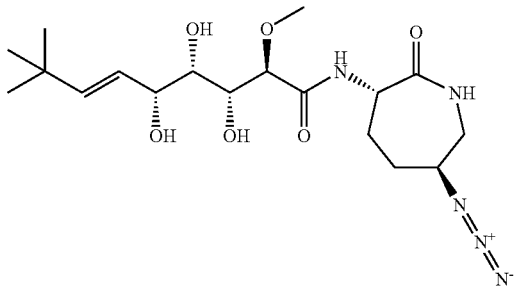

Preparation of ((3S,6S)-6-azido-2-oxo-azepan-3-yl)-carbamic acid tert-butyl ester To a stirred solution of ((3S,6R)-6-hydroxy-2-oxo-azepan-3-yl)carbamic acid tert-butyl ester (3 g, 12.3 mmol example 1 f) and triphenylphosphine (3.75 g, 14.1 mmol) in THF (200 mL) at 0° C. is added diethyl azodicarboxylate (2.2 mL, 13.5 mmol) at a rate to maintain a temperature <5° C. followed immediately by addition of diphenylphosphoryl azide (2.9 mL, 13.5 mmol). The reaction is stirred for 60 h at room temperature in the dark, the solvent is removed under vacuum and the residue chromatographed on silica (hexane to ether gradient) to give 2.33 g (70%) of ((3S,6S)-6-azido-2-oxo-azepan-3-yl)-carbamic acid tert-butyl ester as a solid. MS (ESI) 270 (M+H)$^+$ Preparation of (3S,6S)-3-amino-6-azido-azepan-2-one Following the procedure of example 2d) ((3S,6S)-6-azido-2-oxo-azepan-3-yl)-carbamic acid tert-butyl ester is substituted for [(3S,6R)-6-(6-azido-hexyloxy)-1-methyl-2-oxo-azepan-3-yl]-carbamic acid tert-butyl ester to give (3S,6S)-3-amino-6-azido-azepan-2-one. MS (ESI) 170 (M+H)$^+$ Preparation of (R)-N-((3S,6S)-6-azido-2-oxo-azepan-3-yl)-2-[(4R,5R,6R)-6-((E)-3,3-dimethyl-but-1-enyl)-5-hydroxy-2,2-dimethyl-[1,3]dioxan-4-yl]-2-methoxy-acetamide Following the procedure of example 2 e) (3S,6S)-3-amino-6-azido-azepan-2-one is substituted for (3S,6R)-3-amino-6-(6-azido-hexyloxy)-1-methyl-azepan-2-one to give (R)-N-((3S,6S)-6-azido-2-oxo-azepan-3-yl)-2-[(4R,5R,6R)-6-((E)-3,3-dimethyl-but-1-enyl)-5-hydroxy-2,2-dimethyl-[1,3]dioxan-4-yl]-2-methoxy-acetamide. MS (ESI) 454.2 (M+H)$^+$ d) Preparation of title compound (E)-(2R,3R,4S,5R)-3,4,5-trihydroxy-2-methoxy-8,8-dimethyl-nonenoic acid ((3S,6S)-6-azido-2-oxo-azepan-3-yl)-amide Following the procedure of example 1 m) (R)-N-((3S,6S)-6-azido-2-oxo-azepan-3-yl)-2-[(4R,5R,6R)-6-((E)-3,3-dimethyl-but-1-enyl-5-hydroxy-2,2-dimethyl-[1,3]dioxan-4-yl]-2-methoxy-acetamide is substituted for tetradecanoic acid (3R,6S)-6-{(R)-2-[(4R,5R,6R)-6-((E)-3,3-dimethyl-but-1-enyl)-5-hydroxy-2,2-dimethyl-[1,3]dioxan-4-yl]-2-methoxy-acetylamino}-7-oxo-1-pyridin-3-ylmethyl-azepan-3-yl ester to give the title compound. MS (ESI) 414.2 (M+H)+

Example 4

[(S)-2-Oxo-3-((2R,3R,4S,5R)-(E)-3,4,5-trihydroxy-2-methoxy-8-methyl-non-6-enoylamino)-azepan-1-yl]-acetic acid benzyl ester

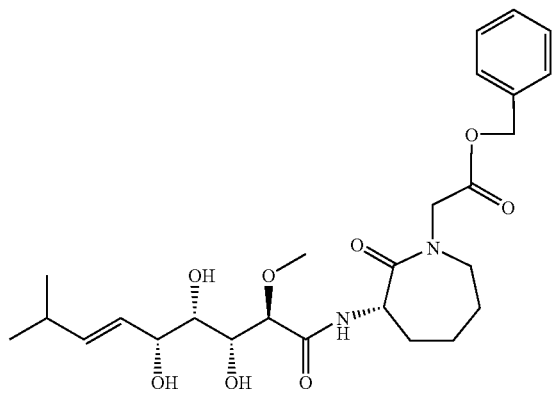

Preparation of (4R,4aR)-7-methoxy-2,2-dimethyl-4-((E)-3-methyl-but-1-enyl)-tetrahydro-furo[3,2-d][1,3]dioxin-6-one Following the procedure of example 1a)-e) except 1,1-diiodo-2-methyl-propane is substituted for 1,1-diiodo-2,2-dimethyl-propane to give (4R,4aR)-7-methoxy-2,2-dimethyl-4-((E)-3-methyl-but-1-enyl)tetrahydro-furo[3,2-d][1,3]dioxin-6-one as a white solid. $^1$HNMR (CDCl$_3$) δ 5.85 (dd, J=15.6, 6.22 Hz, 1H), 5.64 (ddd, J=15.6, 7.5, 1.27 Hz, 1H), 4.74 (dd, J=3.79, 2.09 Hz, 1H), 4.48 (dd, J=7.49, 1.78 Hz, 1H), 4.12 (d, J=3.86 Hx, 1H), 4.02 (t, J=2.02 Hz, 1H), 3.68 (s, 3H), 2.36 (m, 1H), 1.56 (s, 3H), 1.51 (s, 3H), 1.04 (d, J=1.9 Hz, 3H), 1.03 (d, J=1.9 Hz, 3H); $^{13}$C NMR (CDCl$_3$) δ 172.8, 143.2, 122.0, 98.7, 79.0, 71.7, 70.0, 67.6, 59.2, 30.7, 29.2, 21.9, 21.8, 19.2. HRMS: calculated for (M+Na)+(C$_{14}$H$_{22}$O$_5$Na) 293.1365, found 293.1355.

Preparation of ((S)-3-amino-2-oxo-azepan-1-yl)-acetic acid benzyl ester

Following the procedure of example 1h) except ((S)-2-oxo-azepan-3-yl)-carbamic acid tert-butyl ester is substituted for [(3S,6R)-6-(tert-butyl-dimethyl-silanyloxy)-2-oxo-azepan-3-yl]-carbamic acid tert-butyl ester and bromoacetic acid benzyl ester is substituted for 2-chloromethyl-pyridine and one equivalent of KN(Si(CH$_3$)$_3$)$_2$ base to give ((S)-3-tert-butoxycarbonylamino-2-oxo-azepan-1-yl)-acetic acid benzyl ester. Removal of the Boc group by procedure 2d) gives ((S)-3-amino-2-oxo-azepan-1-yl)-acetic acid benzyl ester.

c) Preparation of title compound [(S)-2-oxo-3-((2R,3R,4S,5R)-(E)-3,4,5-trihydroxy-2-methoxy-8-methyl-non-6-enoylamino)-azepan-1-yl]-acetic acid benzyl ester The product of 4b) is processed as in example 2 e)-f) to give the title compound as a white solid.

Examples 5-59

The following compounds are prepared by similar methods utilizing analogous starting materials:

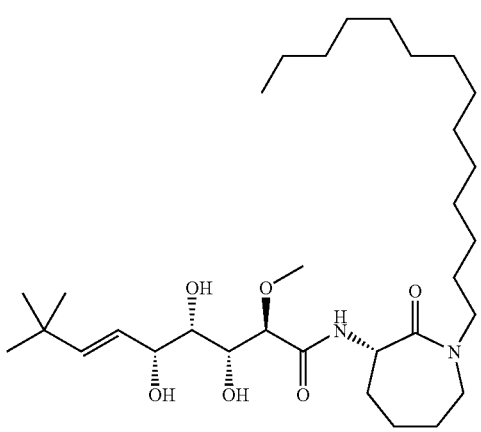

Example 5
MS ESI 569.3
(M + H)+

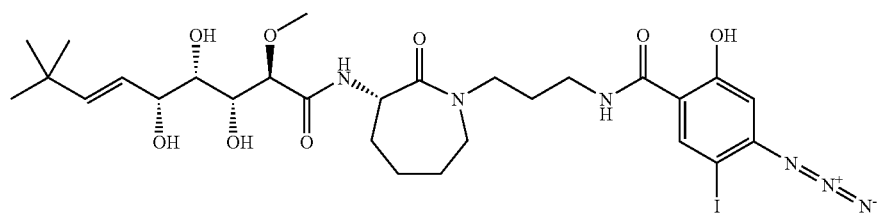
Example 6
MS ESI 717.2
(M + H)+
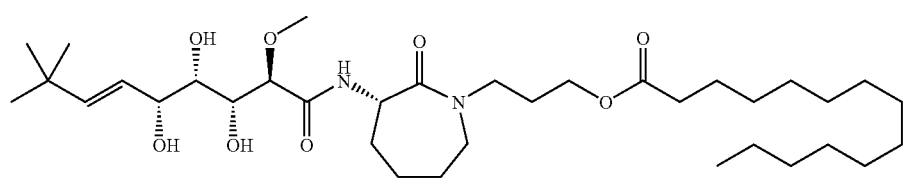
Example 7
MS ESI 641.5
(M + H)+
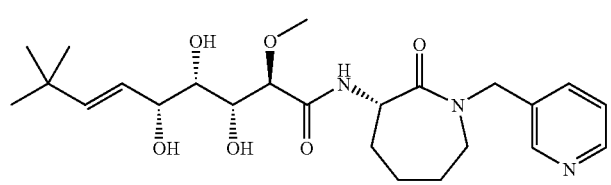
Example 8
MS ESI 464.4
(M + H)+
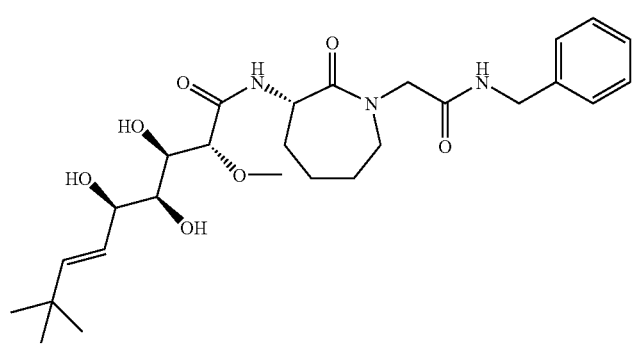
Example 9
MS ESI 542.3
(M + Na)+
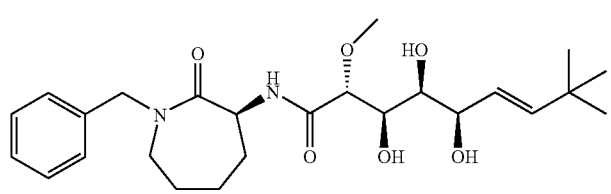
Example 10
MS ESI 463.3
(M + H)+
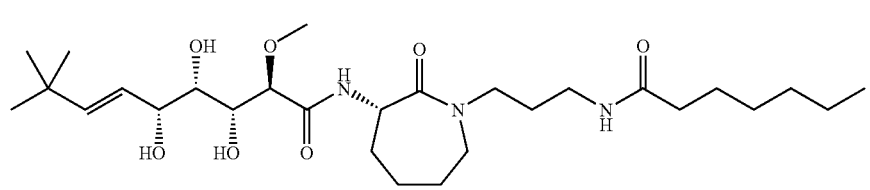
Example 11
MS ESI 542.3
(M + H)+
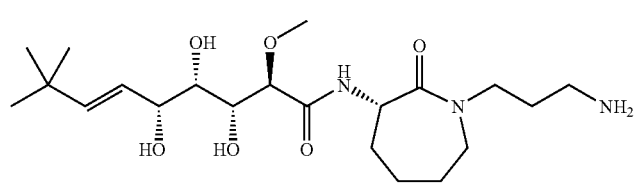
Example 12
MS ESI 430.2
(M + H)+

-continued
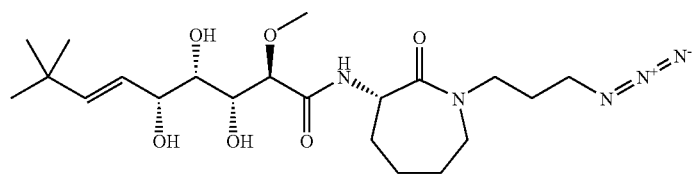
Example 13
MS ESI 472.3
(M + H)+
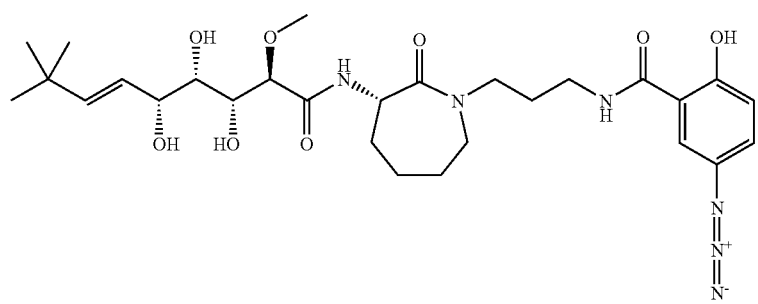
Example 14
MS ESI 591.2
(M + H)+
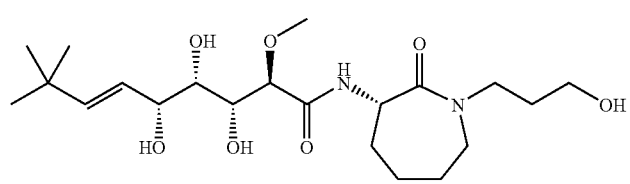
Example 15
MS ESI 431.2
(M + H)+
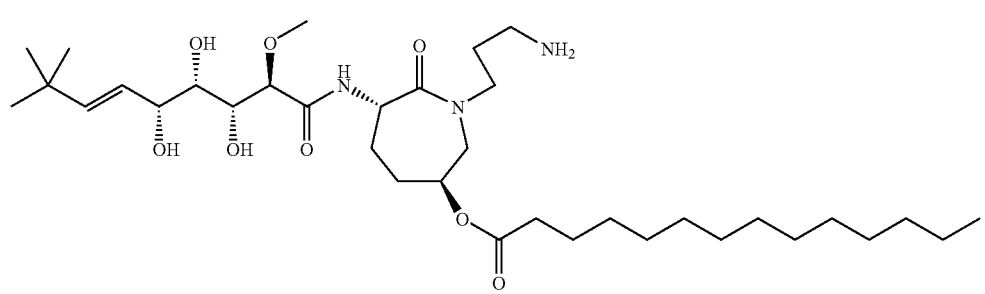
Example 16
MS ESI 656.4
(M + H)+
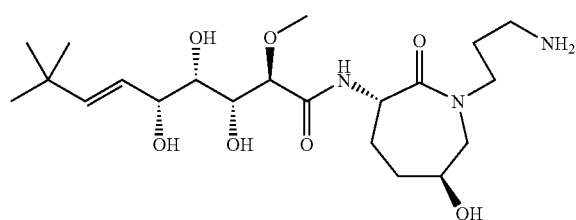
Example 17
MS ESI 446.2
(M + H)+
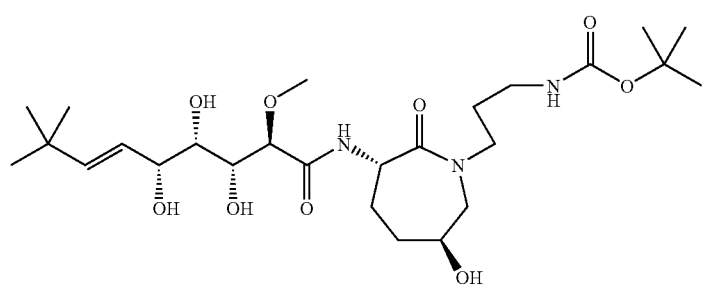
Example 18
MS ESI 546.3
(M + H)+

-continued
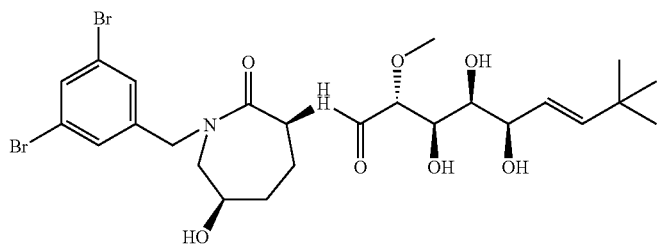
Example 19
MS ESI 637.1
(M + H)+
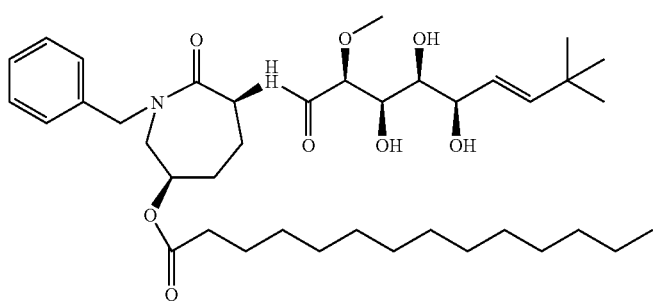
Example 20
MS ESI 689.4
(M + H)+
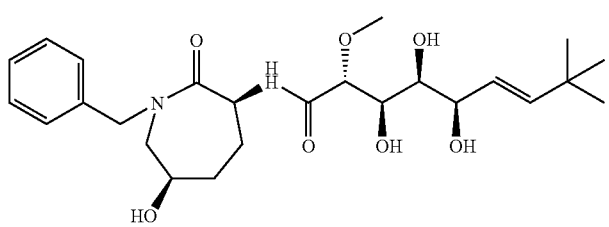
Example 21
MS ESI 479.2
(M + H)+
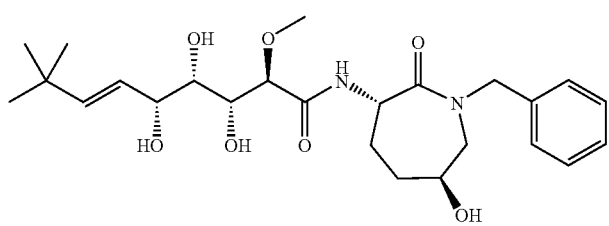
Example 22
MS ESI 479.2
(M + H)+
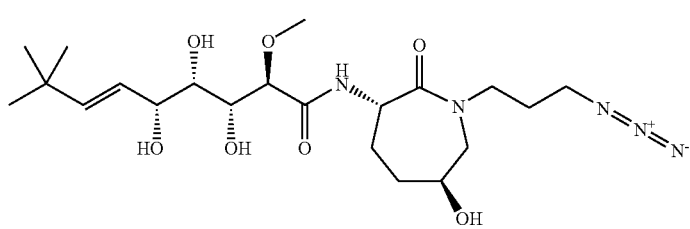
Example 23
MS ESI 472.2
(M + H)+
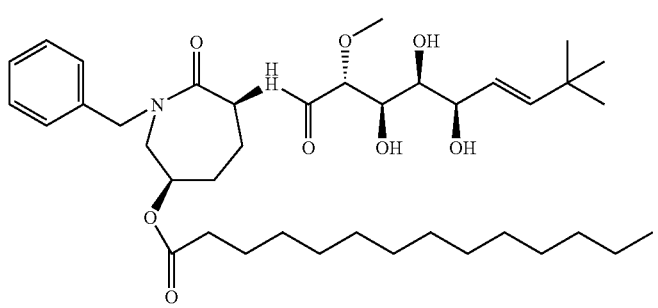
Example 24
MS ESI 689.2
(M + H)+

-continued
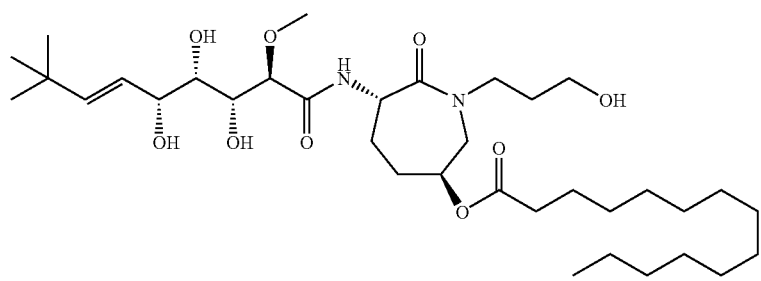
Example 25
MS ESI 657.3
(M + H)+
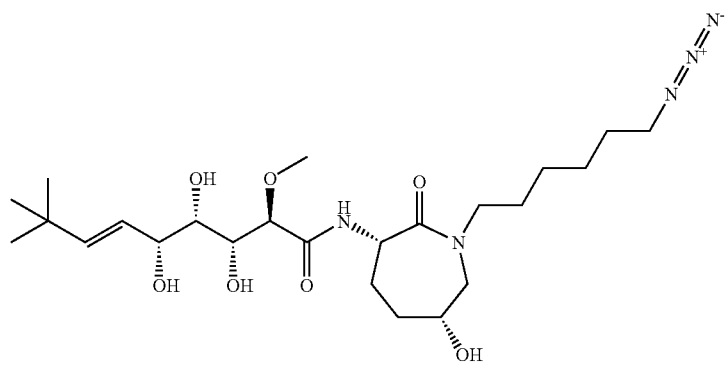
Example 26
MS ESI 514.1
(M + H)+
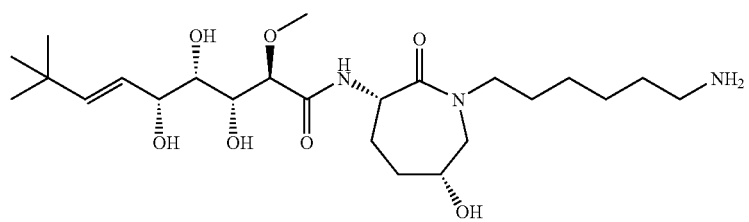
Example 27
MS ESI 488.1
(M + H)+
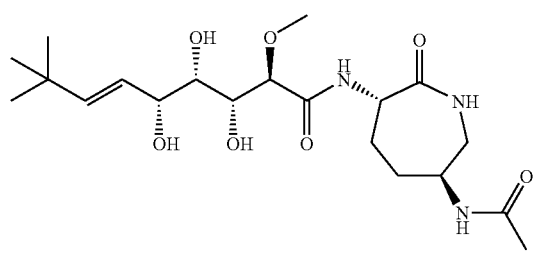
Example 28
MS ESI 430.2
(M + H)+
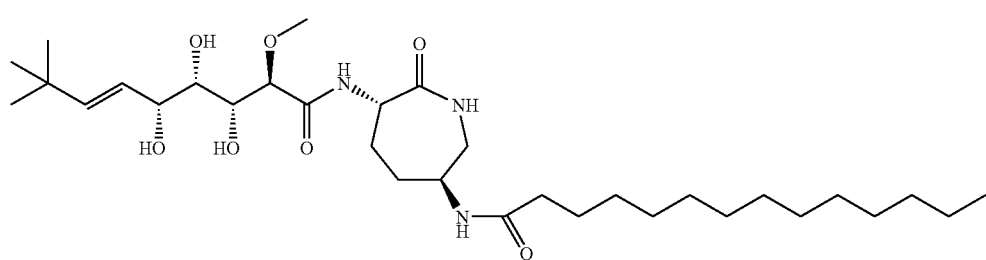
Example 29
MS ESI 598.2
(M + H)+

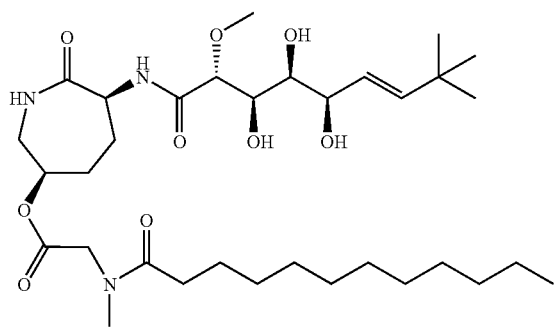
Example 30
MS ESI 642.3
(M + H)+
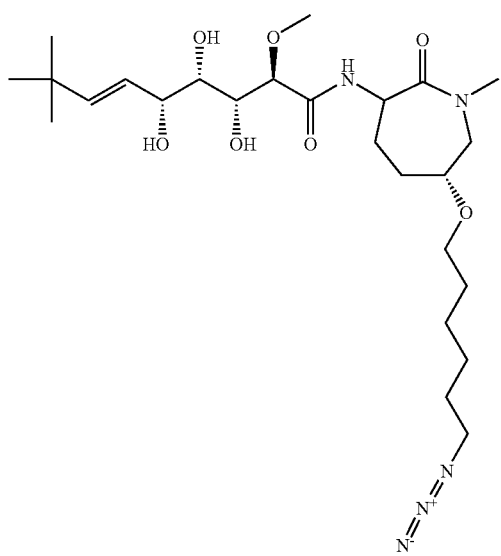
Example 31
MS ESI 528.0
(M + H)+
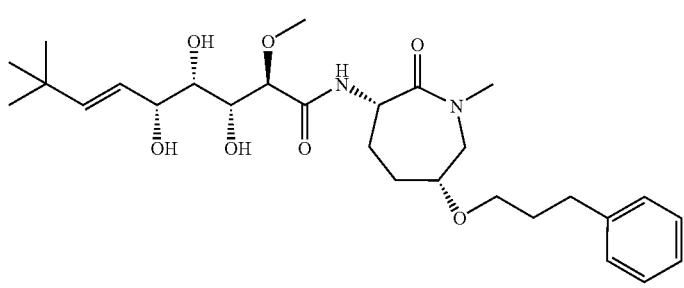
Example 32
MS ESI 521.2
(M + H)+
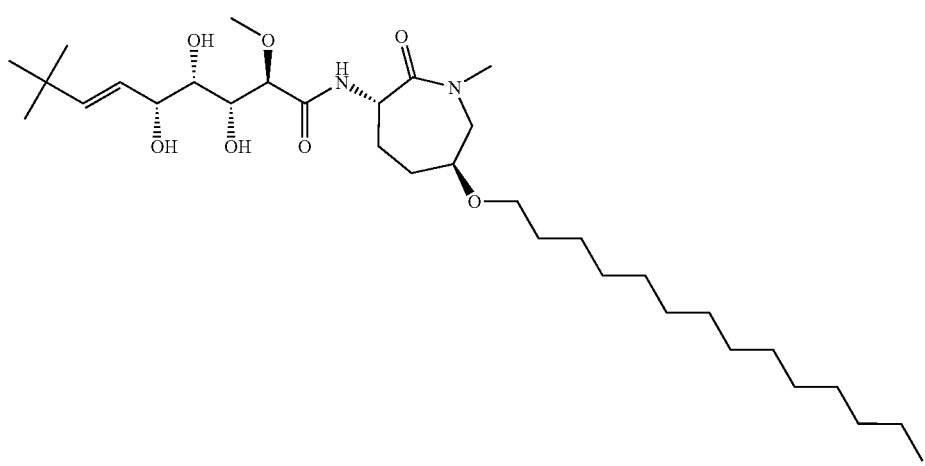
Example 33
MS ESI 1197.4
(2M + H)+

-continued
| | |
|---|---|
| 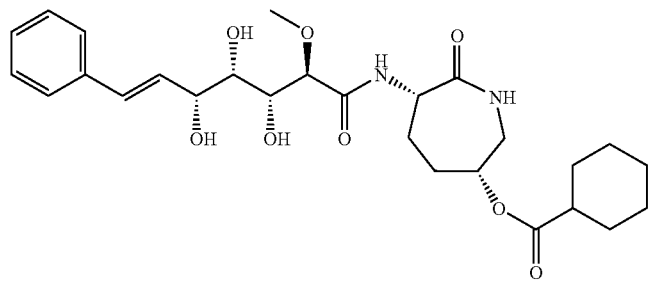 | Example 34<br>MS ESI 519.0<br>(M + H)$^+$ |
| 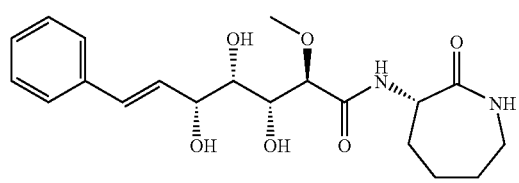 | Example 35<br>MS ESI 393.0<br>(M + H)$^+$ |
| 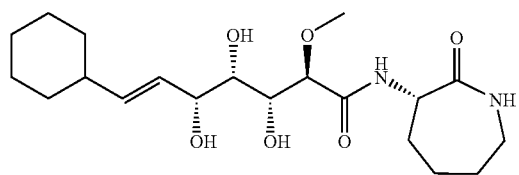 | Example 36<br>MS ESI 398.5<br>(M + H)$^+$ |
| 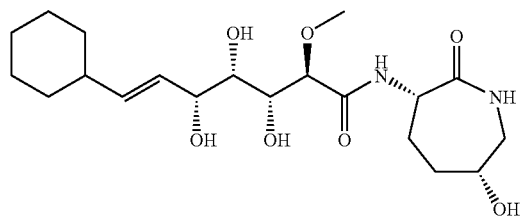 | Example 37 |
| 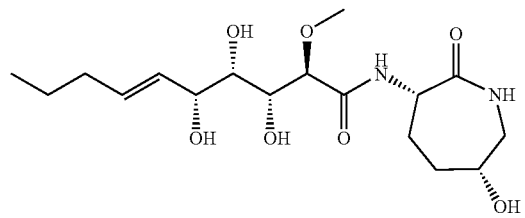 | Example 38<br>MS ESI 375.1<br>(M + H)$^+$ |
| 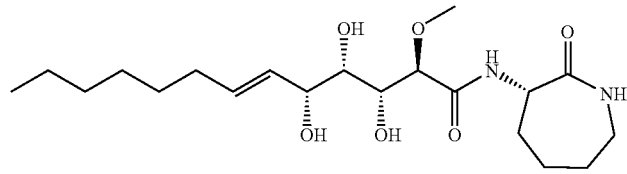 | Example 39<br>MS ESI 401.21<br>(M + H)$^+$ |
| 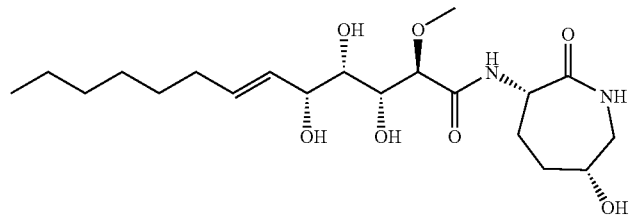 | Example 40<br>MS ESI 417.1<br>(M + H)$^+$ |

-continued
| | |
|---|---|
| 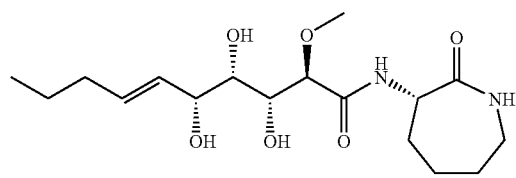 | Example 41<br>MS ESI 359.3<br>(M + H)+ |
| 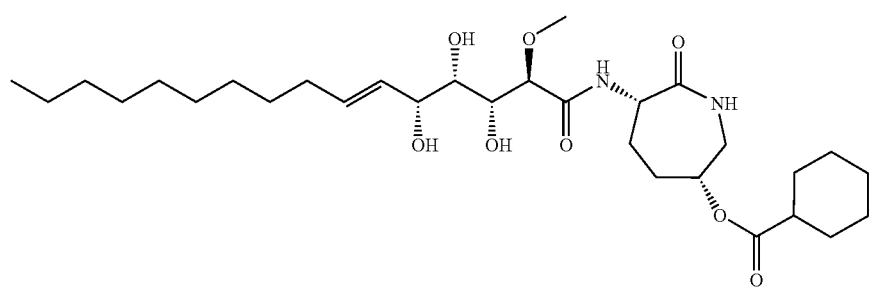 | Example 42<br>MS ESI 569.5<br>(M + H)+ |
| 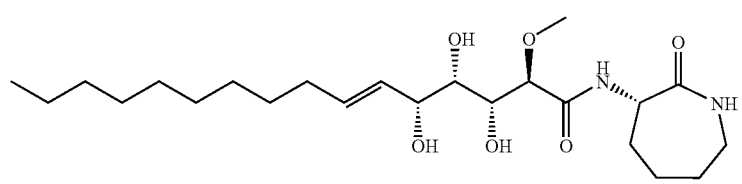 | Example 43<br>MS ESI 443.4<br>(M + H)+ |
| 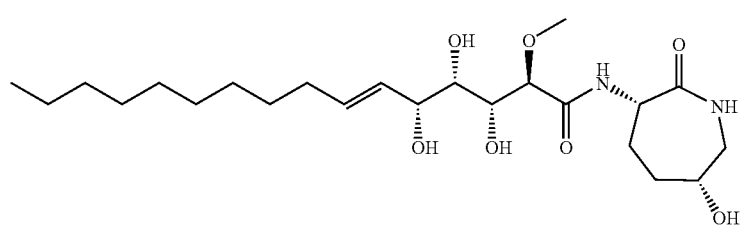 | Example 44<br>MS ESI 459.4<br>(M + H)+ |
| 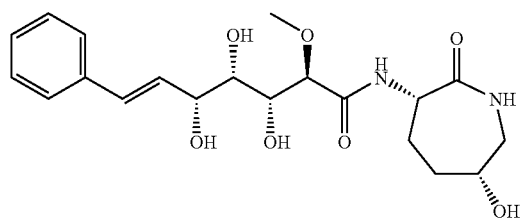 | Example 45<br>MS ESI 409.3<br>(M + H)+ |
| 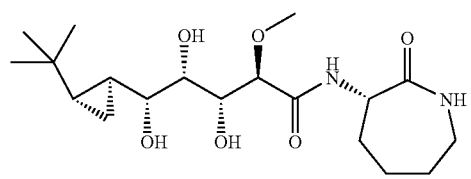 | Example 46<br>MS ESI 387.3<br>(M + H)+ |
| 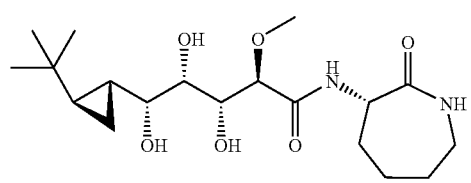 | Example 47<br>MS ESI 387.3<br>(M + H)+ |

-continued
| | |
|---|---|
| 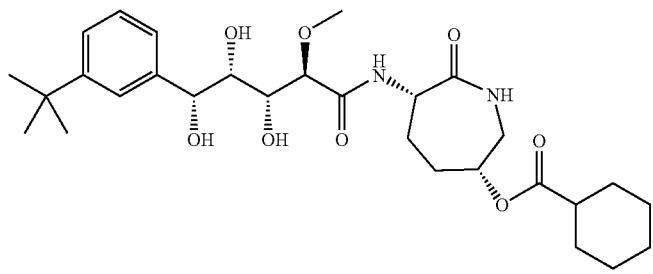 | Example 48<br>MS ESI 549.3<br>(M + H)+ |
| 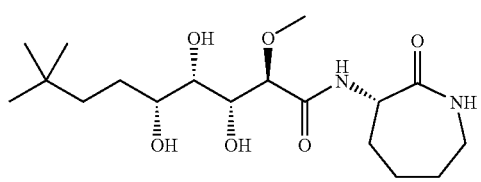 | Example 49<br>MS ESI 375.3<br>(M + H)+ |
| 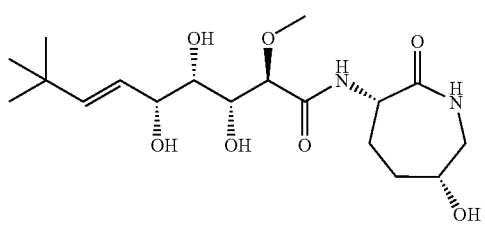 | Example 50<br>MS ESI<br>(M + H)+ |
| 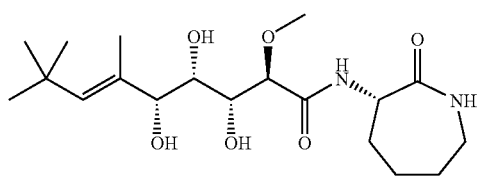 | Example 51<br>MS ESI 387.3<br>(M + H)+ |
| 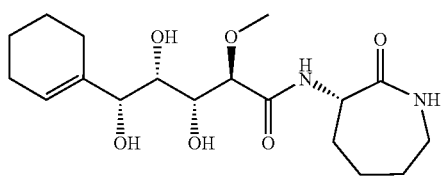 | Example 52<br>MS ESI 371.2<br>(M + H)+ |
| 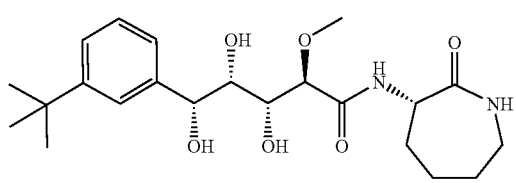 | Example 53<br>MS ESI 423.2<br>(M + H)+ |
| 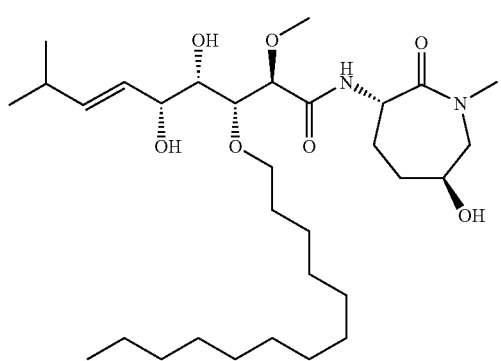 | Example 54<br>MS ESI 585.4<br>(M + H)+ |

-continued

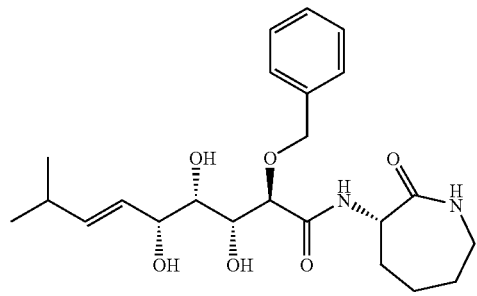

Example 55
MS ESI 435.0
(M + H)+

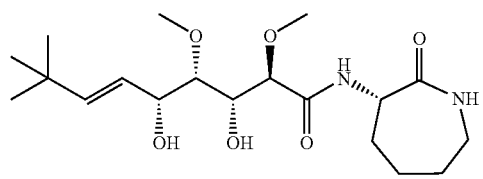

Example 56
MS ESI 387.2
(M + H)+

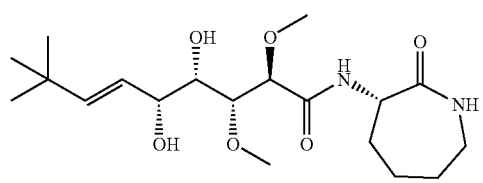

Example 57
MS ESI 387.3
(M + H)+

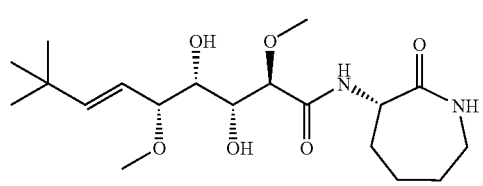

Example 58
MS ESI 387.2
(M + H)+

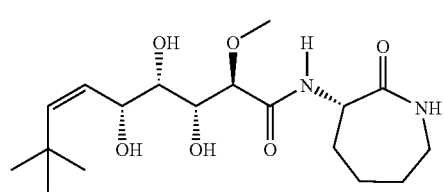

Example 59

The anti-tumor activity of the compounds of formula I may be demonstrated employing the Anchorage Dependent Growth Monolayer Assay (ADGMA) which measures the growth inhibitory effects of test compounds on proliferation of adherent cell monolayers. This assay was adapted from the 60 cell line assay used by the National Cancer institute (NCI) with the following modifications: 1) cell lines representative for the Important tumor types, for example, MDA-MB-435 breast and A549 non-small cell lung, are utilized; and 2) a tetrazolium derivative, viz., MTS, is utilized to determine cell density.

The ADGMA compares the number of viable cells following a 3-day exposure to a test compound relative to a number of cells present at the time the test compound is added. Cell viability is measured using a tetrazolium derivative, viz., 3-(4,5-dimethylthiazol-2-yl)-5-(3-carboxymethoxyphenyl)-2-(4-sulfophenyl)-2H-tetrazolium, inner salt (MTS) that is metabolically reduced in the presence of an electron coupling agent (PMS; phenazine methosulfate) by viable cells to a water-soluble formazan derivative. The absorbance at 490 nm ($A_{490}$) of the formazan derivative is proportional to the number of viable cells. The $IC_{50}$ for a test compound is the concentration of compound required to reduce the final cell number to 50% of the final control cell number.

The MDA-MB435 breast carcinoma line is obtained from the American Type Culture Collection (ATCC) and used between passages 4-20 following thawing. MDA-MB-435 breast carcinoma is maintained and plated in DME/F12 medium containing 10% fetal bovine serum, 15 mM HEPES (pH=7.4), penicillin 100 units/mL, and streptomycin 100 micrograms/mL.

The A549 non-small cell lung lines are obtained from the American Type Culture Collection (ATCC) and used between passages 4-20 following thawing. A549 cells are maintained in RPMI 1640 containing 5% FBS, 5 mg/mL insulin, 5 mg/mL transferring, 5 mg/mL selenous acid, 1 nM β-estradiol, 1 nM testosterone, 100 units/mL penicillin and 100 ug/mL streptomycin.

Cell lines are trypsinized and counted using a Coulter counter to determine plating densities. Cells are then plated in their respective maintenance media (100 μL/well) in 96 well plates at the following densities: MDA-MB-435, 3,000 cells/well; A549, 700 cells/well. The number of cells plates as determined in preliminary experiments, results in cell densities of 75-90% of confluency by 4 days after plating. Initial cell densities, assayed one day after plating, are roughly 0.15-0.20 absorbance units greater than the media blank. Ninety-six well plates are seeded on day 0 and the test compounds are added on day 1. A control plate is created for each cell line that receives media only in row A and cells in row B. One day following plating, test compounds are added (in a final volume of 100 µL) to the test plates. Control plates receive 10 µL MTS mixture (prepared fresh on day of addition to cell plates at a ratio of 10 µL of a 0.92 mg/mL solution of PMS to a 190 µL of a 2 mg/mL solution of MTS) and 100 µL media. $A_{490}$ of control plates is read 4 h after MTS addition to determine initial cell density values for each cell line. Three days after addition of the test compound, 10 µL/well of MTS mixture is added to the test plates and $A_{490}$ is read 4 h later. $A_{490}$ values for wells containing cells are corrected for media absorbance, then normalized to initial density readings to determine percent net growth. $IC_{50}$ values are determined from graphs of percent net growth as a function of compound concentration. Percent net growth is calculated as (Cell+Drug $A_{490}$–initial $A_{490}$/Cell+Drug Vehicle $A_{490}$–initial $A_{490}$).

Each of the compounds of Examples 1-59 shows an $IC_{50}$ value in the range from 0.001 µM to 100 µM in the ADGMA with at least one carcinoma cell line.

What is claimed is:

1. A compound of the formula I:

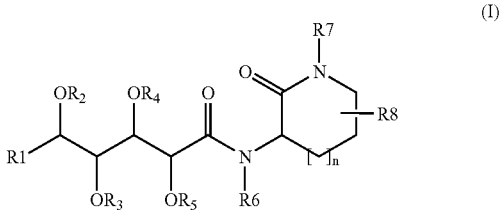

(I)

or a salt thereof, wherein n is 0, 1 or 2;

R1 is H, $X_1$—$(C_{1-6})$alkyl-, $(C_{1-12})$alkylC(O)—, $X_2$—$(C_{2-4})$alkenylene-, $X_2$—$(C_{2-4})$alkynylene-, $X_1$—$(C_{3-9})$cycloalkyl-, $X_2$—$(C_{3-9})$cycloalkene-, $X_1$-aryl-, $X_1$—$(C_{3-7})$cycloalkane-$(C_{1-6})$alkylene-, $X_2$—$(C_{3-7})$cycloalkene-$(C_{1-6})$alkylene-, or $X_1$-aryl-$(C_{1-6})$alkylene-;

$X_1$ is H, $(C_{1-14})$alkyl, $(C_{3-7})$cycloalkyl, $(C_{1-14})$alkyl substituted by $(C_{3-7})$cycloalkyl, —$OR_a$, —$SR_a$, —$NO_2$, halo or $(C_{1-6})$alkylC(O)—; aryl, aryl-$(C_{1-12})$alkyl-, —$OR_a$, —$SR_a$, —$NO_2$, halo, $(C_{1-12})$alkyl-C(O)—, mono- or di-$(C_{1-4})$alkylamino, amino$(C_{1-16})$alkyl-, or mono- or di-$(C_{1-4})$alkylamino$(C_{1-16})$alkyl;

$X_2$ is H, $(C_{1-14})$alkyl, $(C_{3-7})$cycloalkyl, $(C_{1-14})$alkyl substituted by $(C_{3-7})$cycloalkyl, —$OR_a$—$SR_a$, —$NO_2$, halo or $(C_{1-6})$alkyl-C(O)—; aryl, aryl-$(C_{1-12})$alkyl-, amino$(C_{1-16})$alkyl- or mono- or di-$(C_{1-4})$alkylamino$(C_{1-16})$alkyl;

$R_a$ is H, $(C_{1-18})$alkyl, aryl, or $(C_{1-18})$alkyl substituted by $(C_{3-7})$cycloalkyl, aryl, —OH, —O—$(C_{1-16})$alkyl or halo;

R2, R3, R4 and R5 are independently hydrogen or $(C_{1-18})$alkyl, R5 is also phenyl or $(C_{1-6})$alkyl which is substituted by phenyl, wherein there is no more than a total of 18 carbon atoms in the combined R2, R3, R4 and R5 alkyl substituents, or R2 and R4 together or R3 and R5 together form an acetal group;

R6 is hydrogen or $(C_{1-6})$alkyl;

R7 is H, $(C_{1-18})$alkyl, phenyl, pyridyl, $(C_{1-18})$alkyl substituted by $(C_{3-7})$cycloalkyl, —$OR_x$, $N_3$, halo, —$N(R_x)_2$, $R_x$, —O—$(C_{1-6})$alkyl, —OC(O)—$(C_{1-16})$alkyl or pyridyl; —Y—$R_b$ or a substituent of formula IIa or IIIa

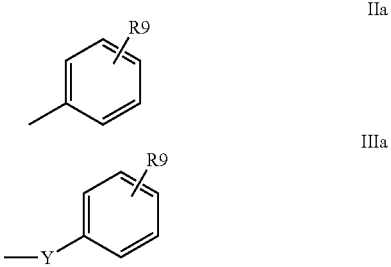

wherein

R9 is from 0 to 3 substituents selected from $(C_{1-6})$alkyl, —$OR_a$, —$SR_a$, —$NO_2$, halo, —$N_3$, $(C_{1-12})$alkylC(O)—, mono- or di-$(C_{1-4})$alkylamino, amino$(C_{1-16})$alkyl-, mono- or di-$(C_{1-4})$alkylamino$(C_{1-16})$alkyl, $(CH_2)_{0-2}$-$C_{5-7}$cycloalkyl, $(CH_2)_{0-2}$-heterocyclic, $(CH_2)_{0-2}$-$C_{5-7}$aryl, or $(CH_2)_{0-2}$-heteroaryl;

Y is a linking group selected from —$(C_{1-10})$alkyl-, —$(C_{0-10})$alkylene-CO—N($R_x$)—$(C_{0-10})$alkylene-, —$(C_{0-10})$alkylene-N($R_x$)—CO—$(C_{0-10})$alkylene-, —$(C_{0-10})$alkylene-CO—O—$(C_{0-10})$alkylene-, —$(C_{1-10})$alkylene-O—C(O)—$(C_{1-10})$alkylene-, —$(C_{0-10})$alkylene-CO—$(C_{0-10})$alkylene-, —$(C_{0-10})$alkylene-$(R_x)$N—CO—O—$(C_{0-10})$alkylene-, —$(C_{0-10})$alkylene-O—CO—$(R_x)$N—$(C_{0-10})$alkylene- or —$(C_{0-18})$alkylene-arylene-$(C_{0-18})$alkylene-;

$R_x$ is H, $(C_{1-4})$alkyl or phenyl;

$R_b$ is $(C_{1-16})$alkyl or $(C_{1-16})$alkyl which is substituted by $(C_{3-7})$cycloalkyl, —$OR_x$, $N_3$, halo, —$N(R_x)_2$, —O—$(C_{1-6})$alkyl, —OC(O)—$(C_{1-16})$alkyl or pyridyl;

R8 is H, halo, —$N_3$, $(C_{1-16})$alkyl, -Z-$(C_{1-16})$alkyl, $(C_{1-15})$alkyl substituted by $(C_{3-7})$cycloalkyl, —$N_3$, —$N(R_x)_2$, -Z-het, —$OR_a$ or —$SR_a$, -Z-$(C_{1-16})$alkyl substituted by $(C_{3-7})$cycloalkyl, —$N_3$, —$N(R_x)_2$, -Z-het, —$OR_a$ or —$SR_a$, —O$(C_{1-16})$alkylene-$N_3$, —O$(C_{1-16})$alkylene-N$(R_x)_2$, —$(C_{0-6})$alkylene-OC(O)—$(C_{1-16})$alkyl, —$(C_{0-6})$alkylene-(O)C—O—$(C_{1-16})$alkyl, —$(C_{0-6})$alkylene-OC(O)—$(C_{3-7})$cycloalkyl, —$(C_{0-6})$alkylene-(O)C—O—$(C_{3-7})$cycloalkyl, pyridyl, —OC(O)O$(C_{1-12})$alkyl, —O—CO—X—$R_z$, or —O—CO—$(CH_2)_m$—O—$(CH_2)_m$—X—$R_z$ wherein X is a direct bond, $(C_{1-12})$alkylene, $(C_{1-12})$alkenylene or $(C_{1-12})$alkynylene and $R_z$ is H, $(C_{3-9})$cycloalkyl, phenyl, phenyl substituted by one or more of chloro, methoxy, $(C_{1-18})$alkyl or $(C_{1-16})$alkoxy, pyrrolyl, furanyl, thiofuranyl, indolyl, benzofuranyl, benzothiofuranyl or pyridyl and each m is independently a number from 0 to 13, -Z-het, —$OR_a$, —$SR_a$, mono- or di-$(C_{1-4})$alkylamino, amino$(C_{1-16})$alkyl-, mono- or di-$(C_{1-4})$alkylamino$(C_{1-16})$alkyl, -Z-Si$((C_{1-6})$alkyl$)_3$ or a substituent selected from the following two formulae:

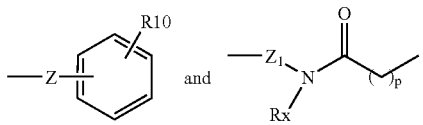

Z is a direct bond, —(C$_{1-12}$)alkylene-, —(C$_{1-12}$)alkylene-O—, —O—(C$_{1-12}$)alkylene-, —(C$_{1-12}$)alkylene-N(R$_x$)—, —N(R$_x$)—, —N(R$_x$)—(C$_{1-12}$)alkylene-, —N(R$_x$)—C(O)—, —N(R$_x$)—C(O)—(C$_{1-12}$)alkylene-, —(C$_{1-12}$)alkylene-N(R$_x$)—C(O)—, —(C$_{1-8}$)alkylene-N(R$_x$)—C(O)—(C$_{1-8}$)alkylene-, —(C$_{1-12}$)alkylene-CO—N(R$_x$)—, —CO—N(R$_x$)—(C$_{1-12}$)alkylene-, —(C$_{1-8}$)alkylene-CO—N(R$_x$)—(C$_{1-8}$)alkylene-, —CO—N(R$_x$)—, —(C$_{1-12}$)alkylene-CO—O—, —(C$_{1-12}$)alkylene-O—C(O)—, —OC(O)—(C$_{1-12}$)alkylene-, —C(O)—(C$_{1-12}$)alkylene-, —(C$_{1-12}$)alkylene-CO—, —(C$_{1-8}$)alkylene-CO—(C$_{1-8}$)alkylene-, —CO—(C$_{1-12}$)alkylene-, —C(O)—, —N(R$_x$)—C(O)—O—, —N(R$_x$)—C(O)—O—(C$_{1-12}$)alkylene-, —(C$_{1-12}$)alkylene-N(R$_x$)—C(O)—O—, —(C$_{1-8}$)alkylene-N(R$_x$)—C(O)—O—(C$_{1-8}$)alkylene-, —(C$_{1-12}$)alkylene-O—CO—N(R$_x$)—, —O—CO—N(R$_x$)—(C$_{1-12}$)alkylene-, —(C$_{1-8}$)alkylene-O—CO—N(R$_x$)—(C$_{1-8}$)alkylene-, —O—CO—N(R$_x$)—, —O—CO—O—, —(C$_{1-12}$)alkylene-O—CO—O—, —O—CO—O—(C$_{1-12}$)alkylene- or —(C$_{1-8}$)alkylene-O—C(O)—O—(C$_{1-8}$)alkylene-, Z$_1$ is a direct bond, —(C$_{1-12}$)alkylene-, —O—(C$_{1-12}$)alkylene-, —N(R$_x$)—(C$_{1-12}$)alkylene-, —N(R$_x$)—C(O)—(C$_{1-12}$)alkylene-, —(C$_{1-8}$)alkylene-N(R$_x$)—C(O)—(C$_{1-8}$)alkylene-, —CO—N(R$_x$)—(C$_{1-12}$)alkylene-, —(C$_{1-6}$)alkylene-CO—N(R$_x$)—(C$_{1-8}$)alkylene-, —OC(O)—(C$_{1-12}$)alkylene-, —C(O)—O—(C$_{1-12}$)alkylene-, —(C$_{1-8}$)alkylene-CO—(C$_8$)alkylene-, —CO—(C$_{1-12}$)alkylene-, —C(O)—, —N(R$_x$)—C(O)—O—(C$_{1-12}$)alkylene-, —(C$_{1-8}$)alkylene-N(R$_x$)—C(O)—O—(C$_{1-8}$)alkylene-, —O—CO—N(R$_x$)—(C$_{1-12}$)alkylene-, —(C$_{1-8}$)alkylene-O—CO—N(R$_x$)—(C$_{1-8}$)alkylene-, —O—CO—O—(C$_{1-12}$)alkylene- or —(C$_{1-8}$)alkylene-O—C(O)—O—(C$_{1-8}$)alkylene-;

R10 is from 0 to 3 substituents selected from hydroxy, halo, —(C$_{1-17}$)alkyl, —O—(C$_{1-17}$)alkyl, —(CH$_2$)$_{1-6}$-C$_{3-7}$-cycloalkyl, —(CH$_2$)$_{0-10}$-aryl or —(CH$_2$)$_{0-10}$-het;

het is a heterocyclic or heteroaromatic ring;

p is 1-18;

with the proviso that when n is 2 and R$_1$ is (C$_{1-6}$)alkyl-CH═CH— or (C$_{3-6}$)cycloalkyl-CH═CH— then R$_7$ is not H or (C$_{1-8}$)alkyl or R$_8$ is not —O—CO—X—R$_Z$ or —O—CO—(CH$_2$)$_m$—O—(CH$_2$)$_m$—X—R$_z$ where X is a direct bond, (C$_{1-12}$)alkylene, (C$_{1-12}$)alkenylene or (C$_{1-12}$)alkynylene and R$_z$ is H, (C$_{3-9}$)cycloalkyl, phenyl, phenyl substituted by one or more of chloro, methoxy, (C$_{1-18}$)alkyl or (C$_{1-18}$)alkoxy, pyrrolyl, furanyl, thiofuranyl, indolyl, benzofuranyl, benzothiofuranyl or pyridyl and each m is independently a number from 0 to 13, and with the further proviso that R$_8$ is not —OH when n is 2, R$_7$ is H or methyl and R$_1$ is 3-methylbut-1-enylene.

2. A compound as claimed in claim 1, or a salt thereof, wherein:

n is 2;

R1 is X$_1$—(C$_{1-6}$)alkyl-, X$_2$—(C$_{2-4}$)alkenylene-, X$_1$—(C$_{3-7}$)cycloalkyl-, or X$_1$—(C$_{3-7}$)cycloalkane-(C$_{1-3}$)alkylene-;

X$_1$ is H, (C$_{1-12}$)alkyl, (C$_{3-7}$)cycloalkyl, —(C$_{1-12}$)alkyl substituted by (C$_{3-7}$)cycloalkyl, —OR$_a$; —SR$_a$, —NO$_2$, halo or (C$_{1-12}$)alkylC(O)—; aryl, aryl-(C$_{1-12}$)alkyl- or —OR$_a$;

X$_2$ is H, (C$_{1-12}$)alkyl, (C$_{3-7}$)cycloalkyl, —(C$_{1-12}$)alkyl substituted by (C$_{3-7}$)cycloalkyl, —OR$_a$, —SR$_a$, —NO$_2$, halo or (C$_{1-12}$)alkylC(O)—, aryl, aryl-(C$_{1-12}$)alkyl-;

R$_a$ is H, (C$_{1-18}$)alkyl, aryl-, or (C$_{1-18}$)alkyl substituted by (C$_{3-7}$)cycloalkyl or aryl;

R$_2$, R$_3$, R$_4$ and R$_5$ are independently hydrogen or (C$_{1-4}$)alkyl, wherein there is no more than a total of 8 carbon atoms, especially no more than 4 carbon atoms, in the combined R$_2$, R$_3$, R$_4$ and R$_5$ alkyl substituents;

R6 is hydrogen or (C$_{1-4}$) alkyl;

R7 is H, (C$_{1-8}$)alkyl, R$_x$, (C$_{1-18}$)alkyl substituted by (C$_{3-7}$)cycloalkyl, —OR$_x$, N$_3$, halo, —N(R$_x$)$_2$, —O—(C$_{1-6}$)alkyl, —OC(O)—(C$_{1-16}$)alkyl or pyridyl; or a substituent of formula IIa or IIIa

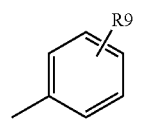

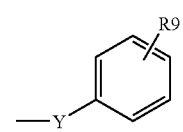

R9 is from 0 to 3 substituents selected from (C$_{1-6}$)alkyl, —OR$_a$, —SR$_a$, —NO$_2$, halo, or —N$_3$;

Y is a linking group selected from —C(O)N(R$_x$)—, —CO—O—, —(C$_{1-12}$)alkylene-CO—O—, —CO—O—(C$_{1-12}$)alkylene-, —(C$_{1-10}$)alkylene-CO—O—(C$_{1-10}$)alkylene-, —(C$_{1-10}$)alkylene-O—C(O)—(C$_{1-10}$)alkylene-, —CO—, —(C$_{1-12}$)alkylene-CO—, —CO—(C$_{1-12}$)alkylene-, —(C$_{1-10}$)alkylene-CO—(C$_{1-10}$)alkylene-, —(C$_{1-12}$)alkylene-(R$_x$)N—CO—, —(C$_{1-10}$)alkylene-(R$_x$)N—CO—O—(C$_{1-10}$)alkylene-, or —(C$_{0-12}$)alkylene-arylene-(C$_{0-12}$)alkylene-;

R$_x$ is H, (C$_{1-4}$)alkyl or phenyl;

R8 is —N$_3$, (C$_{1-16}$)alkyl, -Z-(C$_{1-16}$)alkyl, (C$_{1-16}$)alkyl substituted by (C$_{3-7}$)cycloalkyl, —N$_3$, or —N(R$_x$)$_2$; -Z-(C$_{1-16}$)alkyl substituted in the alkyl portion by (C$_{3-7}$)cycloalkyl, —N$_3$, or —N(R$_x$)$_2$, —(C$_{0-6}$)alkylene-(O)C—O—(C$_{1-16}$)alkyl, or a substituent selected from the following two formulae:

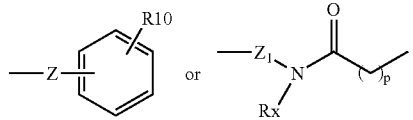

Z is a direct bond, —(C$_{1-12}$)alkylene-, —N(R$_x$)—C(O)—, —N(R$_x$)—C(O)—(C$_{1-12}$)alkylene-, —(C$_{1-12}$)alkylene-N(R$_x$)—C(O)—, —(C$_{1-8}$)alkylene-N(R$_x$)—C(O)—(C$_{1-8}$)alkylene-, —(C$_{1-12}$)alkylene-CO—N(R$_x$)—, —CO—N(R$_x$)—(C$_{1-12}$)alkylene-, —(C$_{1-8}$)alkylene-CO—N(R$_x$)—(C$_{1-8}$)alkylene-, —CO—N(R$_x$)—, —C(O)—O—(C$_{1-12}$)alkylene-, —CO—(C$_{1-12}$)alkylene-, —C(O)—, —N(R$_x$)—C(O)—O—, —N(R$_x$)—C(O)—O—(C$_{1-12}$)alkylene-, —(C$_{1-12}$)alkylene-N(R$_x$)—C(O)—O—, —(C$_{1-8}$)alkylene-N(R$_x$)—C(O)—O—

(C$_{1-8}$)alkylene-, —(C$_{1-12}$)alkylene-O—CO—N(R$_x$)—, —O—CO—N(R$_x$)—(C$_{1-12}$)alkylene-, —(C$_{1-8}$)alkylene-O—CO—N(R$_x$)—(C$_{1-8}$)alkylene- or —O—CO—N(R$_x$)—;

Z$_1$ is a direct bond, —(C$_{1-12}$)alkylene- or —C(O)—;

R10 is from 0 to 3 substituents selected from hydroxy, halo, —(C$_{1-17}$)alkyl, —O—(C$_{1-17}$)alkyl, —(CH$_2$)$_{1-6}$-C$_{3-7}$-cycloalkyl, —(CH$_2$)$_{0-10}$-aryl or —(CH$_2$)$_{0-10}$-het; and het is pyridyl.

3. A compound as claimed in claim 1, or a salt thereof, wherein:

R1 is (C$_{1-6}$ alkyl)-ethenylene-;

R$_2$, R$_3$ and R$_4$, independently are hydrogen or (C$_{1-4}$) alkyl, wherein there is no more than a total of 4 carbon atoms in the combined R$_2$, R$_3$, R$_4$ and R$_5$ alkyl substituents;

R$_5$ is (C$_{1-4}$)alkyl;

R6 is hydrogen or methyl;

R7 is H or (C$_{1-6}$)alkyl;

R8 is H, —N$_3$, (C$_{1-16}$)alkyl, -Z-(C$_{1-16}$)alkyl, (C$_{1-16}$)alkyl substituted by (C$_{3-7}$)cycloalkyl, —N$_3$, or —N(R$_x$)$_2$; or -Z-(C$_{1-16}$)alkyl substituted in the alkyl portion by (C$_{3-7}$)cycloalkyl, —N$_3$, or —N(R$_x$)$_2$;

R9 is (CH$_2$)$_{0-2}$-C$_{5-7}$ cycloalkyl, (CH$_2$)$_{0-2}$-C$_{5-7}$ hetero-cyclic, (CH$_2$)$_{0-2}$-C$_{5-7}$ aryl, or (CH$_2$)$_{0-2}$-C$_{5-7}$ hetero-aryl;

X is (C$_{1-12}$)alkylene or (C$_{2-12}$) alkenylene;

R10 is from 0 to 3 substituents selected from hydroxy, halo, —(C$_{1-8}$)alkyl, —O—(C$_{1-6}$)alkyl, —(CH$_2$)$_{1-6}$-C$_{3-7}$-cycloalkyl, —(CH$_2$)$_{0-10}$-aryl or —(CH$_2$)$_{0-10}$-het;

het is pyridyl;

n is 2.

4. A compound as claimed in claim 1, or a salt thereof, wherein:

R1 is —CH═CH-i-propyl or —CH═CH-t-butyl;

X$_2$ is H;

R$_2$, R$_3$, R$_4$, and R$_5$ independently are hydrogen or methyl;

R6 is hydrogen;

R7 is H or (C$_{1-3}$)alkyl; and n is 2.

5. A compound as claimed in claim 1, or a salt thereof, wherein:

R$_1$ is X$_1$—(C$_{3-7}$)cycloalkane-(C$_{1-6}$)alkylene- or X$_2$—(C$_{3-9}$)cycloalkene-;

X$_1$ is hydrogen;

X$_2$ is hydrogen;

R$_2$, R$_3$, R$_4$, and R$_5$ independently are hydrogen or methyl;

R$_6$ is hydrogen;

R$_7$ is H or (C$_{1-3}$) alkyl;

R$_8$ is hydrogen; and n is 2.

6. A pharmaceutical composition comprising a compound of formula I according to claim 1, or a pharmaceutically acceptable salt thereof, and a pharmaceutically acceptable carrier or diluent.

7. A process to prepare the compound of the formula I:

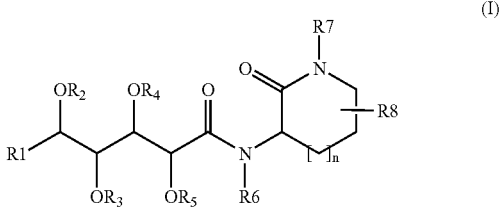

(I)

or a salt thereof, wherein n is 0, 1 or 2;

R1 is H, X$_1$—(C$_{1-6}$)alkyl-, (C$_{1-12}$)alkylC(O)—, X$_2$—(C$_{2-4}$)alkenylene-, X$_2$—(C$_{2-4}$)alkynylene-, X$_1$—(C$_{3-9}$)cycloalkyl-, X$_2$—(C$_{3-9}$)cycloalkene-, X$_1$-aryl-, X$_1$—(C$_{3-7}$)cycloalkane-(C$_{1-6}$)alkylene-, X$_2$—(C$_{3-7}$)cycloalkene-(C$_{1-6}$)alkylene-, or X$_1$-aryl-(C$_{1-6}$)alkylene-;

X$_1$ is H, (C$_{1-14}$)alkyl, (C$_{3-7}$)cycloalkyl, (C$_{1-14}$)alkyl substituted by (C$_{3-7}$)cycloalkyl, —OR$_a$, —SR$_a$, —NO$_2$, halo or (C$_{1-6}$)alkylC(O)—; aryl, aryl-(C$_{1-12}$)alkyl-, —OR$_a$, —SR$_a$, —NO$_2$, halo, (C$_{1-12}$)alkyl-C(O)—, mono- or di-(C$_{1-4}$)alkylamino, amino(C$_{1-16}$)alkyl-, or mono- or di-(C$_{1-4}$)alkylamino(C$_{1-16}$)alkyl;

X$_2$ is H, (C$_{1-14}$)alkyl, (C$_{3-7}$)cycloalkyl, (C$_{1-14}$)alkyl substituted by (C$_{3-7}$)cycloalkyl, —OR$_a$—SR$_a$, —NO$_2$, halo or (C$_{1-6}$)alkyl-C(O)—; aryl, aryl-(C$_{1-12}$)alkyl-, amino(C$_{1-16}$)alkyl- or mono- or di-(C$_{1-4}$)alkylamino (C$_{1-16}$)alkyl;

R$_a$ is H, (C$_{1-18}$)alkyl, aryl, or (C$_{1-18}$)alkyl substituted by (C$_{3-7}$)cycloalkyl, aryl, —OH, —O—(C$_{1-6}$)alkyl or halo;

R$_2$, R$_3$, R$_4$ and R$_5$ are independently hydrogen or (C$_{1-18}$) alkyl, R$_5$ is also phenyl or (C$_{1-16}$)alkyl which is substituted by phenyl, wherein there is no more than a total of 18 carbon atoms in the combined R$_2$, R$_3$, R$_4$ and R$_5$ alkyl substituents, or R$_2$ and R$_4$ together or R$_3$ and R$_5$ together form an acetal group;

R6 is hydrogen or (C$_{1-6}$)alkyl;

R7 is H, (C$_{1-18}$)alkyl, phenyl, pyridyl, (C$_{1-18}$)alkyl substituted by (C$_{3-7}$)cycloalkyl, —OR$_x$, N$_3$, halo, —N(R$_x$)$_2$, R$_x$, —O—(C$_{1-6}$)alkyl, —OC(O)—(C$_{1-16}$)alkyl or pyridyl; —Y—R$_b$ or a substituent of formula IIa or IIIa

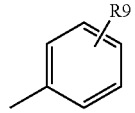

IIa

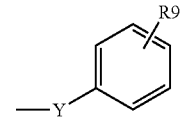

IIIa wherein

R9 is from 0 to 3 substituents selected from (C$_{1-6}$)alkyl, —OR$_a$, —SR$_a$, —NO$_2$, halo, —N$_3$, (C$_{1-12}$)alkylC(O)—, mono- or di-(C$_{1-4}$)alkylamino, amino(C$_{1-16}$) alkyl-, mono- or di-(C$_{1-4}$)alkylamino(C$_{1-16}$)alkyl, (CH$_2$)$_{0-2}$-C$_{5-7}$cycloalkyl, (CH$_2$)$_{0-2}$-heterocyclic, (CH$_2$)$_{0-2}$-C$_{5-7}$aryl, or (CH$_2$)$_{0-2}$-heteroaryl;

Y is a linking group selected from —(C$_{1-10}$)alkyl-, —(C$_{0-10}$)alkylene-CO—N(R$_x$)—(C$_{0-10}$)alkylene-, —(C$_{0-10}$)alkylene-N(R$_x$)-CO—(C$_{0-10}$)alkylene-, —(C$_{0-10}$)alkylene-CO—O—(C$_{0-10}$)alkylene-, —(C$_{1-10}$)alkylene-O—C(O)—(C$_{1-10}$)alkylene-, —(C$_{0-10}$)alkylene-CO—(C$_{0-10}$)alkylene-, —(C$_{0-10}$) alkylene-(R$_x$)N—CO—O—(C$_{0-10}$)alkylene-, —(C$_{0-10}$) alkylene-O—CO—(R$_x$)N—(C$_{0-10}$)alkylene- or —(C$_{0-18}$)alkylene-arylene-(C$_{0-18}$)alkylene-;

R$_x$ is H, (C$_{1-4}$)alkyl or phenyl;

R$_b$ is (C$_{1-16}$)alkyl or (C$_{1-16}$)alkyl which is substituted by (C$_{3-7}$)cycloalkyl, —OR$_x$, N$_3$, halo, —N(R$_x$)$_2$, —O—(C$_{1-6}$)alkyl, —OC(O)—(C$_{1-16}$)alkyl or pyridyl;

R8 is H, halo, —N$_3$, (C$_{1-16}$)alkyl, -Z-(C$_{1-16}$)alkyl, (C$_{1-16}$) alkyl substituted by (C$_{3-7}$)cycloalkyl, —N$_3$, —N(R$_x$)$_2$, -Z-het, —OR$_a$ or —SR$_a$, -Z-(C$_{1-16}$)alkyl substituted by (C$_{3-7}$)cycloalkyl, —N$_3$, —N(R$_x$)$_2$, -Z-het, —OR$_a$ or —SR$_a$, —O(C$_{1-16}$)alkylene-N$_3$, —O(C$_{1-16}$) alkylene-N(R$_x$)$_2$, —(C$_{0-6}$)alkylene-OC(O)—(C$_{1-16}$) alkyl, —(C$_{0-6}$)alkylene-(O)C—O—(C$_{1-16}$)alkyl, —(C$_{0-6}$)alkylene-OC(O)—(C$_{3-7}$)cycloalkyl, —(C$_{0-6}$) alkylene-(O)C—O—(C$_{3-7}$)cycloalkyl, pyridyl, —OC(O)O(C$_{1-12}$)alkyl, —O—CO—X—R$_z$, or —O—CO—(CH$_2$)$_m$—O—(CH$_2$)$_m$—X—R$_z$ wherein X is a direct bond, (C$_{1-12}$)alkylene, (C$_{1-12}$)alkenylene or (C$_{1-12}$) alkynylene and R$_z$ is H, (C$_{3-9}$)cycloalkyl, phenyl, phenyl substituted by one or more of chloro, methoxy, (C$_{1-18}$)alkyl or (C$_{1-18}$)alkoxy, pyrrolyl, furanyl, thiofuranyl, indolyl, benzofuranyl, benzothiofuranyl or pyridyl and each m is independently a number from 0 to 13, -Z-het, —OR$_a$, —SR$_a$, mono- or di-(C$_{1-4}$)alkylamino, amino(C$_{1-16}$)alkyl-, mono- or di-(C$_{1-4}$)alkylamino(C$_{1-16}$)alkyl, -Z-Si((C$_{1-6}$)alkyl)$_3$ or a substituent selected from the following two formulae:

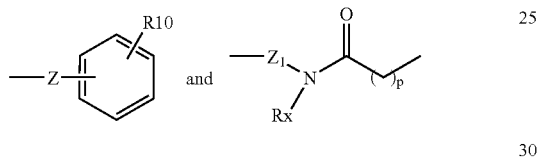

Z is a direct bond, —(C$_{1-12}$)alkylene-, —(C$_{1-12}$)alkylene-O—, —O—(C$_{1-12}$)alkylene-, —(C$_{1-12}$)alkylene-N(R$_x$)—, —N(R$_x$)—, —N(R$_x$)—(C$_{1-12}$)alkylene-, —N(R$_x$)—C(O)—, —N(R$_x$)—C(O)—(C$_{1-12}$)alkylene-, —(C$_{1-12}$)alkylene-N(R$_x$)—C(O)—, —(C$_{1-8}$)alkylene-N(R$_x$)—C(O)—(C$_{1-8}$)alkylene-, —(C$_{1-12}$) alkylene-CO—N(R$_x$)—, —CO—N(R$_x$)—(C$_{1-12}$) alkylene-, —(C$_{1-8}$)alkylene-CO—N(R$_x$)—(C$_{1-8}$) alkylene-, —CO—N(R$_x$)—, —(C$_{1-12}$)alkylene-CO—O—, —(C$_{1-12}$)alkylene-O—C(O)—, —OC(O)—(C$_{1-12}$)alkylene-, —C(O)—O—(C$_{1-12}$)alkylene-, —(C$_{1-12}$)alkylene-CO—, —(C$_{1-8}$)alkylene-CO—(C$_{1-8)}$)alkylene-, —CO—(C$_{1-12}$)alkylene—C(O)—, —N(R$_x$)—C(O)—O—, —N(R$_x$)—C(O)—(C$_{1-12}$)alkylene-, —(C$_{1-12}$)alkylene-N(R$_x$)—C(O)—O—, —(C$_{1-8}$) alkylene-N(R$_x$)—C(O)—O—(C$_{1-8}$)alkylene-, —(C$_{1-12}$)alkylene-O—CO—N(R$_x$)—, —O—CO—N(R$_x$)—(C$_{1-12}$)alkylene-, —(C$_{1-8}$)alkylene-O—CO—N(R$_x$)—(C$_{1-8}$)alkylene-, —O—CO—N(R$_x$)—, —O—CO—O—, —(C$_{1-12}$)alkylene-O—CO—O—, —O—CO—O—(C$_{1-12}$)alkylene- or —(C$_{1-8}$)alkylene-O—C(O)—O—(C$_{1-8}$)alkylene-, Z$_1$ is a direct bond, —(C$_{1-12}$)alkylene-, —O—(C$_{1-12}$) alkylene-, —N(R$_x$)—(C$_{1-12}$)alkylene-, —N(R$_x$)—C(O)—(C$_{1-12}$)alkylene-, —(C$_{1-8}$)alkylene-N(R$_x$)—C(O)—(C$_{1-8}$)alkylene-, —CO—N(R$_x$)—(C$_{1-12}$) alkylene-, —(C$_{1-8}$)alkylene-CO—N(R$_x$)—(C$_{1-8}$) alkylene-, —OC(O)—(C$_{1-12}$)alkylene-, —C(O)—O—(C$_{1-12}$)alkylene-, —(C$_{1-8}$)alkylene-CO—(C$_{1-8)}$) alkylene-, —CO—(C$_{1-12}$)alkylene-, —C(O)—, —N(R$_x$)—C(O)—O—(C$_{1-12}$)alkylene-, —(C$_{1-8}$)alkylene-N(R$_x$)—C(O)—O—(C$_{1-8}$)alkylene-, —O—CO—N(R$_x$)—(C$_{1-12}$)alkylene-, —(C$_{1-8}$)alkylene-O—CO—N(R$_x$)—(C$_{1-8}$)alkylene-, —O—CO—O—(C$_{1-12}$) alkylene- or —(C$_{1-8}$)alkylene-O—C(O)—O—(C$_{1-8}$) alkylene-;

R10 is from 0 to 3 substituents selected from hydroxy, halo, —(C$_{1-17}$)alkyl, —O—(C$_{1-17}$)alkyl, —(CH$_2$)$_{1-6}$-C$_{3-7}$-cycloalkyl, —(CH$_2$)$_{0-10}$-aryl or —(CH$_2$)$_{0-10}$-het;

het is a heterocyclic or heteroaromatic ring;

p is 1-18;

with the proviso that when n is 2 and R$_1$ is (C$_{1-6}$)alkyl-CH═CH— or (C$_{3-6}$)cycloalkyl-CH═CH— then R$_7$ is not H or (C$_{1-8}$)alkyl or R$_8$ is not —O—CO—X—R$_z$ or —O—CO—(CH$_2$)$_m$—O—(CH$_2$)$_m$—X—R$_z$ where X is a direct bond, (C$_{1-12}$)alkylene, (C$_{1-12}$)alkenylene or (C$_{1-12}$)alkynylene and R$_z$ is H, (C$_{3-9}$)cycloalkyl, phenyl, phenyl substituted by one or more of chloro, methoxy, (C$_{1-18}$)alkyl or (C$_{1-18}$)alkoxy, pyrrolyl, furanyl, thiofuranyl, indolyl, benzofuranyl, benzothiofuranyl or pyridyl and each m is independently a number from 0 to 13, and with the further proviso that R$_8$ is not —OH when n is 2, R$_7$ is H or methyl and R$_1$ is 3-methylbut-1-enylene;

comprising the following steps:

(a) reacting the compound of formula VI or an acid addition salt thereof

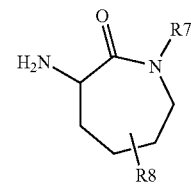

wherein R$_7$ and R$_8$ are defined above, with the compound of formula VII

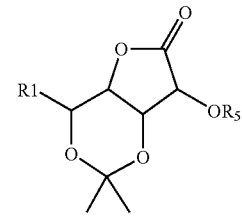

wherein R$_1$ and R$_5$ are defined above, to form a compound of formula VIII

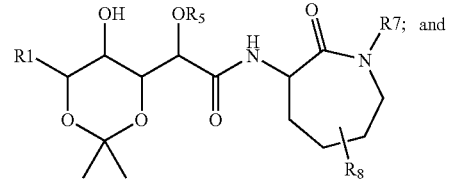

(b) hydrolyzing the compound of formula VIII.

8. The process as claimed in claim 7, wherein step (a) is conducted in a polar organic solvent or in the presence of a weak base and a polar organic solvent.

9. The process as claimed in claim 7, wherein the compound of VIII is prepared by reacting the compound of XI

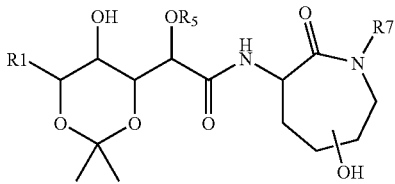

wherein $R_1$, $R_5$ and $R_7$ are defined in claim 7, with an acid chloride in the presence of a base and a solvent.

10. The process as claimed in claim 9, wherein the acid chloride is of the formula $R_{12}COCl$, wherein $R_{12}$ is an appropriate substituent based on the definition of $R_8$; the base is triethylamine and the solvent is dichloromethane.

11. The process as claimed in claim 7, wherein the compound of VIII is prepared by reacting the compound of XI

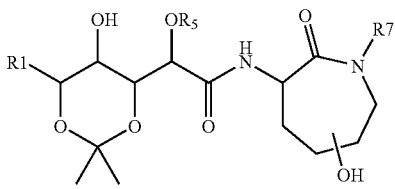

wherein $R_1$, $R_5$ and $R_7$ are defined in claim 8, with a carboxylic acid in the presence of a carboxylic acid coupling agent and an activating agent.

12. The process as claimed in claim 11, wherein the carboxylic acid is of the formula $R_{12}COOH$ wherein $R_{12}$ is an appropriate substituent based on the definition of $R_8$; the carboxylic acid coupling reagent is 1-(3-dimethylaminopropyl)-3-ethylcarbodiimide hydrochloride and the activating agent is 4-dimethylaminopyridine.

13. The process as claimed in claim 7 wherein the compound of formula VII is prepared by cleaving the compound of formula XXXIII

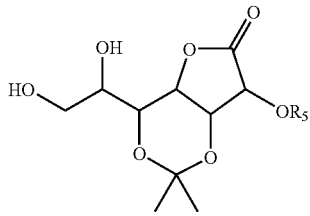

wherein $R_5$ is defined in claim 7, to obtain the compound XXXIV

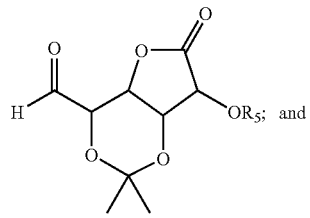

reacting the compound of XXXIV with an organometallic compound in the presence of a solvent mixture.

14. The process as claimed in claim 13, wherein cleaving the compound of formula XXXIII is carried out in the presence of a periodate salt in a solvent.

15. The process as claimed in claim 14, wherein the periodate salt is sodium periodate and the solvent is methanol.

16. The process as claimed in claim 13, wherein the organometallic compound is an organochromium compound, and the solvent mixture comprises of a polar organic solvent and an inert organic solvent.

17. The process as claimed in claim 16, wherein the polar organic solvent is N,N-dimethylformamide and the inert organic solvent is tetrahydrofuran.

18. A process to prepare the compound of the formula I:

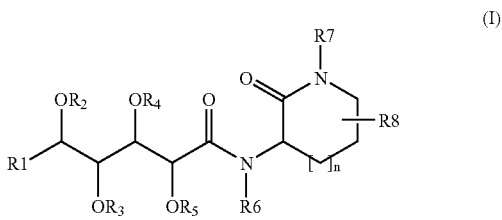

or a salt thereof, wherein n is 0, 1 or 2;

R1 is H, $X_1$—$(C_{1-6})$alkyl-, $(C_{1-12})$alkylC(O)—, $X_2$—$(C_{2-4})$alkenylene-, $X_2$—$(C_{2-4})$alkynylene-, $X_1$—$(C_{3-9})$cycloalkyl-, $X_2$—$(C_{3-9})$cycloalkene-, $X_1$-aryl-, $X_1$—$(C_{3-7})$cycloalkane-$(C_{1-6})$alkylene-, $X_2$—$(C_{3-7})$cycloalkene-$(C_{1-6})$alkylene-, or $X_1$-aryl-$(C_{1-6})$alkylene-;

$X_1$ is H, $(C_{1-4})$alkyl, $(C_{3-7})$cycloalkyl, $(C_{1-14})$alkyl substituted by $(C_{3-7})$cycloalkyl, —$OR_a$, —$SR_a$, —$NO_2$, halo or $(C_{1-6})$alkylC(O)—; aryl, aryl-$(C_{1-12})$alkyl-, $OR_a$, —$SR_a$, —$NO_2$, halo, $(C_{1-12})$alkyl-C(O)—, mono- or di-$(C_{1-4})$alkylamino, amino$(C_{1-16})$alkyl-, or mono- or di-$(C_{1-4})$alkylamino$(C_{1-16})$alkyl;

$X_2$ is H, $(C_{1-14})$alkyl, $(C_{3-7})$cycloalkyl, $(C_{1-14})$alkyl substituted by $(C_{3-7})$cycloalkyl, —$OR_a$—$SR_a$, —$NO_2$, halo or $(C_{1-6})$alkyl-C(O)—; aryl, aryl-$(C_{1-12})$alkyl-, amino$(C_{1-16})$alkyl- or mono- or di-$(C_{1-4})$alkylamino $(C_{1-16})$alkyl;

$R_a$ is H, $(C_{1-18})$alkyl, aryl, or $(C_{1-18})$alkyl substituted by $(C_{3-7})$cycloalkyl, aryl, —OH, —O—$(C_{1-6})$alkyl or halo;

$R_2$, $R_3$, $R_4$ and $R_5$ are independently hydrogen or $(C_{1-18})$alkyl, $R_5$ is also phenyl or $(C_{1-16})$alkyl which is substituted by phenyl, wherein there is no more than a total of 18 carbon atoms in the combined $R_2$, $R_3$, $R_4$ and $R_5$ alkyl substituents, or $R_2$ and $R_4$ together or $R_3$ and $R_5$ together form an acetal group;

R6 is hydrogen or $(C_{1-6})$alkyl;

R7 is H, $(C_{1-18})$alkyl, phenyl, pyridyl, $(C_{1-18})$alkyl substituted by $(C_{3-7})$cycloalkyl, —$OR_x$, $N_3$, halo, —N$(R_x)_2$, $R_x$, —O—$(C_{1-6})$alkyl, —OC(O)—$(C_{1-16})$alkyl or pyridyl; —Y—$R_b$ or a substituent of formula IIa or IIIa

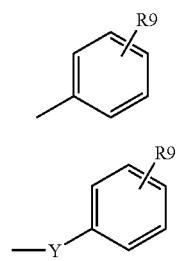

IIa

IIIa wherein
R9 is from 0 to 3 substituents selected from $(C_{1-6})$alkyl, $-OR_a$, $-SR_a$, $-NO_2$, halo, $-N_3$, $(C_{1-12})$alkylC(O)—, mono- or di-$(C_{1-4})$alkylamino, amino$(C_{1-16})$alkyl-, mono- or di-$(C_{1-4})$alkylamino$(C_{1-16})$alkyl, $(CH_2)_{0-2}$-$C_{5-7}$cycloalkyl, $(CH_2)_{0-2}$-heterocyclic, $(CH_2)_{0-2}$-$C_{5-7}$aryl, or $(CH_2)_{0-2}$-heteroaryl;

Y is a linking group selected from $-(C_{1-10})$alkyl-, $-(C_{0-10})$alkylene-CO$-$N$(R_x)$$-$(C_{8-10})$alkylene-, $-(C_{0-10})$alkylene-N$(R_x)$$-$CO$-$(C_{0-10})$alkylene-, $-(C_{0-10})$alkylene-CO$-$O$-$(C_{0-10})$alkylene-, $-(C_{1-10})$alkylene-O$-$C(O)$-$(C_{1-10})$alkylene-, $-(C_{0-10})$alkylene-CO$-$(C_{0-10})$alkylene-, $-(C_{0-10})$alkylene-$(R_x)$N$-$CO$-$O$-$(C_{0-10})$alkylene-, $-(C_{0-10})$alkylene-O$-$CO$-$$(R_x)$N$-$(C_{0-10})$alkylene- or $-(C_{0-18})$alkylene-arylene-$(C_{0-18})$alkylene-;

$R_x$ is H, $(C_{1-4})$alkyl or phenyl;

$R_b$ is $(C_{1-16})$alkyl or $(C_{1-16})$alkyl which is substituted by $(C_{3-7})$cycloalkyl, $-OR_x$, $N_3$, halo, $-N(R_x)_2$, $-O-(C_{1-6})$alkyl, $-OC(O)-(C_{1-16})$alkyl or pyridyl;

R8 is H, halo, $-N_3$, $(C_{1-16})$alkyl, -Z-$(C_{1-16})$alkyl, $(C_{1-16})$alkyl substituted by $(C_{3-7})$cycloalkyl, $-N_3$, $-N(R_x)_2$, -Z-het, $-OR_a$ or $-SR_a$, -Z-$(C_{1-16})$alkyl substituted by $(C_{3-7})$cycloalkyl, $-N_3$, $-N(R_x)_2$, -Z-het, $-OR_a$ or $-SR_3$, $-O(C_{1-16})$alkylene-$N_3$, $-O(C_{1-16})$alkylene-$N(R_x)_2$, $-(C_{0-6})$alkylene-OC(O)$-$(C_{1-16})$alkyl, $-(C_{0-6})$alkylene-(O)C$-$O$-$(C_{1-16})$alkyl, $-(C_{0-6})$alkylene-OC(O)$-$(C_{3-7})$cycloalkyl, $-(C_{0-6})$alkylene-(O)C$-$O$-$(C_{3-7})$cycloalkyl, pyridyl, $-$OC(O)O$(C_{1-12})$alkyl, $-$O$-$CO$-$X$-$R_z$, or $-$O$-$CO$-$(CH_2)_m$-$O$-$(CH_2)_m$-$X$-$R_z$ wherein X is a direct bond, $(C_{1-12})$alkylene, $(C_{1-12})$alkenylene or $(C_{1-12})$alkynylene and $R_z$ is H, $(C_{3-9})$cycloalkyl, phenyl, phenyl substituted by one or more of chloro, methoxy, $(C_{1-18})$alkyl or $(C_{1-18})$alkoxy, pyrrolyl, furanyl, thiofuranyl, indolyl, benzofuranyl, benzothiofuranyl or pyridyl and each m is independently a number from 0 to 13, -Z-het, $-OR_a$, $-SR_a$, mono- or di-$(C_{1-4})$alkylamino, amino$(C_{1-16})$alkyl-, mono- or di-$(C_{1-4})$alkylamino$(C_{1-16})$alkyl, -Z-Si$((C_{1-6})$alkyl$)_3$ or a substituent selected from the following two formulae:

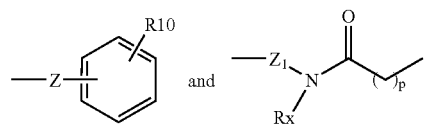 and 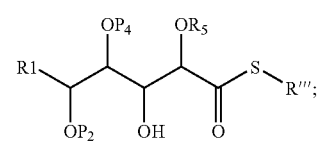

Z is a direct bond, $-(C_{1-12})$alkylene-, $-(C_{1-12})$alkylene-O—, $-$O$-(C_{1-12})$alkylene-, $-(C_{1-12})$alkylene-N$(R_x)$—, $-$N$(R_x)$—, $-$N$(R_x)$$-(C_{1-12})$alkylene-, $-$N$(R_x)$$-$C(O)—, $-$N$(R_x)$$-$C(O)$-(C_{1-12})$alkylene-, $-(C_{1-12})$alkylene-N$(R_x)$$-$C(O)—, $-(C_{1-8})$alkylene-N$(R_x)$$-$C(O)$-(C_{1-8})$alkylene-, $-(C_{1-12})$alkylene-CO$-$N$(R_x)$—, $-$CO$-$N$(R_x)$$-(C_{1-12})$alkylene-, $-(C_{1-8})$alkylene-CO$-$N$(R_x)$$-(C_{1-8})$alkylene-, $-$CO$-$N$(R_x)$—, $-(C_{1-12})$alkylene-CO$-$O—, $-(C_{1-12})$alkylene-O$-$C(O)—, $-$OC(O)$-(C_{1-12})$alkylene-, $-$C(O)$-$O$-(C_{1-12})$alkylene-, $-(C_{1-12})$alkylene-CO—, $-(C_{1-8})$alkylene-CO$-(C_{1-8})$alkylene-, $-$CO$-(C_{1-12})$alkylene-, $-$C(O)—, $-$N$(R_x)$$-$C(O)$-$O—, $-$N$(R_x)$$-$C(O)$-$O$-(C_{1-12})$alkylene-, $-(C_{1-12})$alkylene-N$(R_x)$$-$C(O)$-$O—, $-(C_{1-8})$alkylene-N$(R_x)$$-$C(O)$-$O$-(C_{1-8})$alkylene-, $-(C_{1-12})$alkylene-O$-$CO$-$N$(R_x)$—, $-$O$-$CO$-$N$(R_x)$$-(C_{1-12})$alkylene-, $-(C_{1-8})$alkylene-O$-$CO$-$N$(R_x)$$-(C_{1-8})$alkylene-, $-$O$-$CO$-$N$(R_x)$—, $-$O$-$CO$-$O—, $-(C_{1-12})$alkylene-O$-$CO$-$O—, $-$O$-$CO$-$O$-(C_{1-12})$alkylene- or $-(C_{1-8})$alkylene-O$-$C(O)$-$O$-(C_{1-8})$alkylene-;

$Z_1$ is a direct bond, $-(C_{1-12})$alkylene-, $-$O$-(C_{1-12})$alkylene-, $-$N$(R_x)$$-(C_{1-12})$alkylene-, $-$N$(R_x)$$-$C(O)$-(C_{1-12})$alkylene-, $-(C_{1-8})$alkylene-N$(R_x)$-C(O)$-(C_{1-8})$alkylene-, $-$CO$-$N$(R_x)$$-(C_{1-12})$alkylene-, $-(C_{1-8})$alkylene-CO$-$N$(R_x)$$-(C_{1-8})$alkylene-, $-$OC(O)$-(C_{1-12})$alkylene-, $-$C(O)$-$O$-(C_{1-12})$alkylene-, $-(C_{1-8})$alkylene-CO$-(C_{1-8})$alkylene-, $-$CO$-(C_{1-12})$alkylene-, $-$C(O)—, $-$N$(R_x)$$-$C(O)$-$O$-(C_{1-12})$alkylene-, $-(C_{1-8})$alkylene-N$(R_x)$$-$C(O)$-$O$-(C_{1-8})$alkylene-, $-$O$-$CO$-$N$(R_x)$$-(C_{1-12})$alkylene-, $-(C_{1-8})$alkylene-O$-$CO$-$N$(R_x)$$-(C_{1-8})$alkylene-, $-$O$-$CO$-$O$-(C_{1-12})$alkylene- or $-(C_{1-8})$alkylene-O$-$C(O)$-$O$-(C_{1-8})$alkylene-;

R10 is from 0 to 3 substituents selected from hydroxy, halo, $-(C_{1-17})$alkyl, $-$O$-(C_{1-17})$alkyl, $-(CH_2)_{1-6}$-$C_{3-7}$-cycloalkyl, $-(CH_2)_{0-10}$-aryl or $-(CH_2)_{0-10}$-het;

het is a heterocyclic or heteroaromatic ring;

p is 1-18;

with the proviso that when n is 2 and $R_1$ is $(C_{1-6})$alkyl-CH=CH— or $(C_{3-6})$cycloalkyl-CH=CH— then $R_7$ is not H or $(C_{1-8})$alkyl or $R_8$ is not $-$O$-$CO$-$X$-$R_Z$ or $-$O$-$CO$-(CH_2)_m$-$O$-(CH_2)_m$-$X$-$R_Z$ where X is a direct bond, $(C_{1-12})$alkylene, $(C_{1-12})$alkenylene or $(C_{1-12})$alkynylene and $R_z$ is H, $(C_{3-9})$cycloalkyl, phenyl, phenyl substituted by one or more of chloro, methoxy, $(C_{1-18})$alkyl or $(C_{1-18})$alkoxy, pyrrolyl, furanyl, thiofuranyl, indolyl, benzofuranyl, benzothiofuranyl or pyridyl and each m is independently a number from 0 to 13, and with the further proviso that $R_8$ is not $-$OH when n is 2, $R_7$ is H or methyl and $R_1$ is 3-methylbut-1-enylene;

comprising the following steps:

(a) reacting a compound of formula XLI wherein $R_1$ and $R_5$ are defined above, $P_2$ and $P_4$ are protective groups, and R''' is a $(C_{1-6})$alkyl, with the compound of formula VI

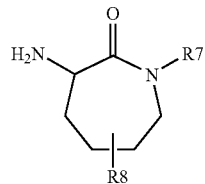

wherein $R_7$ and $R_8$ are defined above, to form the compound of formula XLII

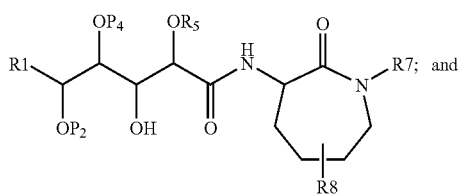

(b) deprotecting the compound of formula XLII.

19. The process as claimed in claim 18, wherein R''' is ethyl, $P_2$ is tert-butyldimethylsilyl, and $P_4$ is selected from benzyl or naphthlmethyl ethers.

20. The process as claimed in claim 18, wherein the compound of formula XLI is prepared by reacting the compound of formula XL

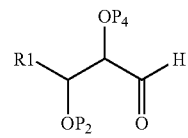

wherein $R_1$, $P_2$ and $P_4$ are defined in claim 18 with a compound having the following formula

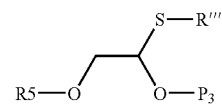

wherein $R_5$ and R''' are defined in claim 18 and $P_3$ is a protective group.

21. The process as claimed in claim 20, wherein the reaction is conducted in the presence of a Lewis acid and a solvent.

22. The process as claimed in claim 21, wherein the Lewis acid is $SnCl_4$ and the solvent is a mixture of $CH_2Cl_2$ and heptane.

* * * * *